(12) United States Patent
Kubo et al.

(10) Patent No.: US 7,598,258 B2
(45) Date of Patent: Oct. 6, 2009

(54) QUINOLINE DERIVATIVES AND QUINAZOLINE DERIVATIVES INHIBITING AUTOPHOSPHORYLATION OF MACROPHAGE COLONY STIMULATING FACTOR RECEPTOR

(75) Inventors: Kazuo Kubo, Takasaki (JP); Hiroaki Ohno, Takasaki (JP); Toshiyuki Isoe, Shibuya-ku (JP); Tuyoshi Nishitoba, Shibuya-ku (JP)

(73) Assignee: Kirin Beer Kabushiki Kaisha, Tokyo-To (JP)

( * ) Notice: Subject to any disclaimer, the term of this patent is extended or adjusted under 35 U.S.C. 154(b) by 471 days.

(21) Appl. No.: 10/510,961

(22) PCT Filed: May 1, 2003

(86) PCT No.: PCT/JP03/05593

§ 371 (c)(1),
(2), (4) Date: Jul. 11, 2005

(87) PCT Pub. No.: WO03/093238

PCT Pub. Date: Nov. 13, 2003

(65) Prior Publication Data

US 2006/0235033 A1    Oct. 19, 2006

(30) Foreign Application Priority Data

May 1, 2002 (JP) .............................. 2002-130049

(51) Int. Cl.
*C07D 215/38* (2006.01)
*A61K 31/44* (2006.01)

(52) U.S. Cl. ............... 514/266.3; 514/312; 546/157; 546/163; 544/287

(58) Field of Classification Search ................. 546/153, 546/157, 163; 544/287; 514/266.3, 312
See application file for complete search history.

(56) References Cited

U.S. PATENT DOCUMENTS

| 6,797,823 B1 * | 9/2004 | Kubo et al. .................. 544/287 |
| 6,821,987 B2 | 11/2004 | Kubo et al. |
| 7,135,466 B2 * | 11/2006 | Sakai et al. ............. 514/217.07 |
| 7,169,789 B2 * | 1/2007 | Kubo et al. .............. 514/266.3 |
| 7,253,286 B2 * | 8/2007 | Funahashi et al. ............ 546/153 |

| 2004/0209905 A1 | 10/2004 | Kubo et al. |
| 2004/0229876 A1 | 11/2004 | Kubo et al. |

FOREIGN PATENT DOCUMENTS

| EP | 0 860 433 | 8/1998 |
| EP | 1 153 920 | 11/2001 |
| WO | WO 97/17329 | * 5/1997 |
| WO | WO 00/43366 | * 1/2000 |
| WO | 02/32872 | 4/2002 |
| WO | WO 03/033472 | 4/2003 |

OTHER PUBLICATIONS

U.S. Appl. No. 11/526,739, filed Sep. 26, 2006, Kubo et al.

* cited by examiner

*Primary Examiner*—D. Margaret Seaman
(74) *Attorney, Agent, or Firm*—Oblon, Spivak, McClelland, Maier & Neustadt, L.L.P.

(57) ABSTRACT

An objective of the present invention is to provide compounds which have inhibitory activity against autophosphorylation of macrophage colony-stimulating factor receptors. The compounds of the present invention are represented by formula (I) and salt and solvate thereof:

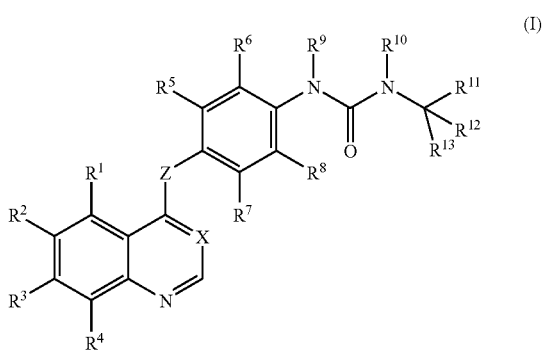

wherein X represents CH or N; Z represents O or S; $R^1$, $R^2$, and $R^3$ represent H, optionally substituted alkoxy or the like; $R^4$ represents H; $R^5$, $R^6$, $R^7$, and $R^8$ represent H, halogen, alkyl, alkoxy, trifluoromethyl or the like; $R^9$ and $R^{10}$ represent H, alkyl or the like; and any one of $R^{11}$ and $R^{12}$ represents H with the other representing alkyl and $R^{13}$ represents an optionally substituted carbocyclic or heterocyclic ring or the like, or $R^{11}$ represents H and $R^{12}$ and $R^{13}$ combine together to form a bicyclic carbocyclic ring.

72 Claims, 2 Drawing Sheets

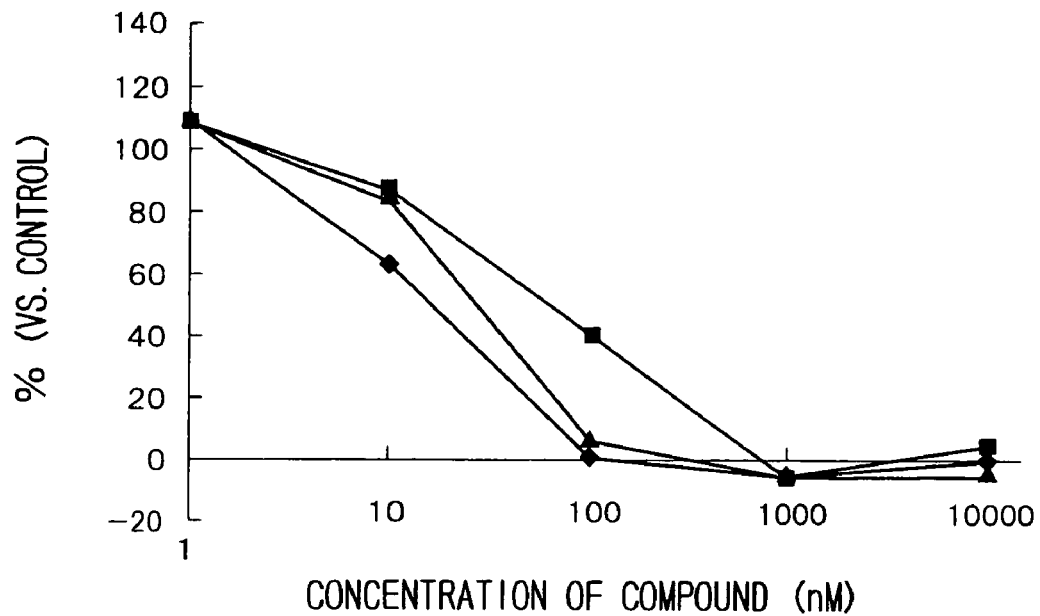
F I G. 1
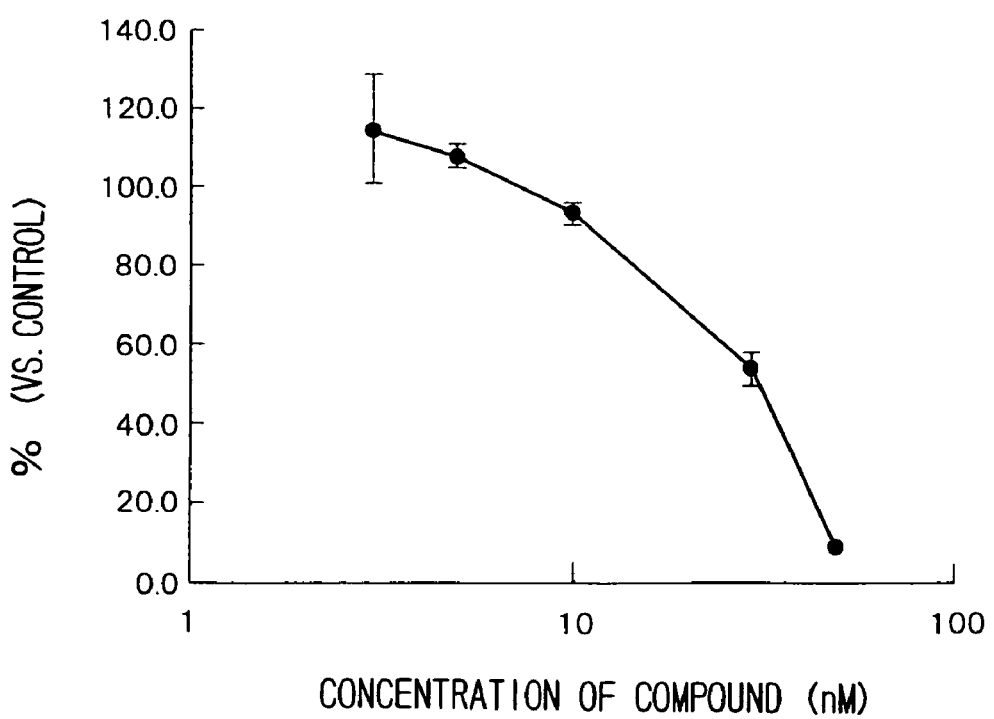
F I G. 2

QUINOLINE DERIVATIVES AND QUINAZOLINE DERIVATIVES INHIBITING AUTOPHOSPHORYLATION OF MACROPHAGE COLONY STIMULATING FACTOR RECEPTOR

BACKGROUND OF THE INVENTION

1. Field of the Invention

The present invention relates to quinoline derivatives and quinazoline derivatives having inhibitory activity against macrophage colony-stimulating factor receptor autophosphorylation, and more particularly to quinoline derivatives and quinazoline derivatives that are useful for the treatment and prevention of diseases such as bone metastasis of malignant tumors including breast cancer, prostatic cancer, and lung cancer, multiple myeloma, osteoporosis, Behcet's disease, rheumatoid arthritis or other diseases.

2. Related Art

Quinoline derivatives and quinazoline derivatives are disclosed in WO 97/17329, Japanese Patent Application No. 328782/1997, and WO 00/43366.

SUMMARY OF THE INVENTION

The present inventors have found that a group of quinoline derivatives and quinazoline derivatives have high inhibitory activity against macrophage colony-stimulating factor receptor autophosphorylation. Macrophage colony-stimulating factor receptor autophosphorylation is known to be involved, e.g., in the onset of diseases such as bone metastasis of malignant tumors including breast cancer, prostatic cancer, and lung cancer; multiple myeloma; osteoporosis; Behcet's disease; and rheumatoid arthritis.

An object of the present invention is to provide a compound having inhibitory activity against macrophage colony-stimulating factor receptor autophosphorylation.

According to the present invention, there are provided compounds represented by formula (I) or pharmaceutically acceptable salts or solvates thereof:

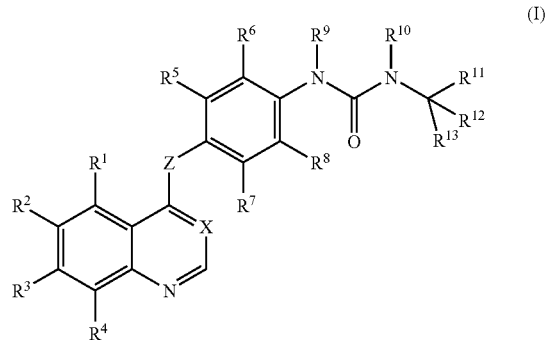

wherein
X represents CH or N;
Z represents O or S;
$R^1$, $R^2$, and $R^3$, which may be the same or different, represent a hydrogen atom; a hologen atom; hydroxyl; cyano; $C_{1-6}$ alkyl; $C_{1-6}$ alkoxy; $C_{2-6}$ alkenyl; $C_{2-6}$ alkynyl; nitro; —$NR^{106}R^{107}$ wherein $R^{106}$ and $R^{107}$, which may be the same or different, represent a hydrogen atom or $C_{1-4}$ alkyl in which the alkyl group is optionally substituted by hydroxyl, —$OR^{108}$ wherein $R^{108}$ represents $C_{1-4}$ alkyl, or —$NR^{109}R^{110}$ wherein $R^{109}$ and $R^{111}$, which may be the same or different, represent a hydrogen atom or $C_{1-4}$ alkyl; —$CONR^{111}R^{112}$ wherein $R^{111}$ and $R^{112}$, which may be the same or different, represent a hydrogen atom or $C_{1-4}$ alkyl in which the alkyl group is optionally substituted by hydroxyl, —$OR^{113}$ wherein $R^{113}$ represents $C_{1-4}$ alkyl, or —$NR^{114}R^{115}$ wherein $R^{114}$ and $R^{115}$, which may be the same or different, represent a hydrogen atom or $C_{1-4}$ alkyl; or —$COOR^{116}$ wherein $R^{116}$ represents a hydrogen atom or $C_{1-4}$ alkyl in which the alkyl group is optionally substituted by hydroxyl, —$OR^{117}$ wherein $R^{117}$ represents $C_{1-4}$ alkyl, or —$NR^{118}R^{119}$ wherein $R^{118}$ and $R^{119}$, which may be the same or different, represent a hydrogen atom or $C_{1-4}$ alkyl in which the $C_{1-6}$ alkyl, $C_{1-6}$ alkoxy, $C_{2-6}$ alkenyl, and $C_{2-6}$ alkynyl groups are optionally substituted by a halogen atom; hydroxyl; $C_{1-4}$ alkyl; $C_{1-4}$ alkoxy; $C_{1-4}$ alkoxycarbonyl; amino in which one or two hydrogen atoms on the amino group each are optionally substituted by $C_{1-4}$ alkyl optionally substituted by hydroxyl or $C_{1-4}$ alkoxy; group $R^{15}R^{16}N$—C(=O)—O— wherein $R^{15}$ and $R^{16}$, which may be the same or different, represent a hydrogen atom or $C_{1-4}$ alkyl in which the alkyl group is optionally substituted by hydroxyl or $C_{1-4}$ alkoxy; or group $R^{17}$—(S)$_m$— wherein $R^{17}$ represents a saturated or unsaturated three- to seven-membered carbocyclic or heterocyclic group optionally substituted by a halogen atom or $C_{1-4}$ alkyl and m is 0 (zero) or 1, $R^4$ represents a hydrogen atom, $R^5$, $R^6$, $R^7$, and $R^8$, which may be the same or different, represent a hydrogen atom, a halogen atom, $C_{1-4}$ alkyl, $C_{1-4}$ alkoxy, $C_{1-4}$ alkylthio, trifluoromethyl, nitro, or amino, $R^9$ and $R^{10}$, which may be the same or different, represent a hydrogen atom, $C_{1-6}$ alkyl, or $C_{1-4}$ alkylcarbonyl, and any one of $R^{11}$ and $R^{12}$ represents a hydrogen atom while the other represents $C_{1-4}$ alkyl, and $R^{13}$ represents a saturated or unsaturated three- to seven-membered carbocyclic or heterocyclic group or a saturated or unsaturated nine- to twelve-membered bicylic carbocyclic group in which the carbocyclic and hetrocyclic groups are optionally substituted by a halogen atom; hydroxyl; $C_{1-4}$ alkyl; $C_{1-4}$ alkoxy; $C_{1-4}$ alkylthio; trifluoromethyl; nitro; or —$NR^{137}R^{138}$ wherein $R^{137}$ and $R^{138}$ which may be the same or different, represent a hydrogen atom or $C_{1-4}$ alkyl in which the alkyl group is optionally substituted by hydroxyl, —$OR^{139}$ wherein $R^{139}$ represents $C_{1-4}$ alkyl, or —$NR^{140}R^{141}$ wherein $R^{140}$ and $R^{141}$, which may be the same or different, represent a hydrogen atom or $C_{1-4}$ alkyl, or $R^{11}$ represents a hydrogen atom, and $R^{12}$ and $R^{13}$ may combine with a carbon atom attached thereto to form a saturated or unsaturated nine- to twelve-membered bicyclic carbocyclic group.

The compounds according to the present invention are useful for the treatment and prevention of diseases such as bone metastasis of malignant tumors including breast cancer, prostatic cancer, and lung cancer, multiple myeloma, osteoporosis, Behcet's disease, rheumatoid arthritis or other diseases.

BRIEF DESCRIPTION OF THE DRAWINGS

FIG. 1 is a diagram showing concentration-dependent inhibition of M-CSF-dependent cell growth of BAC-1.2F5 cell strain by compounds of the present invention, wherein closed squares represent data on the compound of Example 17, closed rhombuses represent data on the compound of Example 18, and closed triangles represent the compound of Example 74, and the values are average value±SE;

FIG. 2 is a diagram showing concentration-dependent inhibition of osteoclast differentiation by the compound of the present invention (Example 74), wherein the values are average value±SE;

DETAILED DESCRIPTION OF THE INVENTION

Compound

Figure 3:
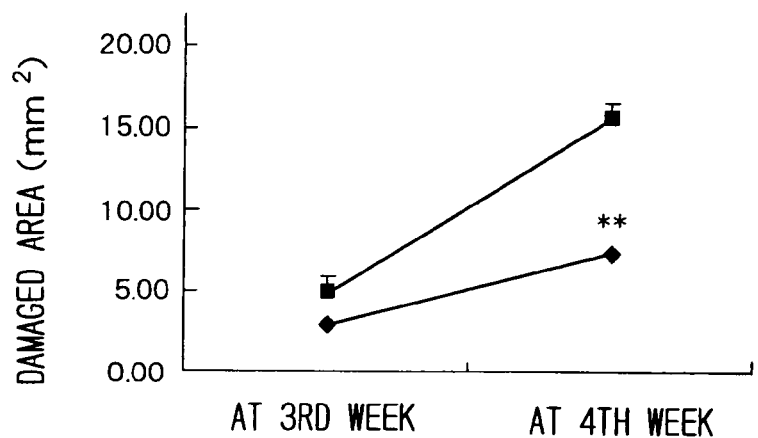
FIG. 3 is a diagram showing the effect of inhibiting the expansion of bone resorption area involved in bone metastasis of melanoma of compounds according to the present invention in a nude mouse bone metastasis model, wherein closed squares represent data on the compound of Example 74 (20 mg, number of doses: twice), and closed rhombus data on a medium; the values are average value±SE; and **: $p<0.01$ (vs. vehicle control)

The terms "$C_{1-6}$ alkyl" and "$C_{1-6}$ alkoxy" as used herein as a group or a part of a group respectively mean straight chain or branched chain alkyl and alkoxy having 1 to 6 carbon atoms, preferably 1 to 4 carbon atoms.

The terms "$C_{2-6}$ alkenyl" and "$C_{2-6}$ alkynyl" as used herein as a group or a part of a group respectively mean straight chain or branched chain alkenyl and alkynyl having 2 to 6 carbon atoms, preferably 2 to 4 carbon atoms.

Examples of $C_{1-6}$ alkyl include methyl, ethyl, n-propyl, isopropyl, n-butyl, i-butyl, s-butyl, t-butyl, n-pentyl, and n-hexyl.

Examples of $C_{1-6}$ alkoxy include methoxy, ethoxy, n-propoxy, i-propoxy, n-butoxy, i-butoxy, s-butoxy, and t-butoxy.

Examples of $C_{2-6}$ alkenyl include allyl, butenyl, pentenyl, and hexenyl.

Examples of $C_{2-6}$ alkynyl include 2-propenyl, butynyl, pentynyl, and hexynyl.

The term "halogen atom" means a fluorine, chlorine, bromine, or iodine atom.

The saturated or unsaturated three- to seven-membered carbocyclic or heterocyclic ring is preferably a five- to seven-membered, more preferably five- or six-membered, saturated or unsaturated carbocyclic or heterocyclic ring.

The saturated or unsaturated nine- to twelve-membered bicyclic carbocyclic or heterocyclic ring is preferably nine- to eleven-membered, more preferably nine- or ten-membered, saturated or unsaturated bicyclic carbocyclic or heterocyclic ring.

Examples of the saturated or unsaturated three- to seven-membered carbocyclic group include phenyl, cycloheptyl, cyclohexyl, and cyclopentyl.

Examples of the saturated or unsaturated nine- to twelve-membered bicyclic carbocyclic group include naphthyl, 1,2,3,4-tetrahydronaphthyl, and indanyl.

The saturated or unsaturated three- to seven-membered heterocyclic ring contains at least one hetero-atom selected from oxygen, nitrogen, and sulfur atoms. The term "heteroatom" as used herein means oxygen, nitrogen, and sulfur atoms. Examples of the saturated or unsaturated three- to seven-membered heterocyclic group include pyridyl, piperidino, piperazino, morpholino, imidazolyl, triazolyl, tetrazolyl, oxazolyl, thiazolyl, pyrrolidinyl, pyrazolyl, isoxazolyl, and isothiazolyl.

$R^1$ preferably represents a hydrogen atom.

$C_{1-6}$ alkyl, $C_{1-6}$ alkoxy, $C_{2-6}$ alkenyl, and $C_{2-6}$ alkynyl, which $R^1$, $R^2$, and $R^3$ may represent, are optionally substituted by $R^{17}$—(S)m- wherein m is preferably 0. The carbocyclic group and the heterocyclic group, which $R^{17}$ may represent, preferably represent a saturated or unsaturated five- or six-membered carbocyclic or heterocyclic group. More preferably, the carboxylic group represents phenyl. More preferably, the heterocyclic group represents a saturated or unsaturated five-membered heterocyclic group containing 1 to 4 nitrogen atoms or a saturated or unsaturated six-membered heterocyclic group containing 1 to 2 hetero-atoms selected from nitrogen and oxygen atoms. The hetero-atom constituting the six-membered heterocyclic group may be more specifically one nitrogen atom and one oxygen atom, or one or two nitrogen atoms.

When m is 0 (zero), —(S)m- represents a single bond.

The substituted $C_{1-6}$ alkoxy, which $R^1$, $R^2$ and $R^3$ may represent, preferably represents group $R^{31}$—$(CH_2)p$—O— wherein $R^{31}$ represents a halogen atom; hydroxyl; $C_{1-4}$ alkyl; $C_{1-4}$ alkoxy; $C_{1-4}$ alkoxycarbonyl; amino in which one or more hydrogen atoms on the amino group each are optionally substituted by $C_{1-4}$ alkyl optionally substituted by hydroxyl or $C_{1-4}$ alkoxy; group $R^{15}R^{16}$N—C(=O)—O— wherein $R^{15}$ and $R^{16}$ are as defined in formula (I); or group $R^{17}$—(S)m- wherein $R^{17}$ is as defined in formula (I), and p is an integer of 1 to 6, preferably 1 to 4.

$R^2$ and $R^3$, which may be the same or different, preferably represent $C_{1-6}$ alkoxy. This alkoxy group is optionally substituted by a halogen atom; hydroxyl; $C_{1-4}$ alkyl; $C_{1-4}$ alkoxy; $C_{1-4}$ alkoxy carbonyl; amino in which one or two hydrogen atoms on the amino group each are optionally substituted by $C_{1-4}$ alkyl optionally substituted by hydroxyl or $C_{1-4}$ alkoxy; or a saturated or unsaturated three- to seven-membered carbocyclic or heterocyclic group.

$R^2$ and $R^3$, which may be the same or different, preferably represent $C_{1-6}$ alkoxy optionally substituted by $R^{17}$—(S)m—, more preferably methoxy or $R^{31}$—$(CH_2)p$—O—.

X preferably represents CH, and Z preferably represents O.

Preferably, at least one of $R^5$, $R^6$, $R^7$, and $R^8$ represents a halogen atom, more preferably a chlorine or fluorine atom, $C_{1-4}$ alkyl, $C_{1-4}$ alkoxy, $C_{1-4}$ alkylthio, trifluoromethyl, nitro, or amino and the remaining groups represent a hydrogen atom.

Preferably, all of $R^5$, $R^6$, $R^7$, and $R^8$ represent a hydrogen atom.

$R^5$ and $R^6$, which may be the same or different, preferably represent a halogen atom, more preferably a chlorine or fluorine atom, $C_{1-4}$ alkyl, $C_{1-4}$ alkoxy, $C_{1-4}$ alkylthio, trifluoromethyl, nitro, or amino, and $R^7$ and $R^8$ represent a hydrogen atom.

$R^6$ and $R^7$, which may be the same or different, preferably represent a halogen atom, more preferably a chlorine or fluorine atom, $C_{1-4}$ alkyl, $C_{1-4}$ alkoxy, $C_{1-4}$ alkylthio, trifluoromethyl, nitro, or amino, and $R^5$ and $R^8$ represent a hydrogen atom.

$R^9$ and $R^{10}$ preferably represent a hydrogen atom.

Preferred examples of the carbocyclic group, which $R^{13}$ may represent, include phenyl and naphthyl.

Preferred examples of the heterocyclic group, which $R^{13}$ may represent, include imidazolyl, oxazolyl, thiazolyl, pyrazolyl, isoxazolyl, and isothiazolyl.

Examples of the bicyclic carbocyclic group, which $R^{12}$ and $R^{13}$ may represent together with a carbon atom attached thereto, include 1,2,3,4-tetrahydronaphthyl and indanyl.

A group of preferred compounds represented by formula (I) include a group of compounds represented by formula (Ia):

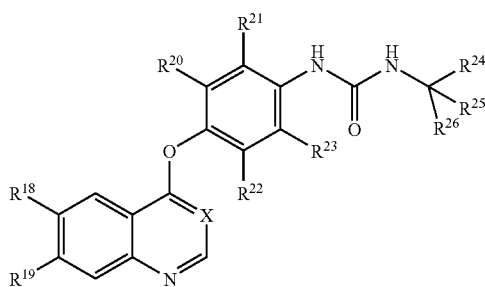

(Ia)

wherein

X represents CH or N, $R^{18}$ and $R^{19}$, which may be the same or different, represent $C_{1-6}$ alkoxy, said alkoxy group being optionally substituted by a halogen atom; hydroxyl; $C_{1-4}$ alkyl; $C_{1-4}$ alkoxycarbonyl; amino in which one or two hydrogen atoms on the amino group each are optionally substituted by $C_{1-4}$ alkyl optionally substituted by hydroxyl or $C_{1-4}$ alkoxy; or a saturated or unsaturated three- to seven-membered carbocyclic or heterocyclic group, $R^{20}$, $R^{21}$, $R^{22}$, and $R^{23}$, which may be the same or different, represent a hydrogen atom, a halogen atom, $C_{1-4}$ alkyl, $C_{1-4}$ alkoxy, $C_{1-4}$ alkylthio, trifluoromethyl, nitro, or amino, any one of $R^{24}$ and $R^{25}$ represents a hydrogen atom and the other represents $C_{1-4}$ alkyl, and $R^{26}$ represents phenyl, naphthyl, imidazolyl, oxazolyl, thiazolyl, pyrazolyl, isoxazolyl, or isothiazolyl, said groups being optionally substituted by a halogen atom, $C_{1-4}$ alkyl, $C_{1-4}$ alkoxy, $C_{1-4}$ alkylthio, trifluoromethyl, nitro, or amino in which one or two hydrogen atoms on the amino group each are optionally substituted by $C_{1-4}$ alkyl, or $R^{24}$ represents a hydrogen atom, and $R^{25}$ and $R^{26}$ combine with a carbon atom attached thereto to form 1,2,3,4-tetrahydronaphthalene or indan.

In formula (Ia), X preferably represents CH.

Preferably, $R^{18}$ and $R^{19}$, which may be the same or different, represent $C_{1-6}$ alkoxy optionally substituted by a saturated or unsaturated three- to seven-membered carbocyclic or heterocyclic group.

Preferably, $R^{18}$ and $R^{19}$, which may be the same or different, represent $C_{1-6}$ alkoxy, more preferably methoxy or $R^{31}$—$(CH_2)p$—O—, optionally substituted by $R^{17}$—$(S)m$—.

Preferably, at least one of $R^{20}$, $R^{21}$, $R^{22}$ and $R^{23}$ represents a halogen atom, preferably a chlorine or fluorine atom, $C_{1-4}$ alkyl, $C_{1-4}$ alkoxy, $C_{1-4}$ alkylthio, trifluoromethyl, nitro, or amino.

Preferably, $R^{20}$ and $R^{21}$, which may be the same or different, represent a halogen atom, more preferablly a chlorine or fluorine atom, $C_{1-4}$ alkyl, $C_{1-4}$ alkoxy, $C_{1-4}$ alkylthio, trifluoromethyl, nitro, or amino, and $R^{22}$ and $R^{23}$ represent a hydrogen atom.

Preferably, $R^{21}$ and $R^{22}$, which may be the same or different, represent a halogen atom, more preferably a chlorine or fluorine atom, $C_{1-4}$ alkyl, $C_{1-4}$ alkoxy, $C_{1-4}$ alkylthio, trifluoromethyl, nitro, or amino, and $R^{20}$ and $R^{23}$ represent a hydrogen atom.

Preferably, all of $R^{20}$, $R^{21}$, $R^{22}$, and $R^{23}$ represent a hydrogen atom.

Preferably, $R^{26}$ represents thiazolyl or 4-fluorophenyl.

A group of preferred compounds represented by formula (I) include compounds represented by formula (Ib)

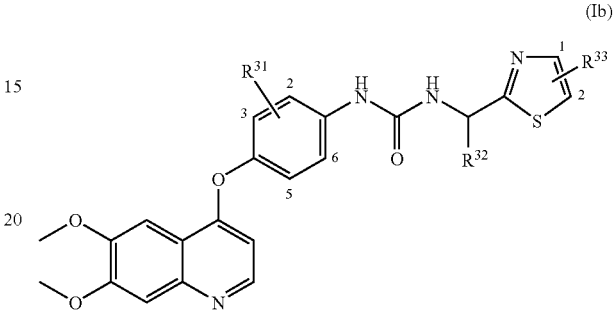

(Ib)

wherein $R^{31}$ represents a hydrogen atom, a fluorine atom at 2-position, a fluorine atom at 3-position, methoxy at 2-position, methoxy at 3-position, or methyl at 2- and 5-positions, $R^{32}$ represents methyl, and $R^{33}$ represents a hydrogen atom, methyl at 1-position, methyl at 2-position, or methyl at 1- and 2-positions.

Formula (Ib) preferably represents formula (Ib-1) and formula (Ib-2):

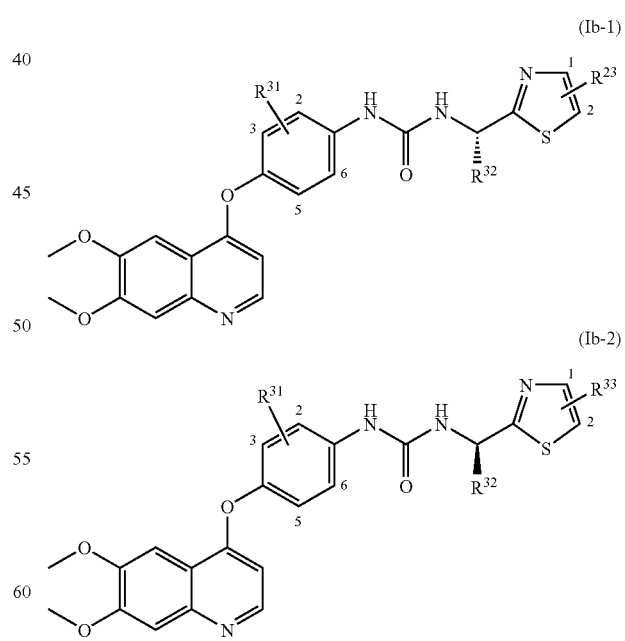

wherein $R^{31}$, $R^{32}$, and $R^{33}$ are as defined in formula (Ib).

A group of preferred compounds represented by formula (I) include compounds represented by formula (Ic)

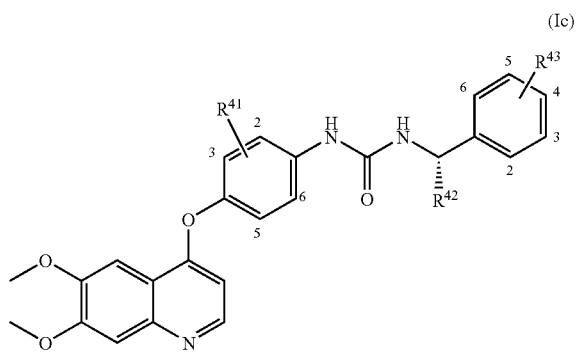

(Ic)

wherein

R$^{41}$ represents a hydrogen atom, a fluorine atom at 2-position, a fluorine atom at 3-position, a chlorine atom at 2-position, a chlorine atom at 3-position, methyl at 2- and 3-positions, methyl at 2- and 5-positions, methoxy at 2-position, methoxy at 3-position, methyl at 2-position, or trifluoromethyl at 2-position, R$^{42}$ represents methyl, R$^{43}$ represents a fluorine atom at 4-position, a bromine atom at 3-position, a bromine atom at 4-position, methoxy at 2-position, methoxy at 3-position, methoxy at 4-position, a chlorine atom at 4-position, methyl at 4-position, or nitro at 4-position.

A group of preferred compounds represented by formula (I) include compounds represented by formula (Id)

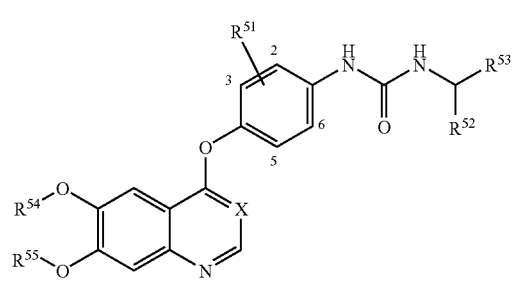

(Id)

wherein

X represents CH or N,

R$^{51}$ represents a hydrogen atom, a fluorine atom at 2-position, a fluorine atom at 3-position, methoxy at 2-position, methoxy at 3-position, or methyl at 2- and 5-positions, R$^{52}$ represents methyl, R$^{53}$ represents imidazolyl, pyrazolyl, oxazolyl, isoxazolyl, thiazolyl, or isothiazolyl in which one or two hydrogen atoms on the groups are optionally substituted by a halogen atom or C$_{1-4}$ alkyl, and R$^{54}$ and R$^{55}$, which may be the same or different, represent a hydrogen atom or C$_{1-6}$ alkyl in which the alkyl group is optionally substituted by hydroxyl; a halogen atom; —OR$^{56}$ wherein R$^{56}$ represents C$_{1-4}$ alkyl; —NR$^{57}$R$^{58}$ wherein R$^{57}$ and R$^{58}$, which may be the same or different, represent a hydrogen atom or C$_{1-4}$ alkyl in which the alkyl group is optionally substituted by hydroxyl or —OR$^{59}$ wherein R$^{59}$ represents C$_{1-4}$ alkyl; or a saturated or unsaturated three- to seven-membered carbocyclic or heterocyclic group in which the carbocyclic and heterocyclic groups are optionally substituted by one or two halogen atoms or C$_{1-4}$ alkyl.

In formula (Id), preferably,
X represents CH, and R$^{52}$ represents

,

In formula (Id), more preferably,
X represents CH, R$^{52}$ represents

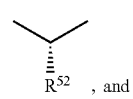

, and

R$^{54}$ and R$^{55}$ represent methyl.

In formula (Id), more preferably,
X represents CH, R$^{52}$ represents

,

R$^{54}$ represents methyl, and

R$^{55}$ represents C$_{1-4}$ alkyl substituted by a saturated or unsaturated five- or six-membered carbocyclic or heterocyclic group.

In formula (Id), preferably,
X represents CH, and R$^{52}$ represents

.

In formula (Id), more preferably,
X represents CH, R$^{52}$ represents

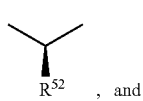

, and

R$^{54}$ and R$^{55}$ represent methyl.

In formula (Id), more preferably,
X represents CH, R$^{52}$ represents

,

R$^{54}$ represents methyl, and

R$^{55}$ represents C$_{1-4}$ alkyl substituted by a saturated or unsaturated five- or six-membered carbocyclic or heterocyclic group.

In formula (Id), preferably,
X represents N, $R^{52}$ represents

In formula (Id), more preferably,
X represents N, $R^{52}$ represents

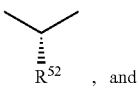, and $R^{54}$ and $R^{55}$ represent methyl.
In formula (Id), more preferably,
X represents N, $R^{52}$ represents

, $R^{54}$ represents methyl, and
$R^{55}$ represents $C_{1-4}$ alkyl substituted by a saturated or unsaturated five- or six-membered carbocyclic or heterocyclic group.
In formula (Id), preferably,
X represents N, and $R^{52}$ represents

.

In formula (Id), more preferably,
X represents N, $R^{52}$ represents

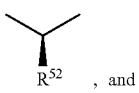, and $R^{54}$ and $R^{55}$ represent methyl.
In formula (Id), more preferably,
X represents N, $R^{52}$ represents

, $R^{54}$ represents methyl, and
$R^{55}$ represents $C_{1-4}$ alkyl substituted by a saturated or unsaturated five- or six-membered carbocyclic or heterocyclic group.

A group of preferred compounds represented by formula (I) include compounds represented by formula (Ie)

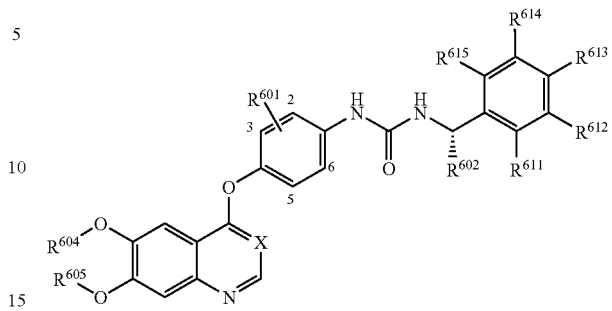

wherein
$R^{601}$ represents a hydrogen atom, a fluorine atom at 2-position, a fluorine atom at 3-position, a chlorine atom at 2-position, a chlorine atom at 3-position, methyl at 2- and 3-positions, methyl at 2- and 5-positions, methoxy at 2-position, methoxy at 3-position, methyl at 2-position, or trifluoromethyl at 2-position,
$R^{602}$ represents methyl,
X represents N or CH,
$R^{604}$ and $R^{605}$, which may be the same or different, represent a hydrogen atom or $C_{1-6}$ alkyl in which the alkyl group is optionally substituted by hydroxyl; a halogen atom; —$OR^{606}$ wherein $R^{606}$ represents $C_{1-4}$ alkyl; —$NR^{607}R^{608}$ wherein $R^{607}$ and $R^{608}$, which may be the same or different, represent a hydrogen atom or $C_{1-4}$ alkyl in which the alkyl group is optionally substituted by hydroxyl or —$OR^{609}$ wherein $R^{609}$ represents $C_{1-4}$ alkyl; or a saturated or unsaturated three- to seven-membered carbocyclic or heterocyclic group in which the carbocyclic and heterocyclic groups are optionally substituted by one or two halogen atoms or $C_{1-4}$ alkyl, and
$R^{611}$, $R^{612}$, $R^{613}$, $R^{614}$, and $R^{615}$, which may be the same or different, represent a hydrogen atom; hydroxyl; $C_{1-6}$ alkyl; —$OR^{616}$ wherein $R^{616}$ represents $C_{1-4}$ alkyl; a halogen atom; nitro; or —$NR^{617}R^{618}$ wherein $R^{617}$ and $R^{618}$, which may be the same or different, represent a hydrogen atom or $C_{1-4}$ alkyl in which the alkyl group is optionally substituted by hydroxyl, —$OR^{619}$ wherein $R^{619}$ represents $C_{1-4}$ alkyl, or —$NR^{620}R^{621}$ wherein $R^{620}$ and $R^{621}$, which may be the same or different, represent a hydrogen atom or $C_{1-4}$ alkyl.

Compounds in a preferred embodiment represented by formula (Ie) include (1) compounds in which X represents CH and all of $R^{611}$, $R^{612}$, $R^{613}$, $R^{614}$, and $R^{615}$ represent a hydrogen atom, or any one of $R^{611}$, $R^{612}$, $R^{613}$, $R^{614}$, and $R^{615}$ represents a group other than a hydrogen atom, preferably, $C_{1-6}$ alkyl, —$OR^{616}$, a halogen atom, or nitro, and the remaining groups represent a hydrogen atom, (2) compounds in which X represents CH and all of $R^{611}$, $R^{612}$, $R^{613}$, $R^{614}$, and $R^{615}$ represent a hydrogen atom, or any one of $R^{611}$, $R^{612}$, $R^{613}$, $R^{614}$, and $R^{615}$ represents a group other than a hydrogen atom, preferably, $C_{1-6}$ alkyl, —$OR^{616}$, a halogen atom, or nitro, and the remaining groups represent a hydrogen atom, $R^{604}$ and $R^{605}$ represent methyl, (3) compounds in which X represents CH and all of $R^{611}$, $R^{612}$, $R^{613}$, $R^{614}$, and $R^{615}$ represent a hydrogen atom, or any one of $R^{611}$, $R^{612}$, $R^{613}$, $R^{614}$, and $R^{615}$ represents a group other than a hydrogen atom, preferably, $C_{1-6}$ alkyl, —$OR^{616}$, a halogen atom, or nitro, and the remaining groups represent a hydrogen atom, $R^{604}$ represents methyl and $R^{605}$ represents $C_{1-4}$ alkyl substituted by a saturated or unsaturated five- or six-membered carbocyclic or heterocyclic group, (4) compounds in which X represents N and all of $R^{611}$, $R^{612}$, $R^{613}$, $R^{614}$, and $R^{615}$ represent a hydrogen atom, or any one of $R^{611}$, $R^{612}$, $R^{613}$, $R^{614}$, and $R^{615}$ represents a group other than a hydrogen atom, preferably, $C_{1-6}$ alkyl, —$OR^{616}$, a halogen atom, or nitro, and the remaining groups represent a hydrogen atom, (5) compounds in which X represents N and all of $R^{611}$, $R^{612}$, $R^{613}$, $R^{614}$, and $R^{615}$ represent a hydrogen atom, or any one of $R^{611}$, $R^{612}$, $R^{613}$, $R^{614}$, and $R^{615}$ represents a group other than a hydrogen atom, preferably, $C_{1-6}$ alkyl, —$OR^{616}$, a halogen atom, or nitro, and the remaining groups represent a hydrogen atom, $R^{604}$ and $R^{605}$ represent methyl, and (6) compounds in which X represents N and any one of $R^{611}$, $R^{612}$, $R^{613}$, $R^{614}$ and $R^{615}$ represents a group other than a hydrogen atom, preferably, $C_{1-6}$ alkyl, —$OR^{616}$, a halogen atom, or nitro, and the remaining groups represent a hydrogen atom, $R^{604}$ represents methyl and $R^{605}$ represents $C_{1-4}$ alkyl substituted by a saturated or unsaturated five- or six-membered carbocyclic or heterocyclic group.

In each of preferred embodiments (1) to (6) represented by formula (Ie), more preferred embodiments of the compounds in which any one of $R^{611}$, $R^{612}$, $R^{613}$, $R^{614}$, and $R^{615}$ represents a group other than a hydrogen atom include compounds in which $R^{611}$ represents methoxy and $R^{612}$, $R^{613}$, $R^{614}$, and $R^{615}$ represent a hydrogen atom, compounds in which $R^{612}$ represents a bromine atom or methoxy and $R^{611}$, $R^{613}$, $R^{614}$, and $R^{615}$ represent a hydrogen atom, and compounds in which $R^{613}$ represents a bromine atom, a chlorine atom, a fluorine atom, methyl, methoxy, or nitro with $R^{611}$, $R^{612}$, $R^{614}$, and $R^{615}$ representing a hydrogen atom.

A group of preferred compounds represented by formula (I) include compounds represented by formula (If)

(If)

wherein

X represents CH or N, $R^{701}$ represents a hydrogen atom, a fluorine atom at 2-position, a fluorine atom at 3-position, methoxy at 2-position, methoxy at 3-position, or methyl at 2- and 5-positions, $R^{702}$ represents $C_{1-4}$ alkyl, $R^{703}$ represents imidazolyl, pyrazolyl, oxazolyl, isoxazolyl, thiazolyl, or isothiazolyl in which one or two hydrogen atoms on the groups are optionally substituted by a halogen atom or $C_{1-4}$ alkyl, and $R^{704}$ and $R^{705}$, which may be the same or different, represent a hydrogen atom; hydroxyl; nitro; cyano; a halogen atom; —$NR^{706}R^{707}$ wherein $R^{706}$ and $R^{707}$, which may be the same or different, represent a hydrogen atom or $C_{1-4}$ alkyl in which the alkyl group is optionally substituted by hydroxyl, —$OR^{708}$ wherein $R^{708}$ represents $C_{1-4}$ alkyl, or —$NR^{709}R^{710}$ wherein $R^{709}$ and $R^{710}$, which may be the same or different, represent a hydrogen atom or $C_{1-4}$ alkyl; —$CONR^{711}R^{712}$ wherein $R^{711}$ and $R^{712}$, which may be the same or different, represent a hydrogen atom is or $C_{1-4}$ alkyl in which the alkyl group is optionally substituted by hydroxyl, —$OR^{713}$ wherein $R^{713}$ represents $C_{1-4}$ alkyl, or —$NR^{714}R^{715}$ wherein $R^{714}$ and $R^{715}$, which may be the same or different, represent a hydrogen atom or $C_{1-4}$ alkyl; —$COOR^{716}$ wherein $R^{716}$ represents a hydrogen atom or $C_{1-4}$ alkyl in which the alkyl group is optionally substituted by hydroxyl, —$OR^{717}$ wherein $R^{717}$ represents $C_{1-4}$ alkyl, or —$NR^{718}R^{719}$ wherein $R^{718}$ and $R^{719}$, which may be the same or different, represent a hydrogen atom or $C_{1-4}$ alkyl; $C_{1-6}$ alkyl; $C_{2-6}$ alkenyl; $C_{2-6}$ alkynyl; or $C_{1-6}$ alkoxy, in which the alkyl, alkenyl, alkynyl, and alkoxy groups are optionally substituted by hydroxyl, a halogen atom, —$OR^{720}$ in which $R^{720}$ represents $C_{1-4}$ alkyl, —$NR^{721}R^{722}$ wherein $R^{721}$ and $R^{722}$, which may be the same or different, represent a hydrogen atom or $C_{1-4}$ alkyl in which the alkyl group is optionally substituted by hydroxyl or —$OR^{723}$ wherein $R^{723}$ represents $C_{1-4}$ alkyl, or a saturated or unsaturated three- to seven-membered carbocyclic or heterocyclic group in which the carbocyclic and heterocyclic groups are optionally substituted by one or two halogen atoms or $C_{1-4}$ alkyl.

In formula (If), preferably,

X represents CH, and $R^{702}$ represents and, more preferably, in this configuration, $R^{702}$ represents methyl.

In formula (If), more preferably,

X represents CH, and $R^{702}$ represents and, more preferably, in this configuration, $R^{702}$ represents methyl, and $R^{704}$ and $R^{705}$ represent methoxy.

In formula (If), more preferably,

X represents CH, and $R^{702}$ represents and, more preferably, in this configuration, $R^{702}$ represents methyl, $R^{704}$ represents methoxy, and $R^{705}$ represents $C_{1-4}$ alkoxy substituted by a saturated or unsaturated five- or six-membered carbocyclic or heterocyclic group.

In formula (If), preferably,
X represents CH, and R$^{702}$ represents $$\underset{R^{702}}{\vee}$$

and, more preferably, in this configuration, R$^{702}$ represents methyl.

In formula (If), more preferably,
X represents CH, and R$^{702}$ represents $$\underset{R^{702}}{\vee}$$

and, more preferably, in this configuration, R$^{702}$ represents methyl, and
R$^{704}$ and R$^{705}$ represent methoxy.

In formula (If), more preferably,
X represents CH, R$^{702}$ represents $$\underset{R^{702}}{\vee}$$

and, more preferably, in this configuration, R$^{702}$ represents methyl, and
R$^{704}$ represents methoxy, and R$^{705}$ represents C$_{1-4}$ alkoxy substituted by a saturated or unsaturated five- or six-membered carbocyclic or heterocyclic group.

In formula (If), preferably,
X represents N, and R$^{702}$ represents $$\underset{R^{702}}{\vee}$$

and, more preferably, in this configuration, R$^{702}$ represents methyl.

In formula (If), more preferably,
X represents N, and R$^{702}$ represents $$\underset{R^{702}}{\vee}$$

and, more preferably, in this configuration, R$^{702}$ represents methyl, and
R$^{704}$ and R$^{705}$ represent methoxy.

In formula (If), more preferably,
X represents N, and R$^{702}$ represents $$\underset{R^{702}}{\vee}$$

and, more preferably, in this configuration, R$^{702}$ represents methyl,
R$^{704}$ represents methoxy, and
R$^{705}$ represents C$_{1-4}$ alkoxy substituted by a saturated or unsaturated five- or six-membered carbocyclic or heterocyclic group.

In formula (If), preferably,
X represents N, and R$^{702}$ represents $$\underset{R^{702}}{\vee}$$

and, more preferably, in this configuration, R$^{702}$ represents methyl.

In formula (If), more preferably,
X represents N, and R$^{702}$ represents $$\underset{R^{702}}{\vee}$$

and, more preferably, in this configuration, R$^{702}$ represents methyl, and
R$^{704}$ and R$^{705}$ represent methoxy.

In formula (If), more preferably,
X represents N, R$^{702}$ represents $$\underset{R^{702}}{\vee}$$

and, more preferably, in this configuration, R$^{702}$ represents methyl, and
R$^{704}$ represents methoxy, and R$^{705}$ represents C$_{1-4}$ alkoxy substituted by a saturated or unsaturated five- or six-membered carbocyclic or heterocyclic group.

A group of preferred compounds represented by formula (I) include compounds represented by formula (Ig)

(Ig)

wherein

X represents CH or N, $R^{801}$ represents a hydrogen atom, a fluorine atom at 2-position, a fluorine atom at 3-position, a chlorine atom at 2-position, a chlorine atom at 3-position, methyl at 2- and 3-positions, methyl at 2- and 5-positions, methoxy at 2-position, methoxy at 3-position, methyl at 2-position, or trifluoromethyl is at 2-position, $R^{802}$ represents $C_{1-4}$ alkyl, $R^{804}$ and $R^{805}$, which may be the same or different, represent a hydrogen atom; hydroxyl; nitro; cyano; a halogen atom; $-NR^{806}R^{807}$ wherein $R^{806}$ and $R^{807}$, which may be the same or different, represent a hydrogen atom or $C_{1-4}$ alkyl in which the alkyl group is optionally substituted by hydroxyl, $-OR^{808}$ wherein $R^{808}$ represents $C_{1-4}$ alkyl, or $-NR^{809}R^{810}$ wherein $R^{809}$ and $R^{810}$, which may be the same or different, represent a hydrogen atom or $C_{1-4}$ alkyl; $-CONR^{811}R^{812}$ wherein $R^{811}$ and $R^{812}$, which may be the same or different, represent a hydrogen atom or $C_{1-4}$ alkyl in which the alkyl group is optionally substituted by hydroxyl, $-OR^{813}$ wherein $R^{813}$ represents $C_{1-4}$ alkyl, or $-NR^{814}R^{815}$ wherein $R^{814}$ and $R^{815}$, which may be the same or different, represent a hydrogen atom or $C_{1-4}$ alkyl; $-COOR^{816}$ wherein $R^{816}$ represents a hydrogen atom or $C_{1-4}$ alkyl in which the alkyl group is optionally substituted by hydroxyl, $-OR^{817}$ wherein $R^{817}$ represents $C_{1-4}$ alkyl, or $-NR^{818}R^{819}$ wherein $R^{818}$ and $R^{819}$, which may be the same or different, represent a hydrogen atom or $C_{1-4}$ alkyl; $C_{1-6}$ alkyl; $C_{2-6}$ alkenyl; $C_{2-6}$ alkynyl; or $C_{1-6}$ alkoxy, in which the alkyl, alkenyl, alkynyl, and alkoxy groups are optionally substituted by hydroxyl, a halogen atom, $-OR^{820}$ in which $R^{820}$ represents $C_{1-4}$ alkyl, $-NR^{821}R^{822}$ wherein $R^{821}$ and $R^{822}$, which may be the same or different, represent a hydrogen atom or $C_{1-4}$ alkyl in which the alkyl group is optionally substituted by hydroxyl or $-OR^{823}$ wherein $R^{823}$ represents $C_{1-4}$ alkyl, or a saturated or is unsaturated three- to seven-membered carbocyclic or heterocyclic group in which the carbocyclic and heterocyclic groups are optionally substituted by one or two halogen atoms or $C_{1-4}$ alkyl, and $R^{831}$, $R^{832}$, $R^{833}$, $R^{834}$, and $R^{835}$, which may be the same or different, represent a hydrogen atom; hydroxyl; $C_{1-6}$ alkyl; $-OR^{836}$ wherein $R^{836}$ represents $C_{1-4}$ alkyl; a halogen atom; nitro; or $-NR^{837}R^{838}$ wherein $R^{837}$ and $R^{838}$, which may be the same or different, represent a hydrogen atom or $C_{1-4}$ alkyl in which the alkyl group is optionally substituted by hydroxyl, $-OR^{839}$ wherein $R^{839}$ represents $C_{1-4}$ alkyl, or $-NR^{840}R^{841}$ wherein $R^{840}$ and $R^{841}$, which may be the same or different, represent a hydrogen atom or $C_{1-4}$ alkyl.

Compounds in a preferred embodiment of formula (Ig) include (1) compounds in which X represents CH and all of $R^{831}$, $R^{832}$, $R^{833}$, $R^{834}$, and $R^{835}$ represent a hydrogen atom, or any one of $R^{831}$, $R^{832}$, $R^{833}$, $R^{834}$, and $R^{835}$ represents a group other than a hydrogen atom, preferably, $C_{1-6}$ alkyl, $-OR^{836}$, a halogen atom, or nitro, and the remaining groups represent a hydrogen atom, (2) compounds in which X represents CH and all of $R^{831}$, $R^{832}$, $R^{833}$, $R^{834}$, and $R^{835}$ represent a hydrogen atom, or any one of $R^{831}$, $R^{832}$, $R^{833}$, $R^{834}$, and $R^{835}$ represents a group other than a hydrogen atom, preferably, $C_{1-6}$ alkyl, $-OR^{836}$, a halogen atom, or nitro, and the remaining groups represent a hydrogen atom, and $R^{804}$ and $R^{805}$ represent methoxy, (3) compounds in which X represents CH and all of $R^{831}$, $R^{832}$, $R^{833}$, $R^{834}$, and $R^{835}$ represent a hydrogen atom, or any one of $R^{831}$, $R^{832}$, $R^{833}$, $R^{834}$, and $R^{835}$ represents a group other than a hydrogen atom, preferably $C_{1-6}$ alkyl, $-OR^{836}$, a halogen atom, or nitro, and the remaining groups represent a hydrogen atom, $R^{804}$ represents methoxy and $R^{805}$ represents $C_{1-4}$ alkoxy substituted by a saturated or unsaturated five- or six-membered carbocyclic or heterocyclic group, (4) compounds in which X represents CH, $R^{802}$ represents methyl, and all of $R^{831}$, $R^{832}$, $R^{833}$, $R^{834}$, and $R^{835}$ represent a hydrogen atom, or any one of $R^{831}$, $R^{832}$, $R^{833}$, $R^{834}$, and $R^{835}$ represents a group other than a hydrogen atom, preferably $C_{1-6}$ alkyl, $-OR^{836}$, a halogen atom, or nitro, and the remaining groups represent a hydrogen atom, (5) compounds in which X represents CH, and all of $R^{831}$, $R^{832}$, $R^{833}$, $R^{834}$, and $R^{835}$ represent a hydrogen atom, or any one of $R^{831}$, $R^{832}$, $R^{833}$, $R^{834}$, and $R^{835}$ represents a group other than a hydrogen atom, preferably $C_{1-6}$ alkyl, $-OR^{836}$, a halogen atom, or nitro, and the remaining groups represent a hydrogen atom, and $R^{804}$ and $R^{805}$ represent methoxy, (6) compounds in which X represents CH, and all of $R^{831}$, $R^{832}$, $R^{833}$, $R^{834}$, and $R^{835}$ represent a hydrogen atom, or any one of $R^{831}$, $R^{832}$, $R^{833}$, $R^{834}$, and $R^{835}$ represents a group other than a hydrogen atom, preferably $C_{1-6}$ alkyl, $-OR^{836}$, a halogen atom, or nitro, and the remaining groups represent a hydrogen atom, $R^{804}$ represents methoxy and $R^{805}$ represents $C_{1-4}$ alkoxy substituted by a saturated or unsaturated five- or six-membered carbocyclic or heterocyclic group, (7) compounds in which X represents N, all of $R^{831}$, $R^{832}$, $R^{833}$, $R^{834}$, and $R^{835}$ represents a hydrogen atom, or any one of $R^{831}$, $R^{832}$, $R^{833}$, $R^{834}$, and $R^{835}$ represents a group other than a hydrogen atom, preferably $C_{1-6}$ alkyl, $-OR^{836}$, a halogen atom, or nitro, and the remaining groups represent a hydrogen atom, (8) compounds in which X represents N, all of $R^{831}$, $R^{832}$, $R^{833}$, $R^{834}$, and $R^{835}$ represent a hydrogen atom, or any one of $R^{831}$, $R^{832}$, $R^{833}$, $R^{834}$, and $R^{835}$ represent a group other than a hydrogen atom, preferably $C_{1-6}$ alkyl, $-OR^{836}$, a halogen atom, or nitro, and the remaining groups represent a hydrogen atom, and $R^{804}$ and $R^{805}$ represent methoxy, (9) compounds in which X represent N, all of $R^{831}$, $R^{832}$, $R^{833}$, $R^{834}$, and $R^{835}$ represent a hydrogen atom, or any one of $R^{831}$, $R^{832}$, $R^{833}$, $R^{834}$, and $R^{835}$ represents a group other than a hydrogen atom, preferably $C_{1-6}$ alkyl, $-OR^{836}$, a halogen atom, or nitro, and the remaining groups represent a hydrogen atom, $R^{804}$ represents methoxy, and $R^{805}$ represents $C_{1-4}$ alkoxy substituted by a saturated or unsaturated five- or six-membered carbocyclic or heterocyclic group,

(10) compounds in which X represents N, $R^{802}$ represents methyl, all of $R^{831}$, $R^{832}$, $R^{833}$, $R^{834}$, and $R^{835}$ represent a hydrogen atom, or any one of $R^{831}$, $R^{832}$, $R^{833}$, $R^{834}$, and $R^{835}$ represents a group other than a hydrogen atom, preferably $C_{1-6}$ alkyl, $-OR^{836}$, a halogen atom, or nitro, and the remaining groups represent a hydrogen atom,

(11) compounds in which X represents N, all of $R^{831}$, $R^{832}$, $R^{833}$, $R^{834}$, and $R^{835}$ represent a hydrogen atom, or any one of $R^{831}$, $R^{832}$, $R^{833}$, $R^{834}$, and $R^{835}$ represents a group other than a hydrogen atom, preferably $C_{1-6}$ alkyl, $-OR^{836}$, a halogen atom, or nitro, and the remaining groups represent a hydrogen atom, and $R^{804}$ and $R^{805}$ represent methoxy, and

(12) compounds in which X represents N, all of $R^{831}$, $R^{832}$, $R^{833}$, $R^{834}$, and $R^{835}$ represent a hydrogen atom, or any one of $R^{831}$, $R^{832}$, $R^{833}$, $R^{834}$ and $R^{835}$ represents a group other than a hydrogen atom, preferably $C_{1-6}$ alkyl, $-OR^{836}$, a halogen atom, or nitro, and the remaining groups represent a hydrogen atom, $R^{804}$ represents methoxy, and $R^{805}$ represents $C_{1-4}$ alkoxy substituted by a saturated or unsaturated five- or six-membered carbocyclic or heterocyclic group.

In each of preferred embodiments (1) to (12) of formula (Ig), more preferred embodiments of the compounds in which any one of $R^{831}$, $R^{832}$, $R^{833}$, $R^{834}$, and $R^{835}$ represents a group other than a hydrogen atom include compounds in which $R^{831}$ represents methoxy and $R^{832}$, $R^{833}$, $R^{834}$, and $R^{835}$ represent a hydrogen atom, compounds in which $R^{832}$ represents a bromine atom or methoxy and $R^{831}$, $R^{833}$, $R^{834}$, and $R^{835}$ represent a hydrogen atom, and compounds in which $R^{833}$ represents a bromine atom, a chlorine atom, a fluorine atom, methyl, methoxy, or nitro, with $R^{831}$, $R^{832}$, $R^{834}$, and $R^{835}$ representing a hydrogen atom.

Examples of preferred compounds of the present invention include compounds described in Examples 1 to 38 and 41 to 105.

Examples of more preferred compounds according to the present invention include the following compounds:

(16) N-{4-[(6,7-dimethoxy-4-quinolyl)oxy]-2-methoxyphenyl}-N'-[1-(4-fluorophenyl)ethyl]urea;

(17) N-{4-[(6,7-dimethoxy-4-quinolyl)oxy]-2-methoxyphenyl}-N'-[(1S)-1-(4-fluorophenyl)ethyl]urea;

(18) N-{4-[(6,7-dimethoxy-4-quinolyl)oxy]-2-methoxyphenyl}-N'-[(1R)-1-(4-fluorophenyl)ethyl]urea;

(74) N-{4-[(6,7-dimethoxy-4-quinolyl)oxy]-2-methoxyphenyl}-N'-[1-(1,3-thiazol-2-yl)ethyl]urea;

(75) N-{4-[(6,7-dimethoxy-4-quinolyl)oxy]-2-methoxyphenyl}-N'-[(1S)-1-(1,3-thiazol-2-yl)ethyl]urea; and

(76) N-{4-[(6,7-dimethoxy-4-quinolyl)oxy]-2-methoxyphenyl}-N'-[(1R)-1-(1,3-thiazol-2-yl)ethyl]urea.

Compounds according to the present invention may form pharmaceutically acceptable salts thereof. Preferred examples of such salts include: alkali metal or alkaline earth metal salts such as sodium salts, potassium salts or calcium salts; hydrohalogenic acid salts such as hydrofluoride salts, hydrochloride salts, hydrobromide salts, or hydroiodide salts; inorganic acid salts such as nitric acid salts, perchloric acid salts, sulfuric acid salts, or phosphoric acid salts; lower alkylsulfonic acid salts such as methanesulfonic acid salts, trifluoromethanesulfonic acid salts, or ethanesulfonic acid salts; arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, maleic acid salts, acetic acid salts, malic acid salts, lactic acid salts, or ascorbic acid salts; and amino acid salts such as glycine salts, phenylalanine salts, glutamic acid salts, or aspartic acid salts.

Pharmaceutically acceptable solvates of the compounds according to the present invention include, for example, hydrates, alcoholates, for example, ethanolates, and etherates.

One or more enantiomeric carbon atoms, which form enantiomer configuration, may exist in the compounds according to the present invention. The compounds according to the present invention include all enantiomers.

Production of Compounds

Compounds according to the present invention may be produced, for example, according to scheme 1, scheme 2, scheme 3, and scheme 4.

Scheme 1

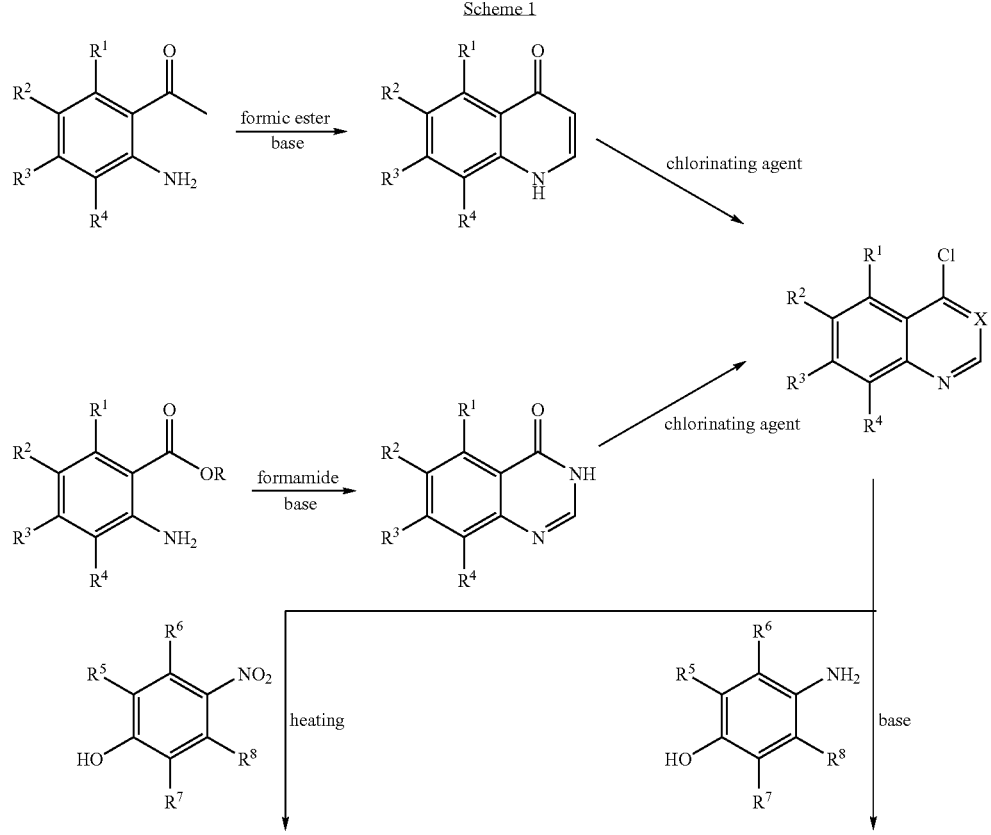

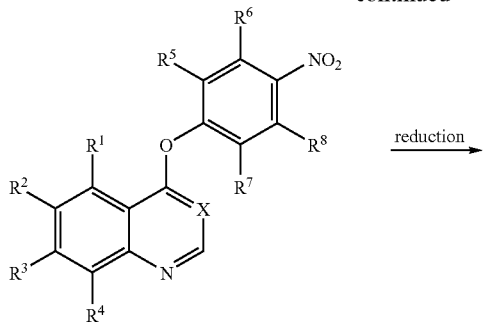

In the formula, R represents $C_{1-6}$ alkyl or the like; and $R^1$, $R^2$, $R^3$, $R^4$, $R^5$, $R^6$, $R^7$, $R^8$, and X are as defined in formula (I).

Starting compounds necessary for the synthesis of the compounds according to the present invention are commercially available or can be easily produced by a conventional method. For example, 4-chloroquinoline derivatives may be synthesized by a conventional method described, for example, in Org. Synth. Col. Vol. 3, 272 (1955), Acta Chim. Hung., 112, 241 (1983) or WO 98/47873.

Alternatively, 4-chloroquinazoline derivatives may be produced by first (1) reacting a benzoic ester with formamide to give a quinazolone derivative and subsequently (2) heating the 4-quinazolone derivatives using toluene or sulfolane as a solvent in the presence of phosphorus oxychloride. The quinazolone derivative may be synthesized by reacting a benzoic ester, sodium methoxide, and formamide in the presence of a solvent such as N,N-dimethylformamide or methanol.

Next, a 4-(aminophenoxy)quinoline derivative or a corresponding quinazoline derivative is produced by reacting nitrophenol with the 4-chloroquinoline derivative or corresponding quinazoline derivative in the presence or absence of a suitable solvent to synthesize a 4-(nitrophenoxy)quinoline derivative or a corresponding quinazoline derivative, then conducting stirring in a suitable solvent, for example, N,N-dimethyl formamide, in the presence of a catalyst, for example, palladium hydroxide-carbon or palladium-carbon, under a hydrogen atmosphere. Alternatively, the 4-(aminophenoxy)quinoline derivative or a corresponding quinazoline derivative may also be produced by reacting amino phenol with a 4-chloroquinoline derivative or a corresponding quinazoline derivative in the presence of a base, for example, sodium hydride.

Alternatively, the 4-(aminophenoxy)quinazoline derivative may be produced by dissolving amino phenol in an aqueous sodium hydroxide solution and subjecting the solution to a two-phase reaction with a solution of the 4-chloroquinazoline derivative in an organic solvent in the presence of a phase transfer catalyst, for example, tetra-n-butylammonium bromide, or in the absence of the catalyst.

Scheme 2

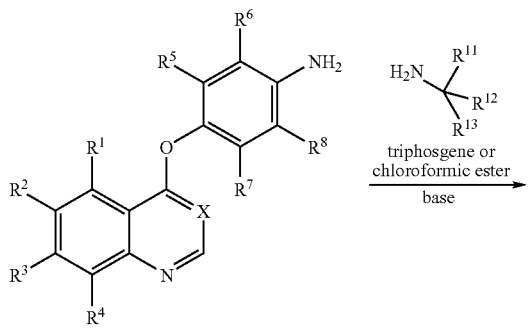

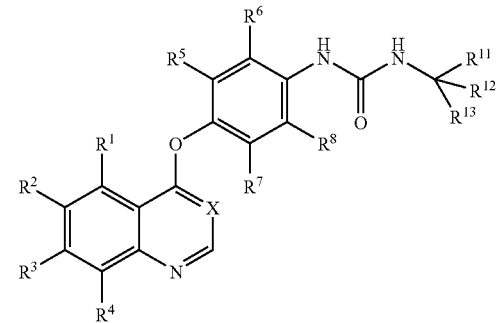

wherein $R^1$, $R^2$, $R^3$, $R^4$, $R^5$, $R^6$, $R^7$, $R^8$, $R^{11}$, $R^{12}$, $R^{13}$ and X are as defined in formula (I).

A urea derivative in which $R^9$ and/or $R^{10}$ represent a hydrogen atom may be produced according to a conventional method, i.e., by adding triphosgene or a chloroformic ester to a 4-(aminophenoxy)quinoline derivative prepared in scheme 1 or a corresponding quinazoline derivative and then reacting the mixture with a suitable amine derivative ($R^{11}R^{12}R^{13}CNH_2$) in the presence of a base, for example, triethylamine (scheme 2).

Scheme 3

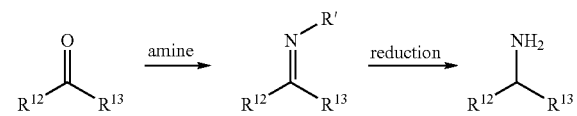

wherein R' represents hydroxyl, $C_{1-4}$ alkyl or the like; and $R^{12}$, $R^{13}$, and X are as defined in formula (I).

The amine derivative ($R^{11}R^{12}R^{13}CNH_2$) may be produced, for example, by reacting a commercially available acylated aryl compound or a heteroaryl compound with a suitable primary amine, for example, hydroxyamine, for conversion to an imine derivative and then treating the imine derivative with a suitable reducing agent, for example, zinc (scheme 3).

$R^9$ and $R^{10}$ can be introduced by reacting a urea derivative, in which $R^9$ and/or $R^{10}$ represent a hydrogen atom, with a suitable alkylating agent ($R^9$Hal or $R^{10}$Hal wherein Hal represents a halogen atom) in the presence of a base, for example, sodium hydride.

Scheme 4

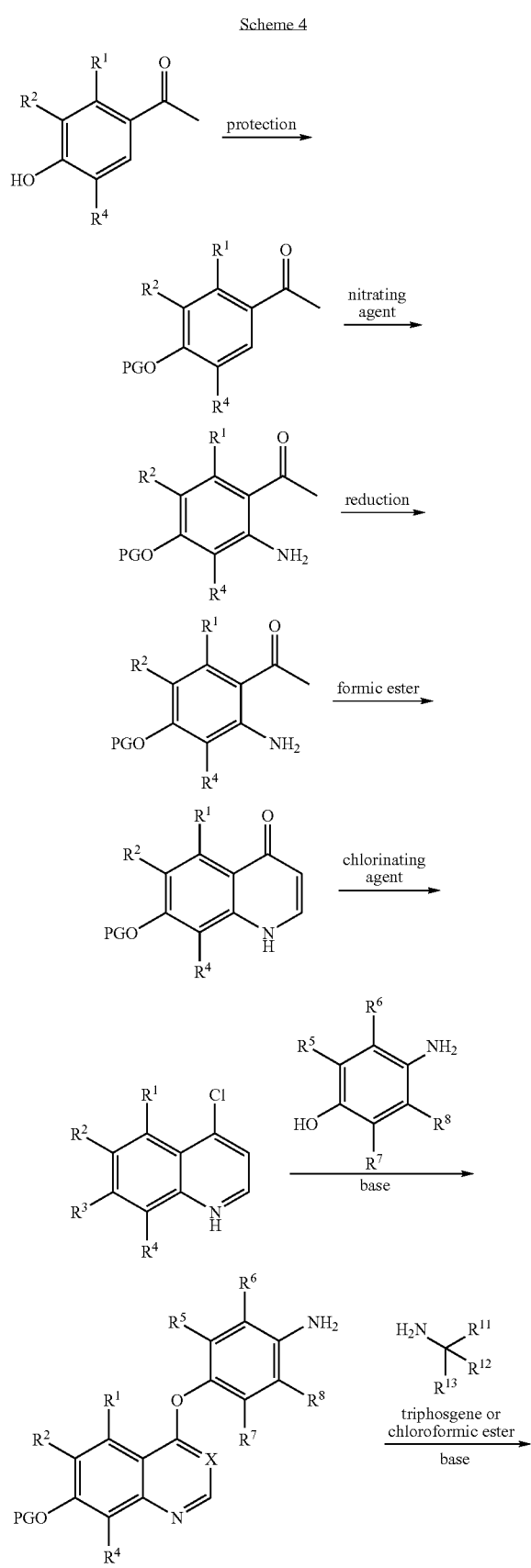

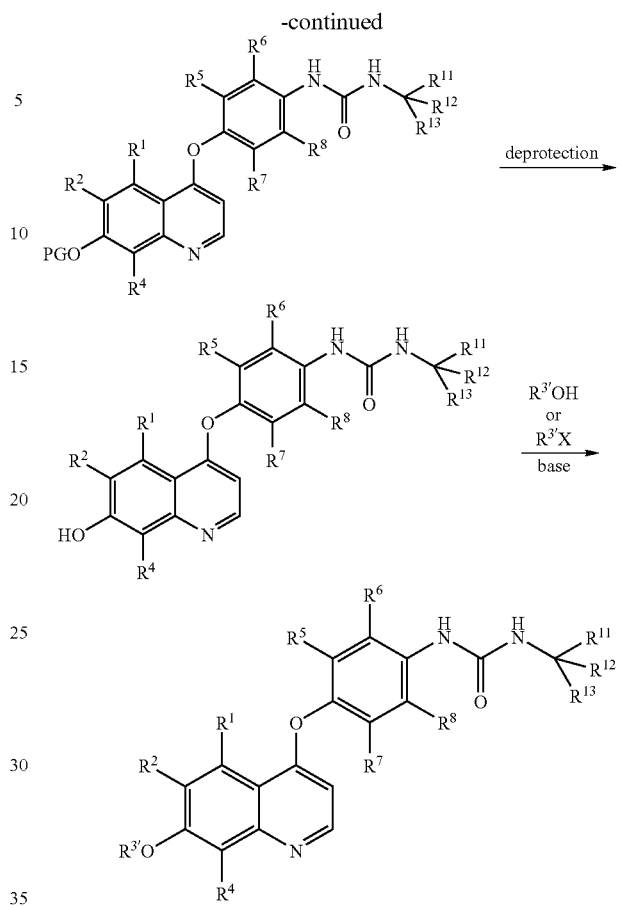

wherein PG represents a protective group of hydroxyl; $R^{3\prime}$ represents $C_{1-6}$ alkyl, wherein the alkyl group is optionally substituted by the same substituent as the substituent of alkoxy represented by $R^3$; and $R^1$, $R^2$, $R^3$, $R^4$, $R^5$, $R^6$, $R^7$, $R^8$, $R^{11}$, $R^{12}$ and $R^{13}$ are as defined in formula (I).

The derivative having a specific substituent at the 7-position of the quinoline ring may be produced, for example, by scheme 4.

A nitro group may be introduced by first reacting a commercially available 4'-hydroxyacetophenone derivative with a suitable substituent, for example, benzyl, to protect hydroxyl, and then reacting the reaction product with a nitrating agent, for example, nitric acid-acetic acid.

Next, a 4-chloroquinoline derivative may be produced by reducing the nitro group to give an amino group, then reacting the amino group with a formic ester in the presence of a base to give a quinolone which was then reacted with a chlorinating agent, for example, phosphorus oxychloride.

An 4-(aminophenoxy)quinoline derivative is produced by reacting an aminophenol with the 4-chloroquinoline derivative prepared above in the presence of a base, for example, sodium hydride. Next, a urea derivative may be produced by a conventional method, i.e., by adding triphosgene or a chloroformic ester in the presence of a base, for example, triethylamine, and then reacting the mixture with a suitable amine derivative ($R^{11}R^{12}R^{13}CNH_2$).

The compound of the present invention having alkoxy at the 7-position of the quinoline ring can be produced by removing the protective group (PG) of hydroxyl at the 7-position of the quinoline ring and reacting the deprotected compound with an alkyl halide in the presence of a base or by treating an alcohol derivative according to a conventional method, for example, Mitsunobu reaction.

The alkyl halide used in the substitution reaction is commercially available or alternatively may be produced according to a method described, for example, in J. Am. Chem. Soc., 1945, 67, 736.

The alcohol derivative used in the substitution reaction is commercially available, or alternatively may be produced by a method, for example, described in J. Antibiot. (1993), 46 (1), 177 and Ann. Pharm. Fr. 1997, 35, 503.

The derivative having a specific substituent at the 6-position of the quinoline ring may be produced in the same manner as in scheme 4, except that a 3'-hydroxyacetophenone derivative is used as a starting compound.

The derivative having a specific substituent at the 7-position of the quinazoline ring may be produced in the same manner as in scheme 4, except that a 4-hydroxybenzoic ester derivative is used as a starting compound and formamide instead of the formic ester.

The derivative having a specific substituent at the 6-position of the quinazoline ring may be produced in the same manner as in scheme 4, except that a 3-hydroxybenzoic ester derivative is used as a starting compound and formamide instead of the formic ester.

The compound represented by formula (I) wherein Z represents S may be produced according to scheme 1 by reacting an aminothiophenol derivative with a 4-chloroquinoline derivative or a corresponding quinazoline derivative in a suitable solvent, for example, chlorobenzene, to give a 4-(quinolylsulfanyl)aniline derivative or a 4-(quinazolinylsulfanyl)aniline derivative which is then reacted with an amine derivative according to scheme 2.

Use of Compounds/Pharmaceutical Composition

Bone is a tissue which is maintained by repeating bone resorption and bone formation, and cells responsible for a bone resorption function are osteoclasts. Various factors are known as factors for accelerating differentiation of osteoclasts in vivo. RANKL which has been recently identified as a differentiation-inducing factor of osteoclasts may be mentioned as a representative example of such factors. RANKL induces differentiation of osteoclasts from splenic cells and marrow cells in vitro. In this case, the presence of a macrophage colony stimulating factor (hereinafter referred to as "M-CSF") is indispensable. On the other hand, that M-CSF is indispensable in vivo is apparent from the fact that, upon deletion of osteoclasts, op/op mice, i.e., animals which do not produce normal M-CSF, exhibit osteopetrosis (Yoshida H, et al., Nature, 345, 442-444 (1990) "The Murine Mutation Osteopetrosis is in the Coding Region of the Macrophage Colony Stimulating Factor Gene"), and the fact that the administration of activated M-CSF to the mice can cure osteopetrosis. Osteoclasts are important cells responsible for bone resorption in maintaining bone tissue, but on the other hand, in diseases such as bone metastasis of malignant tumors including breast cancer, prostatic cancer, and lung cancer, multiple myeloma, osteoporosis, Behcet's disease, rheumatoid arthritis or other diseases, enhanced bone resorption of osteoclasts in bone tissue is causative of worsening of condition of diseases. Therefore, these clinical conditions and cancer pain caused by bone metastasis can be ameliorated by inhibiting the differentiation of osteoclasts to reduce the number of osteoclasts. Osteoclasts are derived from monocytoid cells which are hemocytes. In precursor cells thereof, signals which promote differentiation of osteoclasts are transmitted through an M-CSF receptor (hereinafter referred to as "c-fms"). It is known that c-fms is receptor tyrosine kinase and binding of M-CSF thereto leads to activation of tyrosine kinase on the receptor. The receptor tyrosine kinase functions to transmit signals through autophosphorylation of the receptor per se. Therefore, differentiation induction to osteoclasts can is be inhibited by inhibiting the autophosphorylation of c-fms. As a result, the number of osteoclasts in vivo can be reduced.

Compounds according to the present invention inhibited the autophosphorylation of mouse c-fms which occurs upon stimulation of macrophage-like cell line BAC-1.2F5, capable of stably expressing mouse c-fms in vitro, by M-CSF (see Pharmacological Test Example 1).

Compounds according to the present invention exhibited concentration-dependent inhibition of M-CSF-dependent cell growth of BAC-1.2F5 in vitro (see Pharmacological Text Example 2).

Further, compounds according to the present invention exhibited concentration-dependent inhibition of differentiation of osteoclasts in vitro (see Pharmacological Text Example 3).

Compounds according to the present invention inhibited the expansion of bone resorption area involved in bone metastasis of melanoma in a nude mouse bone metastasis model and in a nude rat bone metastasis model (see Pharmacological Text Examples 4 and 5).

Furthermore, compounds according to the present invention inhibited differentiation of osteoclasts in a rat osteoporosis model (see Pharmacological Text Example 6).

Accordingly, the compounds according to the present invention can be used for the theraphy and prophylaxis of a disease for which the inhibition of M-CSF receptor autophosphorylation is effective therapeutically.

Diseases for which the inhibition of M-CSF receptor autophosphorylation is effective therapeutically include bone metastasis of malignant tumors including breast cancer, prostatic cancer, and lung cancer; multiple myeloma; osteoporosis; Behcet's disease; and rheumatoid arthritis.

The compounds according to the present invention can be administered to human and non-human animals orally or parenterally by administration routes, for example, intravenous administration, intramuscular administration, subcutaneous administration, rectal administration, or percutaneous administration. Therefore, the pharmaceutical composition comprising as an active ingredient the compound according to the present invention is formulated into suitable dosage forms according to the administration routes.

Specifically, oral preparations include tablets, capsules, powders, granules, and syrups, and parental preparations include injections, suppositories, tapes, and ointments.

These various preparations may be prepared by conventional methods, for example, with commonly used excipients, disintegrants, binders, lubricants, colorants, and diluents.

Excipients include, for example, lactose, glucose, corn starch, sorbit, and crystalline cellulose. Disintegrants include, for example, starch, sodium alginate, gelatin powder, calcium carbonate, calcium citrate, and dextrin. Binders include, for example, dimethylcellulose, polyvinyl alcohol, polyvinyl ether, methylcellulose, ethylcellulose, gum arabic, gelatin, hydroxypropylcellulose, and polyvinyl pyrrolidone. Lubricants include, for example, talc, magnesium stearate, polyethylene glycol, and hydrogenated vegetable oils.

In preparing the injections, if necessary, for example, buffers, pH adjustors, stabilizers, tonicity agents, and preservatives may be added.

The content of the compound according to the present invention in the pharmaceutical composition according to the present invention may vary depending upon the dosage form.

In general, however, the content is 0.5 to 50% by weight, preferably 1 to 20% by weight, based on the whole composition.

The dose may be appropriately determined in consideration of, for example, the age, weight, sex, difference in diseases, and severity of condition of individual patients, for example, in the range of 0.01 to 100 mg/kg, preferably 0.1 to 50 mg/kg. This dose is administered at a time daily or divided doses of several times daily.

The compound according to the present invention may be administered in combination with other medicament. In this case, the compound according to the present invention may be administered simultaneously with or after or before the administration of other medicament. For example, when the target disease is bone metastasis of malignant tumors such as breast cancer, prostatic cancer, and lung cancer, or osteolysis caused by malignant tumors such as multiple myeloma, it is considered that the action of the compound according to the present invention on precursor cells of osteoclasts reduces osteoclasts to inhibit osteolysis and subsequent administration of a carcinostatic agent can efficiently inhibit the growth of the malignant tumor within the bone. The kind of the carcinostatic agent, dosage interval and the like can be determined depending upon the kind of cancer and the condition of the patient. Diseases other than malignant tumors can also be similarly treated.

According to the present invention, the contact of the compound of the present invention with precursor cells of osteoclasts can be conducted, for example, by systemic administration, for example, intravenous administration or oral administration, topical administration, for example, dermal administration or intraarticular administration, drug targeting using a carrier, for example, liposome, lipid microsphere, or polymerized pharmaceutical preparation.

According to the present invention, there is provided use of the compound according to the present invention, for the manufacture of an agent for use in the treatment and prevention of a disease for which the inhibition of M-CSF receptor autophosphorylation is effective therapeutically.

Further, according to the present invention, there is provided a method for treating and preventing a disease for which the inhibition of M-CSF receptor autophosphorylation is effective therapeutically, said method comprising the step of administering a therapeutically or prophylactically effective amount of the compound according to the present invention together with a pharmaceutically acceptable carrier to a mammal.

Selective Inhibition of c-fms

The present invention provides a compound which can selectively inhibit c-fms rather than KDR (see Pharmacological Test Example 7). A group of such compounds include compounds of formula (Ib), formula (Ic), formula (Id), formula (Ie), formula (If), and formula (Ig), particularly, compounds of Examples 17, 74, 75, and 76.

It is known that proteins including tyrosine kinase domains play a very important role, for example, in signal transmission in vivo and there are many kinds of such proteins. In general, "selective" action of the medicament on the target site is considered to reduce side effects. Therefore, the use of the inhibitor capable of selectively acting on M-CSF receptor (c-fms) tyrosine kinase as the target of the compound according to the present invention is considered to reduce the side effect.

In addition to c-fms, VEGF receptor (KDR) is known as a protein containing tyrosine kinase domain. It has been proven that the inhibition of the phosphorylation of KDR can inhibit angiogenesis, and a KDR phosphorylation inhibitor is regarded as useful for the treatment of a disease for which the inhibition of angiogenesis is desired. On the other hand, angiogenesis is desired in organs such as kidney. For example, in a progressive renal failure model in rats, there is a report that repair of blood capillaries by VEGF exhibits therapeutic effect (Yukinari Masuda, et al: VEGF Accelerates Glomerular Repair in GN. Am J Pathol, 159: 599-608, 2001). Therefore, KDR phosphorylation inhibitory activity in organs for which angiogenesis is desired possibly has adverse effect on the function of the organs. In particular, in the case of therapy of bone metastasis of cancers or therapy of osteoporosis in which medication is carried out over an extended time, there is a fear of this adverse effect.

For the above reason, it can be said that, among c-fms inhibitors, compounds which selectively inhibit c-fms rather than KDR is more advantageous from the viewpoint of lower possibility of sacrificing the function of an organ for which angiogenesis is desired.

EXAMPLES

The present invention is further illustrated by the following Examples that are not intended as a limitation of the invention.

Production Example 1

1-(1,3-Thiazol-2-yl)-1-ethanone oxime (Mixture of Isomers)

Commercially available 2-acetyl thiazole (1.27 g) and commercially available hydroxylamine hydrochloride (830 mg) were dissolved in ethanol (40 ml) to prepare a solution. Pyridine (0.97 ml) was added to the solution, and the mixture was stirred at room temperature overnight. Water was added to the reaction solution, and the mixture was extracted three times with ethyl acetate. The organic layer was washed with water and was dried over sodium sulfate. The solvent was removed by evaporation and was dried by means of a vacuum pump to give the title compound (1.25 g, 88%).

$^1$H-NMR (CDCl$_3$): δ 2.43 (s, 3H), 2.49 (s, 3H), 7.31 (d, J=3.2 Hz, 1H), 7.60 (d, J=3.4 Hz, 1H), 7.85 (d, J=3.2 Hz, 1H), 8.01 (d, J=3.2 Hz, 1H)

Production Example 2

1-(1,3-Thiazol-2-yl)-1-ethylamine 1-(1,3-Thiazol-2-yl)-1-ethanone oxime (710 mg) was dissolved in methanol (10 ml) to prepare a solution. Ammonium chloride (1.35 g) and zinc (powder) (6.5 g) were added to the solution, and the mixture was heated under reflux for 2 hr. Thereafter, 10% sodium hydroxide (10 ml) was added thereto, and the mixture was extracted three times with chloroform. The organic layer was washed with saturated brine and was dried over sodium sulfate. The solvent was removed by evaporation and was dried by means of a vacuum pump to give the title compound (580 mg, 91%).

$^1$H-NMR (CDCl$_3$): δ 1.55 (d, J=6.8 Hz, 3H), 4.43 (q, J=6.8 Hz, 3H), 7.24 (d, J=3.4 Hz, 1H), 7.71 (d, J=3.2 Hz, 1H)

Production Example 3

1-(1,3-Thiazol-2-yl)-1-ethylamine (Optically Active Substance)

1-(1,3-Thiazol-2-yl)-1-ethylamine (racemate) (2.0 g) was dissolved in dichloromethane (20 ml) to prepare a solution.

Triethylamine (2.5 ml) was added to the solution, and the mixture was cooled to 0° C. Di-tert-butyl dicarbonate (3.7 g) was added thereto, and the mixture was stirred at room temperature for 3 hr. Water (40 ml) was added thereto, and the mixture was extracted three times with chloroform. The organic layer was washed with saturated brine and was dried over sodium sulfate. The solvent was removed, and the residue was purified by chromatography on silica gel using hexane/ethyl acetate for development to give tert-butyl N-[1-(1,3-thiazol-2-yl)ethyl]carbamate (racemate) (2.8 g, 62%).

$^1$H-NMR (CDCl$_3$): δ 1.46 (s, 9H), 1.60 (d, J=6.8 Hz, 3H), 5.12 (br, 1H), 5.25 (br, 1H), 7.25 (dd, J=0.5, 3.2 Hz, 1H), 7.70 (dd, J=0.5, 3.2 Hz, 1H)

Tert-butyl N-[1-(1,3-thiazol-2-yl)ethyl]carbamate (racemate) prepared above was resolved into optical isomers with an optical isomer resolution column (Daicel Chemical Industries, Ltd.). Optically active N-[1-(1,3-thiazol-2-yl)ethyl]carbamate (400 mg) was dissolved in dichloromethane (10 ml) to prepare a solution which was then cooled to 0° C. Trifluoroacetic acid (4 ml) was added to the cooled solution, and the temperature of the mixture was then raised to room temperature before the mixture was stirred for 90 min. Thereafter, 10% aqueous sodium hydroxide solution was added thereto, and, after it was confirmed that the solution was rendered basic, the solution was stirred at room temperature for 30 min and was then extracted three times with chloroform. The organic layer was washed with saturated brine and was dried over sodium sulfate. The solvent was removed by evaporation and was dried by means of a vacuum pump to quantitatively give the title compound.

Production Example 4

1-(5-Methyl-1,3-thiazol-2-yl)-1-ethanone

Commercially available 5-methyl-1,3-thiazole (218 mg) was dissolved in tetrahydrofuran (5 ml) to prepare a solution which was then cooled to −78° C. A hexane solution (1.56 M) (1.4 ml) of n-butyllithium was slowly added to the cooled solution over a period of 10 min, and the mixture was stirred at −78° C. for 2 hr. N-Methoxy-N-methylacetamide (206 mg) was dissolved in tetrahydrofuran (2 ml) to prepare a solution which was then slowly added thereto over a period of 10 min, followed by stirring at −78° C. for 2 hr. The cooling bath was removed, an aqueous saturated ammonium chloride solution (5 ml) was added, and the mixture was stirred for 30 min. Further, water (5 ml) was added thereto, and the reaction solution was extracted with ethyl acetate. The organic layer was washed with saturated brine and was dried over sodium sulfate. The solvent was removed, and the residue was purified by chromatography on silica gel using hexane/ethyl acetate for development to give the title compound (267 mg, 86%).

$^1$H-NMR (CDCl$_3$): δ 2.56 (d, J=1.0 Hz, 3H), 2.67 (s, 3H), 7.65 (d, J=1.0 Hz, 1H)

Production Example 5

1-(4,5-Dimethyl-1,3-thiazol-2-yl)-1-ethanone

Commercially available 4,5-dimethyl-1,3-thiazole (453 mg) was dissolved in tetrahydrofuran (10 ml) to prepare a solution which was then cooled to −78° C. A hexane solution (1.56 M) (2.8 ml) of n-butyllithium was slowly added over a period of 10 min, and the mixture was stirred at −78° C. for 2 hr. N-Methoxy-N-methylacetamide (454 mg) was dissolved in tetrahydrofuran (2 ml) to prepare a solution which was then slowly added over a period of 10 min, and the mixture was stirred at −78° C. for 2 hr. The cooling bath was removed, an aqueous saturated ammonium chloride solution (10 ml) was added, and the mixture was stirred for 30 min. Further, water (10 ml) was added, and the reaction solution was extracted with ethyl acetate. The organic layer was washed with saturated brine and was dried over sodium sulfate. The solvent was removed, and the residue was purified by chromatography on silica gel using hexane/ethyl acetate for development to give the title compound (609 mg, 98%).

$^1$H-NMR (CDCl$_3$): δ 2.40 (d, J=0.7 Hz, 3H), 2.44 (s, 3H), 2.64 (d, J=0.7 Hz, 3H)

Example 1

N-{4-[(6,7-Dimethoxy-4-quinolyl)oxy]phenyl}-N'-[1-(4-fluorophenyl)ethyl]urea

4-[(6,7-Dimethoxy-4-quinolyl)oxy]aniline (20 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(4-fluorophenyl)ethylamine (35 mg) in chloroform (0.2 ml) was added thereto, and the mixture was stirred at room temperature for 10 hr. The reaction solution was purified by chromatography on silica gel using chloroform/methanol for development to give the title compound (2 mg, yield 8%).

$^1$H-NMR (CDCl$_3$): 1.49 (3H, d, J=6.83 Hz), 4.04 (3H, s), 4.06 (3H, s), 4.92-4.99 (1H, m), 6.42 (1H, d, J=5.34 Hz), 7.02 (2H, dd, J=8.54, 8.54 Hz), 7.07 (2H, d, J=8.78 Hz), 7.33 (2H, dd, J=8.54, 5.37 Hz), 7.37 (1H, s), 7.46 (2H, d, J=8.78 Hz), 7.57 (1H, s), 8.39 (1H, d, J=5.34 Hz)

Mass spectrometric value (ESI-MS, m/z): 460 (M−1)

Example 2

N-{4-[(6,7-Dimethoxy-4-quinolyl)oxy]phenyl}-N'-[(1S)-1-(4-fluorophenyl)ethyl]urea 4-[(6,7-Dimethoxy-4-quinolyl)oxy]aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (33 mg, yield 71%).

$^1$H-NMR (CDCl$_3$): δ 1.49 (3H, d, J=6.83 Hz), 4.04 (3H, s), 4.04 (3H, s), 4.94-4.99 (1H, m), 6.42 (1H, d, J=5.34 Hz), 7.04 (2H, dd, J=8.78, 8.78 Hz), 7.09 (2H, d, J=8.54 Hz), 7.33 (2H, dd, J=8.54, 5.37 Hz), 7.37 (1H, s), 7.46 (2H, d, J=8.78 Hz), 7.57 (1H, s), 8.42 (1H, d, J=5.10 Hz)

Mass spectrometric value (ESI-MS, m/z): 462 (M$^+$+1)

$[α]_D^{24}$ −270.5° (c0.5, CHCl$_3$)

Example 3

N-{4-[(6,7-Dimethoxy-4-quinolyl)oxy]phenyl}-N'-[(1R)-1-(4-fluorophenyl)ethyl]urea 4-[(6,7-Dimethoxy-4-quinolyl)oxy]aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (28 mg, yield 60%).

$^1$H-NMR (CDCl$_3$): δ 1.51 (3H, d, J=6.83 Hz), 4.04 (3H, s), 4.06 (3H, s), 4.94-4.99 (1H, m), 6.42 (1H, d, J=5.34 Hz), 7.02 (2H, dd, J=8.54, 8.54 Hz), 7.07 (2H, d, J=8.78 Hz), 7.33 (2H, dd, J=8.54, 5.37 Hz), 7.39 (1H, s), 7.47 (2H, d, J=8.78 Hz), 7.57 (1H, s), 8.41 (1H, d, J=5.10 Hz)

Mass spectrometric value (ESI-MS, m/z): 462 (M$^+$+1)

$[α]_D^{24}$+270.1° (c0.5, CHCl$_3$)

Example 4

N-{2-Chloro-4-[(6,7-dimethoxy-4-quinolyl)oxy]phenyl}-N'-[1-(4-fluorophenyl)ethyl]urea 2-Chloro-4-[(6,7-dimethoxy-4-quinolyl)oxy]aniline (82 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of 1-(4-fluorophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (40 mg, yield 32%).

$^1$H-NMR (CDCl$_3$): 1.54 (3H, d, J=6.83 Hz), 4.03 (3H, s), 4.04 (3H, s), 4.96 (1H, m), 5.21 (1H, d, J=6.59 Hz), 6.45 (1H, d, J=5.37 Hz), 6.77 (1H, s), 7.03-7.10 (3H, overlapped), 7.17 (1H, d, J=2.68 Hz), 7.36 (2H, dd, J=6.59, 3.42 Hz), 7.42 (1H, s), 7.49 (1H, s), 8.26 (1H, d, J=9.03 Hz), 8.48 (1H, d, J=5.37 Hz)

Mass spectrometric value (ESI-MS, m/z): 494 (M−1)

Example 5

N-{2-Chloro-4-[(6,7-dimethoxy-4-quinolyl)oxy]phenyl}-N'-[(1S)-1-(4-fluorophenyl)ethyl]urea 2-Chloro-4-[(6,7-dimethoxy-4-quinolyl)oxy]aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (9 mg, yield 21%).

$^1$H-NMR (CDCl$_3$): 1.55 (3H, d, J=6.83 Hz), 4.04 (3H, s), 4.04 (3H, s), 4.92-4.98 (1H, m), 5.07 (1H, d, J=6.59 Hz), 6.45 (1H, d, J=5.12 Hz), 6.71 (1H, s), 7.04-7.10 (3H, overlapped), 7.18 (1H, d, J=2.68 Hz), 7.38 (2H, dd, J=8.78, 5.34 Hz), 7.42 (1H, s), 7.50 (1H, s), 8.26 (1H, d, J=9.03 Hz), 8.49 (1H, d, J=5.37 Hz)

Mass spectrometric value (ESI-MS, m/z): 496 (M+1)

$[α]_D^{24}$−32.5° (c0.25, CHCl$_3$)

Example 6

N-{2-Chloro-4-[(6,7-dimethoxy-4-quinolyl)oxy]phenyl}-N'-[(1R)-1-(4-fluorophenyl)ethyl]urea 2-Chloro-4-[(6,7-dimethoxy-4-quinolyl)oxy]aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (17 mg, yield 37%).

$^1$H-NMR (CDCl$_3$): 1.55 (3H, d, J=6.83 Hz), 4.04 (3H, s), 4.04 (3H, s), 4.92-4.98 (1H, m), 5.03 (1H, d, J=6.83 Hz), 6.45 (1H, d, J=5.37 Hz), 6.69 (1H, s), 7.03-7.10 (3H, overlapped), 7.18 (1H, d, J=2.68 Hz), 7.38 (2H, dd, J=5.37, 8.78 Hz), 7.42 (1H, s), 7.49 (1H, s), 8.26 (1H, d, J=9.03 Hz), 8.49 (1H, d, J=5.37 Hz)

Mass spectrometric value (ESI-MS, m/z): 496 (M+1)

$[α]_D^{25}$+27.9° (c0.25, CHCl$_3$)

Example 7

N-{4-[(6,7-Dimethoxy-4-quinolyl)oxy]-2,5-dimethylphenyl}-N'-[1-(4-fluorophenyl)ethyl]urea 4-[(6,7-Dimethoxy-4-quinolyl)oxy]-2,5-dimethoxyaniline (81 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of 1-(4-fluorophenyl)ethylamine (35 mg) in chloroform (0.4 ml) was added thereto, and the mixture was stirred at room temperature for 10 hr. The stirred mixture was purified by chromatography on silica gel using chloroform/methanol for development to give the title compound (41 mg, yield 33%).

$^1$H-NMR (CDCl$_3$): 1.49 (3H, d, J=6.83 Hz), 2.09 (3H, s), 2.12 (3H, s), 4.04 (3H, s), 4.05 (3H, s), 4.97 (1H, m), 5.05 (1H, d, J=6.80 Hz), 6.09 (1H, s), 6.27 (1H, d, J=5.37 Hz), 6.91 (1H, s), 7.02 (2H, dd, J=8.52, 6.36 Hz), 7.33 (2H, dd, J=8.52, 5.12 Hz), 7.42 (1H, s), 7.52 (1H, s), 7.57 (1H, s), 8.43 (1H, d, J=5.37 Hz)

Mass spectrometric value (ESI-MS, m/z): 488 (M−1)

Example 8

N-{4-[(6,7-Dimethoxy-4-quinolyl)oxy]-2,5-dimethylphenyl}-N'-[(1S)-1-(4-fluorophenyl)ethyl]urea 4-[(6,7-Dimethoxy-4-quinolyl)oxy]-2,5-dimethoxyaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (35 mg, yield 77%).

$^1$H-NMR (CDCl$_3$): 1.49 (3H, d, J=6.34 Hz), 2.09 (3H, s), 2.13 (3H, s), 4.05 (3H, s), 4.05 (3H, s), 4.95-5.00 (2H, m), 6.28 (1H, d, J=5.37 Hz), 6.92 (1H, s), 7.04 (2H, dd, J=8.78, 8.78 Hz), 7.33 (2H, dd, J=8.54, 5.12 Hz), 7.42 (1H, s), 7.51 (1H, s), 7.57 (1H, s), 8.44 (1H, d, J=5.12 Hz)

Mass spectrometric value (ESI-MS, m/z): 490 (M+1)

$[\alpha]_D^{25}$+9.6° (c0.5, CHCl$_3$)

Example 9

N-{4-[(6,7-Dimethoxy-4-quinolyl)oxy]-2,5-dimethylphenyl}-N'-[(1R)-1-(4-fluorophenyl)ethyl]urea 4-[(6,7-Dimethoxy-4-quinolyl)oxy]-2,5-dimethoxyaniline (30 mg) was added to chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (35 mg, yield 77%).

$^1$H-NMR (CDCl$_3$): 1.49 (3H, d, J=6.34 Hz), 2.09 (3H, s), 2.13 (3H, s), 4.04 (3H, s), 4.05 (3H, s), 4.95-5.00 (2H, m), 6.04 (1H, s), 6.28 (1H, d, J=5.37 Hz), 6.92 (1H, s), 7.04 (2H, dd, J=8.78, 8.78 Hz), 7.33 (2H, dd, J=8.78, 5.12 Hz), 7.42 (1H, s), 7.51 (1H, s), 7.57 (1H, s), 8.44 (1H, d, J=5.12 Hz)

Mass spectrometric value (ESI-MS, m/z): 490 (M+1)

$[\alpha]_D^{24}$−11.5° (c0.5, CHCl$_3$)

Example 10

N-{3-Chloro-4-[(6,7-dimethoxy-4-quinolyl)oxy] phenyl}-N'-[1-(4-fluorophenyl)ethyl]urea 3-Chloro-4-[(6,7-dimethoxy-4-quinolyl)oxy]aniline (83 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of 1-(4-fluorophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (36 mg, yield 29%).

$^1$H-NMR (CDCl$_3$): 1.48 (3H, d, J=6.83 Hz), 4.01 (3H, s), 4.05 (3H, s), 4.98 (1H, m), 5.44 (1H, d, J=7.07 Hz), 6.28 (1H, d, J=5.37 Hz), 7.01 (2H, dd, J=8.78, 8.78 Hz), 7.10-7.31 (4H, overlapped), 7.39 (1H, s), 7.59 (1H, s), 7.60 (1H, d, J=2.44 Hz), 8.43 (1H, d, J=5.37 Hz)

Mass spectrometric value (ESI-MS, m/z): 494 (M−1)

Example 11

N-{3-Chloro-4-[(6,7-dimethoxy-4-quinolyl)oxy] phenyl}-N'-[(1S)-1-(4-fluorophenyl)ethyl]urea 3-Chloro-4-[(6,7-dimethoxy-4-quinolyl)oxy]aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (26 mg, yield 58%).

$^1$H-NMR (CDCl$_3$): 1.48 (3H, d, J=6.83 Hz), 4.01 (3H, s), 4.05 (3H, s), 4.94-4.99 (1H, m), 5.43 (1H, d, J=6.83 Hz), 6.28 (1H, d, J=5.37 Hz), 7.02 (2H, dd, J=8.78, 8.78 Hz), 7.11 (1H, d, J=8.78 Hz), 7.18 (s, 1H), 7.24 (1H, dd, J=8.78, 2.68 Hz), 7.28 (1H, dd, J=5.37, 8.78 Hz), 7.39 (1H, s), 7.59 (1H, s), 7.60 (1H, d, J=2.44 Hz), 8.43 (1H, d, J=5.12 Hz)

Mass spectrometric value (ESI-MS, m/z): 494 (M−1)

$[\alpha]_D^{24}$45.1° (c0.5, CHCl$_3$)

Example 12

N-{3-Chloro-4-[(6,7-dimethoxy-4-quinolyl)oxy] phenyl}-N'-[(1R)-1-(4-fluorophenyl)ethyl]urea 3-Chloro-4-[(6,7-dimethoxy-4-quinolyl)oxy]aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (26 mg, yield 57%).

$^1$H-NMR (CDCl$_3$): 1.50 (3H, d, J=6.83 Hz), 4.03 (3H, s), 4.05 (3H, s), 4.92-5.00 (1H, m), 5.21 (1H, d, J=7.08 Hz), 6.29 (1H, d, J=5.12 Hz), 6.84 (s, 1H), 7.04 (2H, dd, J=8.78, 8.78 Hz), 7.12 (1H, d, J=8.78 Hz), 7.25 (1H, dd, J=8.78, 2.44 Hz), 7.31 (2H, dd, J=8.54, 5.37 Hz), 7.41 (1H, s), 7.59 (1H, s), 7.61 (1H, d, J=2.44 Hz), 8.44 (1H, d, J=5.37 Hz)

Mass spectrometric value (ESI-MS, m/z): 496 (M+1)

$[\alpha]_D^{25}$+44.2° (c0.5, CHCl$_3$)

Example 13

N-{4-[(6,7-Dimethoxy-4-quinolyl)oxy]-2-methylphenyl}-N'-[1-(4-fluorophenyl)ethyl]urea 4-[(6,7-Dimethoxy-4-quinolyl)oxy]-2-methylaniline (78 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of 1-(4-fluorophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (79 mg, yield 66%).

$^1$H-NMR (CDCl$_3$): 1.49 (3H, d, J=6.59 Hz), 2.13 (3H, s), 4.03 (3H, s), 4.04 (3H, s), 4.97 (1H, m), 5.05 (1H, d, J=6.83 Hz), 6.14 (1H, s), 6.46 (1H, d, J=5.37 Hz), 7.01-7.06 (4H, overlapped), 7.32 (2H, dd, J=8.54, 5.12 Hz), 7.41 (1H, s), 7.52 (1H, s), 7.61 (1H, d, J=8.29 Hz), 8.48 (1H, d, J=5.37 Hz)

Mass spectrometric value (ESI-MS, m/z): 474 (M−1)

Example 14

N-{4-[(6,7-Dimethoxy-4-quinolyl)oxy]-2-methylphenyl}-N'-[(1S)-1-(4-fluorophenyl)ethyl]urea 4-[(6,7-Dimethoxy-4-quinolyl)oxy]-2-methylaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (36 mg, yield 77%).

$^1$H-NMR (CDCl$_3$): 1.49 (3H, d, J=6.83 Hz), 2.17 (3H, s), 4.03 (3H, s), 4.05 (3H, s), 4.87 (1H, d, J=6.83 Hz), 4.94-4.99 (1H, m), 5.97 (1H, s), 6.47 (1H, d, J=5.12 Hz), 7.01-7.07 (4H, m), 7.33 (2H, dd, J=8.54, 5.12 Hz), 7.42 (1H, s), 7.52 (1H, s), 7.58 (1H, d, J=8.29 Hz), 8.48 (1H, d, J=5.37 Hz)

Mass spectrometric value (ESI-MS, m/z): 476 (M+1)

$[\alpha]_D^{24}$+12.6° (c0.5, CHCl$_3$)

Example 15

N-{4-[(6,7-Dimethoxy-4-quinolyl)oxy]-2-methylphenyl}-N'-[(1R)-1-(4-fluorophenyl)ethyl]urea 4-[(6,7-Dimethoxy-4-quinolyl)oxy]-2-methylaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(4-fluorophenyl)ethylamine (35 mg) in is chloroform (0.2 ml) was added thereto, and the mixture was stirred at room temperature for 10 hr. The stirred mixture was purified by chromatography on silica gel using chloroform/methanol for development to give the title compound (26 mg, yield 58%).

$^1$H-NMR (CDCl$_3$): 1.49 (3H, d, J=6.59 Hz), 2.14 (3H, s), 4.03 (3H, s), 4.04 (3H, s), 4.92-4.99 (1H, m), 6.03 (1H, s), 6.47 (1H, d, J=5.37 Hz), 7.01-7.06 (4H, m), 7.33 (2H, dd, J=8.78, 5.37 Hz), 7.42 (1H, s), 7.52 (1H, s), 7.59 (1H, d, J=9.27 Hz), 8.48 (1H, d, J=5.37 Hz)

Mass spectrometric value (ESI-MS, m/z): 476 (M+1)

$[\alpha]_D^{24}$-14.3° (c0.5, CHCl$_3$)

Example 16

N-{4-[(6,7-Dimethoxy-4-quinolyl)oxy]-2-methoxyphenyl}-N'-[1-(4-fluorophenyl)ethyl]urea 4-[(6,7-Dimethoxy-4-quinolyl)oxy]-2-methoxyaniline (82 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of 1-(4-fluorophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (58 mg, yield 47%).

$^1$H-NMR (CDCl$_3$): 1.52 (3H, d, J=6.83 Hz), 3.73 (3H, s), 4.03 (3H, s), 4.04 (3H, s), 4.96 (1H, m), 5.15 (1H, d, J=6.59 Hz), 6.44 (1H, d, J=5.12 Hz), 6.66 (1H, d, J=2.68 Hz), 6.77 (1H, dd, J=8.78, 2.68 Hz), 6.87 (1H, s), 7.04 (2H, dd, J=8.78, 8.78 Hz), 7.36 (2H, dd, J=8.72, 5.37 Hz), 7.41 (1H, s), 7.55 (1H, s), 8.16 (1H, d, J=8.78 Hz), 8.46 (1H, d, J=5.12 Hz)

Mass spectrometric value (ESI-MS, m/z): 490 (M−1)

Example 17

N-{4-[(6,7-Dimethoxy-4-quinolyl)oxy]-2-methoxyphenyl}-N'-[(1S)-1-(4-fluorophenyl)ethyl]urea 4-[(6,7-Dimethoxy-4-quinolyl)oxy]-2-methoxyaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (44 mg, yield 98%).

$^1$H-NMR (CDCl$_3$): 1.52 (3H, d, J=6.83 Hz), 3.73 (3H, s), 4.03 (3H, s), 4.04 (3H, s), 4.96 (1H, m), 5.15 (1H, d, J=6.59 Hz), 6.44 (1H, d, J=5.12 Hz), 6.66 (1H, d, J=2.68 Hz), 6.77 (1H, dd, J=8.78, 2.68 Hz), 6.87 (1H, s), 7.04 (2H, dd, J=8.78, 8.78 Hz), 7.36 (2H, dd, J=8.72, 5.37 Hz), 7.41 (1H, s), 7.55 (1H, s), 8.16 (1H, d, J=8.78 Hz), 8.46 (1H, d, J=5.12 Hz)

Mass spectrometric value (ESI-MS, m/z): 492 (M$^+$+1)

$[\alpha]_D^{24}$-31.6° (c0.5, CHCl$_3$)

Example 18

N-{4-[(6,7-Dimethoxy-4-quinolyl)oxy]-2-methoxyphenyl}-N'-[(1R)-1-(4-fluorophenyl)ethyl]urea 4-[(6,7-Dimethoxy-4-quinolyl)oxy]-2-methoxyaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (43 mg, yield 95%).

$^1$H-NMR (CDCl$_3$): 1.53 (3H, d, J=6.34 Hz), 3.76 (3H, s), 4.04 (3H, s), 4.04 (3H, s), 4.94-4.98 (2H, m), 6.44 (1H, d, J=5.12 Hz), 6.67 (1H, d, J=2.44 Hz), 6.76 (1H, s), 6.78 (1H, d, J=2.44 Hz), 7.06 (2H, dd, J=8.78, 8.78 Hz), 7.37 (2H, dd, J=8.78, 5.37 Hz), 7.41 (1H, s), 7.55 (1H, s), 8.15 (1H, d, J=8.78 Hz), 8.46 (1H, d, J=5.37 Hz)

Mass spectrometric value (ESI-MS, m/z): 492 (M$^+$+1)

$[\alpha]_D^{25}$+30.0° (c0.5, CHCl$_3$)

Example 19

N-[4-[(6,7-Dimethoxy-4-quinolyl)oxy]-2-(trifluoromethyl)phenyl]-N'-[1-(4-fluorophenyl)ethyl]urea 4-[(6,7-Dimethoxy-4-quinolyl)oxy]-2-(trifluoromethyl)aniline (91 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of 1-(4-fluorophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (64 mg, yield 49%).

$^1$H-NMR (CDCl$_3$): 1.52 (3H, d, J=6.83 Hz), 4.03 (3H, s), 4.04 (3H, s), 4.94 (1H, m), 5.23 (1H, d, J=6.59 Hz), 6.44 (1H, d, J=5.37 Hz), 6.57 (1H, s), 7.05 (2H, dd, J=8.78, 8.78 Hz), 7.34 (3H, overlapped), 7.39 (1H, d, J=2.93 Hz), 7.43 (1H, s), 7.49 (1H, s), 8.14 (1H, d, J=9.03 Hz), 8.50 (1H, d, J=5.37 Hz)

Mass spectrometric value (ESI-MS, m/z): 528 (M−1)

Example 20

N-[4-[(6,7-Dimethoxy-4-quinolyl)oxy]-2-(trifluoromethyl)phenyl]-N'-[(1S)-1-(4-fluorophenyl)ethyl]urea 4-[(6,7-Dimethoxy-4-quinolyl)oxy]-2-(trifluoromethyl) aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (9 mg, yield 20%).

$^1$H-NMR (CDCl$_3$): 1.53 (3H, d, J=6.83 Hz), 4.04 (3H, s), 4.05 (3H, s), 4.89-4.96 (1H, m), 5.07 (1H, s), 6.44 (1H, d, J=5.37 Hz), 6.50 (1H, s), 7.06 (2H, dd, J=8.78, 8.78 Hz), 7.33-7.40 (4H, m), 7.43 (1H, s), 7.49 (1H, s), 8.13 (1H, d, J=9.03 Hz), 8.50 (1H, d, J=5.12 Hz)

Mass spectrometric value (ESI-MS, m/z): 530 (M+1)

$[\alpha]_D^{24}$ −40.4° (c0.25, CHCl$_3$)

Example 21

N-[4-[(6,7-Dimethoxy-4-quinolyl)oxy]-2-(trifluoromethyl)phenyl]-N'-[(1R)-1-(4-fluorophenyl)ethyl]urea 4-[(6,7-Dimethoxy-4-quinolyl)oxy]-2-(trifluoromethyl) aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (15 mg, yield 34%).

$^1$H-NMR (CDCl$_3$): 1.53 (3H, d, J=6.83 Hz), 4.04 (3H, s), 4.05 (3H, s), 4.90-4.96 (1H, m), 5.14 (1H, d, J=6.59 Hz), 6.45 (1H, d, J=5.37 Hz), 6.53 (1H, s), 7.05 (2H, dd, J=8.78, 8.78 Hz), 7.31-7.36 (3H, m), 7.39 (1H, d, J=2.68 Hz), 7.43 (1H, s), 7.49 (1H, s), 8.13 (1H, d, J=9.03 Hz), 8.50 (1H, d, J=5.37 Hz)

Mass spectrometric value (ESI-MS, m/z): 530 (M+1)

$[\alpha]_D^{25}$ +39.4° (c0.25, CHCl$_3$)

Example 22

N-{4-[(6,7-Dimethoxy-4-quinolyl)oxy]-3-methoxyphenyl}-N'-[1-(4-fluorophenyl)ethyl]urea 4-[(6,7-Dimethoxy-4-quinolyl)oxy]-3-methoxyaniline (82 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, is a solution of 1-(4-fluorophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (60 mg, yield 49%).

$^1$H-NMR (CDCl$_3$): 1.48 (3H, d, J=6.83 Hz), 2.12 (3H, s), 2.16 (3H, s), 4.05 (3H, s), 4.05 (3H, s), 4.77 (1H, d, J=7.07 Hz), 4.97-5.00 (1H, m), 5.97 (1H, s), 6.25 (1H, d, J=5.12 Hz), 6.99 (1H, dd, J=8.54 Hz), 7.04 (2H, dd, J=8.78, 8.78 Hz), 7.31 (2H, dd, J=5.12, 8.78 Hz), 7.43 (1H, s), 7.59 (1H, s), 8.44 (1H, d, J=5.37 Hz)

Mass spectrometric value (ESI-MS, m/z): 490 (M−1)

Example 23

N-{4-[(6,7-Dimethoxy-4-quinolyl)oxy]-3-methoxyphenyl}-N'-[(1S)-1-(4-fluorophenyl)ethyl]urea 4-[(6,7-Dimethoxy-4-quinolyl)oxy]-3-methoxyaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (45 mg, yield 100%).

$^1$H-NMR (CDCl$_3$): 1.48 (3H, d, J=6.83 Hz), 3.71 (3H, s), 4.00 (3H, s), 4.04 (3H, s), 5.00 (1H, m), 5.48 (1H, d, J=7.32 Hz), 6.29 (1H, d, J=5.37 Hz), 6.62 (1H, dd, J=8.54, 2.44 Hz), 6.99 (3H, overlapped), 7.19 (1H, s), 7.29 (1H, dd, J=8.54, 5.12 Hz), 7.38 (1H, s), 7.47 (1H, d, J=2.44 Hz), 7.61 (1H, s), 8.41 (1H, d, J=5.37 Hz)

Mass spectrometric value (ESI-MS, m/z): 492 (M+1)

$[\alpha]_D^{25}$ −35.5 (c0.5, CHCl$_3$)

Example 24

N-{4-[(6,7-Dimethoxy-4-quinolyl)oxy]-3-methoxyphenyl}-N'-[(1R)-1-(4-fluorophenyl)ethyl]urea 4-[(6,7-Dimethoxy-4-quinolyl)oxy]-3-methoxyaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (44 mg, yield 97%).

$^1$H-NMR (CDCl$_3$): 1.48 (3H, d, J=6.83 Hz), 3.71 (3H, s), 4.00 (3H, s), 4.04 (3H, s), 5.00 (1H, m), 5.48 (1H, d, J=7.32 Hz), 6.29 (1H, d, J=5.37 Hz), 6.62 (1H, dd, J=8.54, 2.44 Hz), 6.99 (3H, overlapped), 7.19 (1H, s), 7.29 (1H, dd, J=8.54, 5.12 Hz), 7.38 (1H, s), 7.47 (1H, d, J=2.44 Hz), 7.61 (1H, s), 8.41 (1H, d, J=5.37 Hz)

Mass spectrometric value (ESI-MS, m/z): 492 (M$^+$+1)

$[\alpha]_D^{25}$ +35.8° (c0.5, CHCl$_3$)

Example 25

N-{4-[(6,7-Dimethoxy-4-quinolyl)oxy]-2,3-dimethylphenyl}-N'-[1-(4-fluorophenyl)ethyl]urea 4-[(6,7-Dimethoxy-4-quinolyl)oxy]-2,3-dimethylaniline (81 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of 1-(4-fluorophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (6 mg, yield 5%).

$^1$H-NMR (CDCl$_3$): 1.48 (3H, d, J=6.83 Hz), 2.11 (3H, s), 2.16 (3H, s), 4.06 (6H, s), 4.78 (1H, d, J=5.86 Hz), 5.00 (1H, m), 5.97 (1H, s), 6.26 (1H, d, J=5.37 Hz), 6.90-7.25 (5H, overlapped), 7.30 (2H, m), 7.46 (1H, s), 7.59 (1H, s), 8.44 (1H, d, J=5.37 Hz)

Mass spectrometric value (ESI-MS, m/z): 488 (M−1)

Example 26

N-{4-[(6,7-Dimethoxy-4-quinolyl)oxy]-2,3-dimethylphenyl}-N'-[(1S)-1-(4-fluorophenyl)ethyl]urea 4-[(6,7-Dimethoxy-4-quinolyl)oxy]-2,3-dimethylaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. A solution of (1S)-1-(4-fluorophenyl)ethylamine (35 mg) in chloroform (0.2 ml) was then added to the solution, and the mixture was stirred at room temperature for 10 hr. The stirred mixture was purified by chromatography on silica gel using chloroform/methanol for development to give the title compound (34 mg, yield 76%).

$^1$H-NMR (CDCl$_3$): 1.48 (3H, d, J=6.83 Hz), 2.11 (3H, s), 2.16 (3H, s), 4.06 (6H, s), 4.78 (1H, d, J=5.86 Hz), 5.00 (1H, m), 5.97 (1H, s), 6.26 (1H, d, J=5.37 Hz), 6.90-7.25 (5H, overlapped), 7.30 (2H, m), 7.46 (1H, s), 7.59 (1H, s), 8.44 (1H, d, J=5.37 Hz)

Mass spectrometric value (ESI-MS, m/z): 488 (M−1)

$[\alpha]_D^{25}$+30.0° (c0.5, CHCl$_3$)

Example 27

N-{4-[(6,7-Dimethoxy-4-qui nolyl)oxy]-2,3-dimethylphenyl}-N'-[(1R)-1-(4-fluorophenyl)ethyl]urea 4-[(6,7-Dimethoxy-4-quinolyl)oxy]-2,3-dimethylaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (37 mg, yield 81%).

$^1$H-NMR (CDCl$_3$): 1.48 (3H, d, J=6.83 Hz), 2.12 (3H, s), 2.16 (3H, s), 4.05 (3H, s), 4.05 (3H, s), 4.77 (1H, d, J=7.32 Hz), 4.98-5.04 (1H, m), 5.99 (1H, s), 6.25 (1H, d, J=5.37 Hz), 6.99 (1H, d, J=8.78 Hz), 7.04 (2H, dd, J=8.78, 8.78 Hz), 7.31 (2H, dd, J=5.12, 8.78 Hz), 7.43 (1H, s), 7.59 (1H, s), 8.44 (1H, d, J=5.12 Hz)

Mass spectrometric value (ESI-MS, m/z): 488 (M−1)

$[\alpha]_D^{24}$−35.6° (c0.5, CHCl$_3$)

Example 28

N-{4-[(6,7-Dimethoxy-4-quinolyl)oxy]-2-fluorophenyl}-N'-[1-(4-fluorophenyl)ethyl]urea 4-[(6,7-Dimethoxy-4-quinolyl)oxy]-2-fluoroaniline (79 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of 1-(4-fluorophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (39 mg, yield 33%).

$^1$H-NMR (CDCl$_3$): 1.50 (3H, d, J=6.83 Hz), 4.03 (6H, s), 4.97 (1H, m), 5.55 (1H, d, J=6.59 Hz), 6.46 (1H, d, J=5.37 Hz), 6.87-6.96 (3H, overlapped), 7.01 (1H, dd, J=8.78, 8.78 Hz), 7.33 (2H, dd, J=8.54, 5.37 Hz), 7.42 (1H, s), 7.50 (1H, s), 8.17 (1H, dd, J=9.03, 9.03 Hz), 8.48 (1H, d, J=5.37 Hz)

Mass spectrometric value (ESI-MS, m/z): 478 (M−1)

Example 29

N-{4-[(6,7-Dimethoxy-4-quinolyl)oxy]-2-fluorophenyl}-N'-[(1S)-1-(4-fluorophenyl)ethyl]urea 4-[(6,7-Dimethoxy-4-quinolyl)oxy]-2-fluoroaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (35 mg, yield 76%).

$^1$H-NMR (CDCl$_3$): 1.50 (3H, d, J=6.83 Hz), 4.03 (6H, s), 4.97 (1H, m), 5.55 (1H, d, J=6.59 Hz), 6.46 (1H, d, J=5.37 Hz), 6.87-6.96 (3H, overlapped), 7.01 (1H, dd, J=8.78, 8.78 Hz), 7.33 (2H, dd, J=8.54, 5.37 Hz), 7.42 (1H, s), 7.50 (1H, s), 8.17 (1H, dd, J=9.03, 9.03 Hz), 8.48 (1H, d, J=5.37 Hz)

Mass spectrometric value (ESI-MS, m/z): 480 (M$^+$+1)

$[\alpha]_D^{24}$−45.8° (c0.5, CHCl$_3$)

Example 30

N-{4-[(6,7-Dimethoxy-4-quinolyl)oxy]-2-fluorophenyl}-N'-[(1R)-1-(4-fluorophenyl)ethyl]urea 4-[(6,7-Dimethoxy-4-quinolyl)oxy]-2-fluoroaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (34 mg, yield 74%).

$^1$H-NMR (CDCl$_3$): 1.50 (3H, d, J=6.83 Hz), 4.03 (6H, s), 4.97 (1H, m), 5.55 (1H, d, J=6.59 Hz), 6.46 (1H, d, J=5.37 Hz), 6.87-6.96 (3H, overlapped), 7.01 (1H, dd, J=8.78, 8.78 Hz), 7.33 (2H, dd, J=8.54, 5.37 Hz), 7.42 (1H, s), 7.50 (1H, s), 8.17 (1H, dd, J=9.03, 9.03 Hz), 8.48 (1H, d, J=5.37 Hz)

Mass spectrometric value (ESI-MS, m/z): 480 (M$^+$+1)

$[\alpha]_D^{25}$+45.0° (c0.5, CHCl$_3$)

Example 31

N-{4-[(6,7-Dimethoxy-4-quinolyl)oxy]-3-fluorophenyl}-N'-[1-(4-fluorophenyl)ethyl]urea 4-[(6,7-Dimethoxy-4-quinolyl)oxy]-3-fluoroaniline (79 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of 1-(4-fluorophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (55 mg, yield 46%).

$^1$H-NMR (CDCl$_3$): 1.48 (3H, d, J=6.83 Hz), 4.00 (3H, s), 4.05 (3H, s), 4.98 (1H, m), 5.55 (1H, d, J=7.08 Hz), 6.37 (1H, d, J=5.37 Hz), 7.00 (2H, dd, J=8.54, 8.54 Hz), 7.00 (1H, overlapped), 7.10 (1H, dd, J=8.78, 8.78 Hz), 7.28 (2H, dd, J=8.54, 5.37 Hz), 7.33 (1H, s), 7.38 (1H, s), 7.46 (1H, dd, J=12.18, 2.44 Hz), 7.58 (1H, s), 8.44 (1H, d, J=5.37 Hz)

Mass spectrometric value (ESI-MS, m/z): 478 (M−1)

Example 32

N-{4-[(6,7-Dimethoxy-4-quinolyl)oxy]-3-fluorophenyl}-N'-[(1S)-1-(4-fluorophenyl)ethyl]urea 4-[(6,7-Dimethoxy-4-quinolyl)oxy]-3-fluoroaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (27 mg, yield 59%).

$^1$H-NMR (CDCl$_3$): 1.48 (3H, d, J=6.83 Hz), 4.00 (3H, s), 4.05 (3H, s), 4.98 (1H, m), 5.55 (1H, d, J=7.08 Hz), 6.37 (1H, d, J=5.37 Hz), 7.00 (2H, dd, J=8.54, 8.54 Hz), 7.00 (1H, overlapped), 7.10 (1H, dd, J=8.78, 8.78 Hz), 7.28 (2H, dd, J=8.54, 5.37 Hz), 7.33 (1H, s), 7.38 (1H, s), 7.46 (1H, dd, J=12.18, 2.44 Hz), 7.58 (1H, s), 8.44 (1H, d, J=5.37 Hz)

Mass spectrometric value (ESI-MS, m/z): 480 (M$^+$+1)

$[\alpha]_D^{24}$−45.4° (c0.5, CHCl$_3$)

Example 33

N-{4-[(6,7-Dimethoxy-4-quinolyl)oxy]-3-fluorophenyl}-N'-[(1R)-1-(4-fluorophenyl)ethyl]urea 4-[(6,7-Dimethoxy-4-quinolyl)oxy]-3-fluoroaniline (30 is mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(4-fluorophenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (30 mg, yield 66%).

$^1$H-NMR (CDCl$_3$): 1.48 (3H, d, J=6.83 Hz), 4.00 (3H, s), 4.05 (3H, s), 4.98 (1H, m), 5.55 (1H, d, J=7.08 Hz), 6.37 (1H, d, J=5.37 Hz), 7.00 (2H, dd, J=8.54, 8.54 Hz), 7.00 (1H, overlapped), 7.10 (1H, dd, J=8.78, 8.78 Hz), 7.28 (2H, dd, J=8.54, 5.37 Hz), 7.33 (1H, s), 7.38 (1H, s), 7.46 (1H, dd, J=12.18, 2.44 Hz), 7.58 (1H, s), 8.44 (1H, d, J=5.37 Hz)

Mass spectrometric value (ESI-MS, m/z): 480 (M$^+$+1)

$[\alpha]_D^{25}$+44.7° (c0.5, CHCl$_3$)

Example 34

N-[(1S)-1-(4-Bromophenyl)ethyl]-N'-{4-[(6,7-dimethoxy-4-quinolyl)oxy]phenyl}urea 4-[(6,7-Dimethoxy-4-quinolyl)oxy]aniline (70 mg) was dissolved in chloroform (1 ml) and triethylamine (0.1 ml) to prepare a solution. A solution of triphosgene (33 mg) in chloroform (0.2 ml) was then added to the solution, and the mixture was stirred stirred at room temperature for 75 min. Next, a solution of (1S)-1-(4-bromophenyl)ethylamine (46 mg) in chloroform (0.2 ml) was added thereto, and the mixture was stirred at room temperature for 10 hr. The stirred mixture was purified by chromatography on silica gel using chloroform/methanol for development to give the title compound (68 mg, yield 55%).

$^1$H-NMR (CDCl$_3$): 1.45 (3H, d, J=7.07 Hz), 4.02 (3H, s), 4.04 (3H, s), 4.95 (1H, m), 5.37 (1H, d, J=7.32 Hz), 6.42 (1H, d, J=5.36 Hz), 7.00 (1H, s), 7.08 (2H, dd, J=8.78 Hz), 7.20 (2H, d, J=8.29 Hz), 7.37 (2H, dd, J=8.78 Hz), 7.39 (1H, s), 7.44 (2H, d, J=8.29 Hz), 7.55 (1H, s), 8.45 (1H, d, J=5.36 Hz)

Mass spectrometric value (ESI-MS, m/z): 520, 522 (M−1)

$[\alpha]_D^{25}$−33.0° (c0.5, CHCl$_3$)

Example 35

N-{4-[(6,7-Dimethoxy-4-quinolyl)oxy]phenyl}-N'-[(1S)-1-(4-nitrophenyl)ethyl]urea 4-[(6,7-Dimethoxy-4-quinolyl)oxy]aniline (70 mg) was dissolved in chloroform (1 ml) and triethylamine (0.14 ml) to prepare a solution. A solution of triphosgene (33 mg) in chloroform (0.2 ml) was then added to the solution, and the mixture was stirred at room temperature for 75 min. Next, a solution of (1S)-1-(4-nitrophenyl)ethylamine hydrochloride (47 mg) in chloroform (0.2 ml) was added thereto, and the mixture was stirred at room temperature for 10 hr. The stirred mixture was purified by chromatography on silica gel using chloroform/methanol for development to give the title compound (69 mg, yield 60%).

$^1$H-NMR (CDCl$_3$): 1.52 (3H, d, J=7.07 Hz), 4.03 (3H, s), 4.04 (3H, s), 5.11 (1H, m), 5.26 (1H, d, J=6.83 Hz), 6.43 (1H, d, J=5.36 Hz), 6.81 (1H, s), 7.12 (2H, d, J=8.78 Hz), 7.40 (2H, d, J=8.78 Hz), 7.41 (1H, s), 7.51 (2H, d, J=8.78 Hz), 7.55 (1H, s), 8.19 (2H, d, J=8.78 Hz), 8.46 (1H, d, J=5.36 Hz)

Mass spectrometric value (ESI-MS, m/z): 487 (M−1)

$[\alpha]_D^{25}$−27.0° (c0.25, CHCl$_3$)

Example 36

N-{4-[(6,7-Dimethoxy-4-quinolyl)oxy]phenyl}-N'-[(1R)-1-(4-nitrophenyl)ethyl]urea 4-[(6,7-Dimethoxy-4-quinolyl)oxy]aniline (70 mg) was dissolved in chloroform (1 ml) and triethylamine (0.14 ml) to prepare a solution. A solution of triphosgene (33 mg) in chloroform (0.2 ml) was then added to the solution, and the mixture was stirred at room temperature for 75 min. Next, a solution of (1R)-1-(4-nitrophenyl)ethylamine hydrochloride (47 mg) in chloroform (0.2 ml) was added thereto, and the mixture was stirred at room temperature for 10 hr. The stirred mixture was purified by chromatography on silica gel using chloroform/methanol for development to give the title is compound (16 mg, yield 13%).

$^1$H-NMR (CDCl$_3$): 1.52 (3H, d, J=7.07 Hz), 4.03 (3H, s), 4.04 (3H, s), 5.11 (1H, m), 5.24 (1H, d, J=6.83 Hz), 6.43 (1H, d, J=5.36 Hz), 6.76 (1H, s), 7.12 (2H, d, J=8.78 Hz), 7.40 (2H, d, J=8.78 Hz), 7.41 (1H, s), 7.51 (2H, d, J=8.78 Hz), 7.55 (1H, s), 8.19 (2H, d, J=8.78 Hz), 8.46 (1H, d, J=5.36 Hz)

Mass spectrometric value (ESI-MS, m/z): 487 (M−1)

$[\alpha]_D^{25}$+28.0° (c0.5, CHCl$_3$)

Example 37

N-{4-[(6,7-Dimethoxy-4-quinolyl)oxy]phenyl}-N'-[(1S)-1-phenylpropyl]urea

4-[(6,7-Dimethoxy-4-quinolyl)oxy]aniline (70 mg) was dissolved in chloroform (1 ml) and triethylamine (0.1 ml) to prepare a solution. A solution of triphosgene (33 mg) in chloroform (0.2 ml) was then added to the solution, and the mixture was stirred at room temperature for 75 min. Next, a solution of (1S)-1-phenylpropylamine (31 mg) in chloroform (0.2 ml) was added thereto, and the mixture was stirred at room temperature for 10 hr. The stirred mixture was purified by chromatography on silica gel using chloroform/methanol for development to give the title compound (62 mg, yield 57%).

$^1$H-NMR (CDCl$_3$): 0.91 (3H, d, J=7.56 Hz), 1.82 (2H, m), 4.02 (3H, s), 4.03 (3H, s), 4.71 (1H, m), 5.32 (1H, d, J=7.08 Hz), 6.41 (1H, d, J=5.37 Hz), 6.87 (1H, s), 7.07 (2H, d, J=9.02 Hz), 7.28-7.36 (8H, overlapped), 7.40 (1H, s), 7.54 (1H, s), 8.45 (1H, d, J=5.37 Hz)

Mass spectrometric value (ESI-MS, m/z): 456 (M−1)

$[\alpha]_D^{25}$−34.7° (c0.25, CHCl$_3$)

Example 38

N-{4-[(6,7-Dimethoxy-4-quinolyl)oxy]phenyl}-N'-[(1R)-1-phenylpropyl]urea

4-[(6,7-Dimethoxy-4-quinolyl)oxy]aniline (70 mg) was dissolved in chloroform (1 ml) and triethylamine (0.1 ml) to prepare a solution. A solution of triphosgene (33 mg) in chloroform (0.2 ml) was then added to the solution, and the mixture was stirred at room temperature for 75 min. Next, a solution of (1R)-1-phenylpropylamine (31 mg) in chloroform (0.2 ml) was added thereto, and the mixture was stirred at room temperature for 10 hr. The stirred mixture was purified by chromatography on silica gel using chloroform/methanol for development to give the title compound (75 mg, yield 69%).

$^1$H-NMR (CDCl$_3$): 0.93 (3H, d, J=7.56 Hz), 1.84 (2H, m), 4.03 (3H, s), 4.04 (3H, s), 4.70 (1H, m), 5.09 (1H, d, J=7.08 Hz), 6.42 (1H, d, J=5.37 Hz), 6.54 (1H, s), 7.08 (2H, d, J=9.03 Hz), 7.29-7.38 (8H, overlapped), 7.41 (1H, s), 7.54 (1H, s), 8.45 (1H, d, J=5.37 Hz)

Mass spectrometric value (ESI-MS, m/z): 456 (M−1)

$[\alpha]_D^{25}$+34.4° (c0.5, CHCl$_3$)

Example 41

N-{4-[(6,7-Dimethoxy-4-quinolyl)oxy]phenyl}-N'-[(1S)-1-(4-methylphenyl)ethyl]urea 4-[(6,7-Dimethoxy-4-quinolyl)oxy]aniline (70 mg) was dissolved in chloroform (1 ml) and triethylamine (0.1 ml) to prepare a solution. A solution of triphosgene (33 mg) in chloroform (0.2 ml) was then added to the solution, and the mixture was stirred at room temperature for 75 min. Next, a solution of (1S)-1-(4-methylphenyl)ethylamine (31 mg) in chloroform (0.2 ml) was added thereto, and the mixture was stirred at room temperature for 10 hr. The stirred mixture was purified by chromatography on silica gel using chloroform/methanol for development to give the title compound (52 mg, yield 48%).

$^1$H-NMR (CDCl$_3$): 1.49 (3H, d, J=6.83 Hz), 2.33 (3H, s), 4.02 (3H, s), 4.03 (3H, s), 4.53 (1H, m), 5.15 (1H, d, J=6.83 Hz), 6.41 (1H, d, J=5.37 Hz), 6.68 (1H, s), 7.07 (2H, d, J=8.78 Hz), 7.15 (2H, d, J=7.81 Hz), 7.24 (2H, d, J=7.81 Hz), 7.35 (2H, d, J=8.78 Hz), 7.40 (1H, s), 7.54 (1H, s), 8.45 (1H, d, J=5.37 Hz)

Mass spectrometric value (ESI-MS, m/z): 456 (M−1)

$[\alpha]_D^{24}$−32.0° (c0.5, CHCl$_3$)

Example 42

N-{4-[(6,7-Dimethoxy-4-quinolyl)oxy]phenyl}-N'-[(1R)-1-(4-methylphenyl)ethyl]urea 4-[(6,7-Dimethoxy-4-quinolyl)oxy]aniline (70 mg) was dissolved in chloroform (1 ml) and triethylamine (0.1 ml) to is prepare a solution. A solution of triphosgene (33 mg) in chloroform (0.2 ml) was then added to the solution, and the mixture was stirred at room temperature for 75 min. Next, a solution of (1R)-1-(4-methylphenyl)ethylamine (31 mg) in chloroform (0.2 ml) was added thereto, and the mixture was stirred at room temperature for 10 hr. The stirred mixture was purified by chromatography on silica gel using chloroform/methanol for development to give the title compound (68 mg, yield 63%).

$^1$H-NMR (CDCl$_3$): 1.49 (3H, d, J=6.83 Hz), 2.33 (3H, s), 4.02 (3H, s), 4.03 (3H, s), 4.93 (1H, m), 5.18 (1H, d, J=7.07 Hz), 6.41 (1H, d, J=5.37 Hz), 6.72 (1H, s), 7.07 (2H, d, J=8.78 Hz), 7.15 (2H, d, J=8.05 Hz), 7.24 (2H, d, J=8.05 Hz), 7.35 (2H, d, J=8.78 Hz), 7.40 (1H, s), 7.54 (1H, s), 8.45 (1H, d, J=5.37 Hz)

Mass spectrometric value (ESI-MS, m/z): 456 (M−1)

$[\alpha]_D^{24}$+31.7° (c0.5, CHCl$_3$)

Example 43

N-[(1S)-2,3-Dihydro-1H-1-indenyl]-N'-{4-[(6,7-dimethoxy-4-quinolyl)oxy]phenyl}urea 4-[(6,7-Dimethoxy-4-quinolyl)oxy]aniline (70 mg) was dissolved in chloroform (1 ml) and triethylamine (0.1 ml) to prepare a solution. A solution of triphosgene (33 mg) in chloroform (0.2 ml) was then added to the solution, and the mixture was stirred at room temperature for 75 min. Next, a solution of (S)-1-aminoindane (31 mg) in chloroform (0.2 ml)

was added thereto, and the mixture was stirred at room temperature for 10 hr. The stirred mixture was purified by chromatography on silica gel using chloroform/methanol for development to give the title compound (43 mg, yield 40%).

$^1$H-NMR (CDCl$_3$+CD$_3$OD): 1.83 (1H, m), 2.64 (1H, m), 2.89 (1H, m), 2.99 (1H, m), 4.06 (3H, s), 4.07 (3H, s), 5.38 (1H, t, J=7.32 Hz), 6.47 (1H, d, J=5.37 Hz), 7.11 (2H, d, J=8.54 Hz), 7.23 (3H, overlapped), 7.37 (2H, overlapped), 7.52 (2H, d, J=8.54 Hz), 7.59 (1H, s), 8.40 (1H, d, J=5.37 Hz)

Mass spectrometric value (ESI-MS, m/z): 454 (M−1)

$[\alpha]_D^{24}$+10.0° (c0.5, CHCl$_3$)

Example 44

N-[(1R)-2,3-Dihydro-1H-1-indenyl]-N'-{4-[(6,7-dimethoxy-4-quinolyl)oxy]phenyl}urea 4-[(6,7-Dimethoxy-4-quinolyl)oxy]aniline (70 mg) was dissolved in chloroform (1 ml) and triethylamine (0.1 ml) to prepare a solution. A solution of triphosgene (33 mg) in chloroform (0.2 ml) was then added to the solution, and the mixture was stirred at room temperature for 75 min. Next, a solution of (R)-1-aminoindane (31 mg) in chloroform (0.2 ml) was added thereto, and the mixture was stirred at room temperature for 10 hr. The stirred mixture was purified by chromatography on silica gel using chloroform/methanol for development to give the title compound (35 mg, yield 32%).

$^1$H-NMR (CDCl$_3$): 1.81 (1H, m), 2.63 (1H, m), 2.87 (1H, m), 2.97 (1H, m), 4.05 (6H, s), 5.39 (1H, t, J=7.56 Hz), 6.44 (1H, d, J=5.37 Hz), 7.10 (2H, d, J=8.78 Hz), 7.23 (3H, overlapped), 7.36 (1H, brd, J=6.83 Hz), 7.38 (1H, s), 7.57 (1H, s), 8.41 (1H, d, J=5.37 Hz)

Mass spectrometric value (ESI-MS, m/z): 454 (M−1)

$[\alpha]_D^{24}$90.5° (c0.25, CHCl$_3$)

Example 45

N-[(1R)-1-(3-Bromophenyl)ethyl]-N'-{4-[(6,7-dimethoxy-4-quinolyl)oxy]phenyl}urea 4-[(6,7-Dimethoxy-4-quinolyl)oxy]aniline (70 mg) was dissolved in chloroform (1 ml) and triethylamine (0.14 ml) to prepare a solution. A solution of triphosgene (33 mg) in chloroform (0.2 ml) was then added to the solution, and the mixture was stirred at room temperature for 75 min. Next, a solution of (1R)-1-(3-bromophenyl)ethylamine hydrochloride (54 mg) in chloroform (0.2 ml) was added thereto, and the mixture was stirred at room temperature for 10 hr. The stirred mixture was purified by chromatography on silica gel using chloroform/methanol for development to give the title compound (70 mg, yield 57%).

$^1$H-NMR (CDCl$_3$): 1.43 (3H, d, J=6.83 Hz), 4.01 (3H, s), 4.03 (3H, s), 4.97 (1H, m), 5.72 (1H, d, J=7.32 Hz), 6.41 (1H, d, J=5.37 Hz), 7.07 (2H, d, J=8.78 Hz), 7.16 (1H, t, J=7.81 Hz), 7.24 (1H, d, J=7.81 Hz), 7.25-7.40 (3H, overlapped), 7.44 (2H, overlapped), 7.55 (1H, s), 8.44 (1H, d, J=5.37 Hz)

Mass spectrometric value (ESI-MS, m/z): 520, 522 (M−1)

$[\alpha]_D^{24}$+34.3° (c0.5, CHCl$_3$)

Example 46

N-[(1S)-1-(3-Bromophenyl)ethyl]-N'-{4-[(6,7-dimethoxy-4-quinolyl)oxy]phenyl}urea 4-[(6,7-Dimethoxy-4-quinolyl)oxy]aniline (70 mg) was dissolved in chloroform (1 ml) and triethylamine (0.14 ml) to prepare a solution. A solution of triphosgene (33 mg) in chloroform (0.2 ml) was then added to the solution, and the mixture was stirred at room temperature for 75 min. Next, a solution of (1S)-1-(3-bromophenyl)ethylamine hydrochloride (54 mg) in chloroform (0.2 ml) was added thereto, and the mixture was stirred at room temperature for 10 hr. The stirred mixture was purified by chromatography on silica gel using chloroform/methanol for development to give the title compound (76 mg, yield 62%).

$^1$H-NMR (CDCl$_3$): 1.46 (3H, d, J=6.83 Hz), 4.02 (3H, s), 4.04 (3H, s), 4.98 (1H, m), 5.38 (1H, d, J=7.32 Hz), 6.42 (1H, d, J=5.37 Hz), 6.69 (1H, s), 7.09 (2H, d, J=9.03 Hz), 7.19 (1H, t, J=7.81 Hz), 7.26 (1H, overlapped with CHCl$_3$), 7.37-7.40 (4H, overlapped), 7.47 (1H, s), 7.55 (1H, s), 8.45 (1H, d, J=5.37 Hz)

Mass spectrometric value (ESI-MS, m/z): 520, 522 (M−1)

$[\alpha]_D^{24}$−33.5° (c0.5, CHCl$_3$)

Example 47

N-[(1S)-1-(4-Chlorophenyl)ethyl]-N'-{4-[(6,7-dimethoxy-4-quinolyl)oxy]phenyl}urea 4-[(6,7-Dimethoxy-4-quinolyl)oxy]aniline (70 mg) was dissolved in chloroform (1 ml) and triethylamine (0.1 ml) to prepare a solution. A solution of triphosgene (33 mg) in chloroform (0.2 ml) was then added to the solution, and the mixture was stirred at room temperature for 75 min. Next, a solution of (1S)-1-(4-chlorophenyl)ethylamine (36 mg) in chloroform (0.2 ml) was added thereto, and the mixture was stirred at room temperature for 10 hr. The stirred mixture was purified by chromatography on silica gel using chloroform/methanol for development to give the title compound (61 mg, yield 54%).

$^1$H-NMR (CDCl$_3$+CD$_3$OD): 1.47 (3H, d, J=6.83 Hz), 4.05 (3H, s), 4.06 (3H, s), 4.95 (1H, q, J=6.83 Hz), 6.44 (1H, d, J=5.37 Hz), 7.08 (2H, d, J=8.78 Hz), 7.31 (4H, singlet like, overlapped), 7.36 (1H, s), 7.47 (2H, d, J=8.78 Hz), 7.58 (1H, s), 8.37 (1H, d, J=5.37 Hz)

Mass spectrometric value (ESI-MS, m/z): 476 (M−1)

$[\alpha]_D^{24}$−30.3° (c0.5, CHCl$_3$)

Example 48

N-[(1R)-1-(4-Chlorophenyl)ethyl]-N'-{4-[(6,7-dimethoxy-4-quinolyl)oxy]phenyl}urea 4-[(6,7-Dimethoxy-4-quinolyl)oxy]aniline (70 mg) was dissolved in chloroform (1 ml) and triethylamine (0.1 ml) to prepare a solution. A solution of triphosgene (33 mg) in chloroform (0.2 ml) was then added to the solution, and the mixture was stirred at room temperature for 75 min. Next, a solution of (1R)-1-(4-chlorophenyl)ethylamine (36 mg) in chloroform (0.2 ml) was added thereto, and the mixture was stirred at room temperature for 10 hr. The stirred mixture was purified by chromatography on silica gel using chloroform/methanol for development to give the title compound (70 mg, yield 62%).

$^1$H-NMR (CDCl$_3$): 1.46 (3H, d, J=6.83 Hz), 4.03 (3H, s), 4.04 (3H, s), 4.96 (1H, q, J=6.83 Hz), 6.41 (1H, d, J=5.37 Hz), 7.06 (2H, d, J=9.03 Hz), 7.28 (4H, doublet like, overlapped), 7.37 (1H, s), 7.42 (2H, d, J=9.03 Hz), 7.56 (1H, s), 8.40 (1H, d, J=5.37 Hz)

Mass spectrometric value (ESI-MS, m/z): 476 (M−1)

$[\alpha]_D^{24}$+30.3° (c0.5, CHCl$_3$)

Example 49

N-{4-[(6,7-Dimethoxy-4-quinolyl)oxy]phenyl}-N'-
[(1S)-1-(3-methoxyphenyl)ethyl]urea 4-[(6,7-Dimethoxy-4-quinolyl)oxy]aniline (70 mg) was dissolved in chloroform (1 ml) and triethylamine (0.1 ml) to prepare a solution. A solution of triphosgene (33 mg) in chloroform (0.2 ml) was then added to the solution, and the mixture was stirred at room temperature for 75 min. Next, a solution of (1S)-1-(3-methoxyphenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (67 mg, yield 60%).

$^1$H-NMR (CDCl$_3$): 1.47 (3H, d, J=6.83 Hz), 3.79 (3H, s), 4.04 (6H, s), 4.95 (1H, q, J=6.83 Hz), 6.41 (1H, d, J=5.37 Hz), 6.79 (1H, dd, J=7.81, 2.20 Hz), 6.90 (1H, d, J=2.20 Hz), 6.94 (1H, d, J=7.81 Hz), 7.06 (2H, d, J=8.78 Hz), 7.25 (1H, t, J=7.81 Hz), 7.38 (1H, s), 7.41 (2H, d, J=8.78 Hz), 7.56 (1H, s), 8.40 (1H, d, J=5.37 Hz)

Mass spectrometric value (ESI-MS, m/z): 472 (M−1)
$[\alpha]_D^{24}$−25.2° (c0.5, CHCl$_3$)

Example 50

N-{4-[(6,7-Dimethoxy-4-quinolyl)oxy]phenyl}-N'-
[(1R)-1-(3-methoxyphenyl)ethyl]urea 4-[(6,7-Dimethoxy-4-quinolyl)oxy]aniline (70 mg) was dissolved in chloroform (1 ml) and triethylamine (0.1 ml) to prepare a solution. A solution of triphosgene (33 mg) in chloroform (0.2 ml) was then added to the solution, and the mixture was stirred at room temperature for 75 min. Next, a solution of (1R)-1-(3-methoxyphenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (53 mg, yield 47%).

$^1$H-NMR (CDCl$_3$): 1.46 (3H, d, J=6.83 Hz), 3.75 (3H, s), 4.00 (3H, s), 4.03 (3H, s), 4.95 (1H, m), 5.59 (1H, d, J=7.07 Hz), 6.40 (1H, d, J=5.37 Hz), 6.77 (1H, dd, J=7.81, 2.20 Hz), 6.88 (1H, d, J=2.20 Hz), 6.91 (1H, d, J=7.81 Hz), 7.05 (2H, d, J=8.78 Hz), 7.23 (1H, t, J=7.81 Hz), 7.28 (1H, s), 7.36 (2H, d, J=8.78 Hz), 7.39 (1H, s), 7.54 (1H, s), 8.43 (1H, d, J=5.37 Hz)

Mass spectrometric value (ESI-MS, m/z): 472 (M−1)
$[\alpha]_D^{24}$+25.8° (c0.5, CHCl$_3$)

Example 51

N-{4-[(6,7-Dimethoxy-4-quinolyl)oxy]phenyl}-N'-
[(1S)-1-(2-methoxyphenyl)ethyl]urea 4-[(6,7-Dimethoxy-4-quinolyl)oxy]aniline (70 mg) was dissolved in chloroform (1 ml) and triethylamine (0.1 ml) to prepare a solution. A solution of triphosgene (33 mg) in chloroform (0.2 ml) was then added to the solution, and the mixture was stirred at room temperature for 75 min. Next, a solution of (1S)-1-(2-methoxyphenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (67 mg, yield 59%).

$^1$H-NMR (CDCl$_3$): 1.49 (3H, d, J=6.83 Hz), 3.81 (3H, s), 4.01 (3H, s), 4.04 (3H, s), 5.19 (1H, m), 5.74 (1H, br), 6.42 (1H, d, J=5.37 Hz), 6.90 (1H, d, J=7.81 Hz), 6.94 (1H, t, J=6.59 Hz), 7.08 (2H, d, J=8.78 Hz), 7.22-7.29 (2H, overlapped), 7.38 (2H, d, J=8.78 Hz), 7.40 (1H, s), 7.55 (1H, s), 8.46 (1H, d, J=5.37 Hz)

Mass spectrometric value (ESI-MS, m/z): 472 (M−1)
$[\alpha]_D^{24}$−17.7° (c0.5, CHCl$_3$)

Example 52

N-{4-[(6,7-Dimethoxy-4-quinolyl)oxy]phenyl}-N'-
[(1R)-1-(2-methoxyphenyl)ethyl]urea 4-[(6,7-Dimethoxy-4-quinolyl)oxy]aniline (70 mg) was dissolved in chloroform (1 ml) and triethylamine (0.1 ml) to prepare a solution. A solution of triphosgene (33 mg) in chloroform (0.2 ml) was then added to the solution, and the mixture was stirred at room temperature for 75 min. Next, a solution of (1R)-1-(2-methoxyphenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (64 mg, yield 57%).

$^1$H-NMR (CDCl$_3$): 1.48 (3H, d, J=6.83 Hz), 3.76 (3H, s), 4.00 (3H, s), 4.04 (3H, s), 5.20 (1H, m), 5.86 (1H, br), 6.42 (1H, d, J=5.37 Hz), 6.87 (1H, d, J=8.29 Hz), 6.92 (1H, t, J=7.32 Hz), 7.07 (2H, d, J=9.03 Hz), 7.22 (1H, t, J=7.32 Hz), 7.26 (1H, overlapped with CHCl$_3$), 7.39 (2H, d, J=9.03 Hz), 7.40 (1H, s), 7.55 (1H, s), 8.43 (1H, d, J=5.37 Hz)

Mass spectrometric value (ESI-MS, m/z): 472 (M−1)
$[\alpha]_D^{24}$+17.8° (c0.5, CHCl$_3$)

Example 53

N-{4-[(6,7-Dimethoxy-4-quinolyl)oxy]phenyl}-N'-
[(1S)-1-(4-methoxyphenyl)ethyl]urea 4-[(6,7-Dimethoxy-4-quinolyl)oxy]aniline (70 mg) was dissolved in chloroform (1 ml) and triethylamine (0.1 ml) to prepare a solution. A solution of triphosgene (33 mg) in chloroform (0.2 ml) was then added to the solution, and the mixture was stirred at room temperature for 75 min. Next, a solution of (1S)-1-(4-methoxyphenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (63 mg, yield 57%).

$^1$H-NMR (CDCl$_3$): 1.48 (3H, d, J=6.83 Hz), 3.78 (3H, s), 4.02 (3H, s), 4.03 (3H, s), 4.92 (1H, m), 5.26 (1H, d, J=6.83 Hz), 6.41 (1H, d, J=5.37 Hz), 6.87 (2H, d, J=8.78 Hz), 6.87 (1H, s), 7.07 (2H, d, J=8.78 Hz), 7.27 (2H, d, J=8.78 Hz), 7.35 (2H, d, J=8.78 Hz), 7.39 (1H, s), 7.54 (1H, s), 8.44 (1H, d, J=5.37 Hz)

Mass spectrometric value (ESI-MS, m/z): 472 (M−1)
$[\alpha]_D^{24}$−33.0° (c0.5, CHCl$_3$)

Example 54

N-{4-[(6,7-Dimethoxy-4-quinolyl)oxy]phenyl}-N'-
[(1R)-1-(4-methoxyphenyl)ethyl]urea 4-[(6,7-Dimethoxy-4-quinolyl)oxy]aniline (70 mg) was dissolved in chloroform (1 ml) and triethylamine (0.1 ml) to prepare a solution. A solution of triphosgene (33 mg) in chloroform (0.2 ml) was then added to the solution, and the mixture was stirred at room temperature for 75 min. Next, a solution of (1R)-1-(4-methoxyphenyl)ethylamine (35 mg) in chloroform (0.2 ml) was added thereto, and the mixture was stirred at room temperature for 10 hr. The stirred mixture was purified by chromatography on silica gel using chloroform/methanol for development to give the title compound (56 mg, yield 50%).

$^1$H-NMR (CDCl$_3$): 1.47 (3H, d, J=6.83 Hz), 3.77 (3H, s), 4.01 (3H, s), 4.03 (3H, s), 4.92 (1H, m), 5.37 (1H, d, J=6.83 Hz), 6.40 (1H, d, J=5.37 Hz), 6.85 (2H, d, J=8.72 Hz), 7.03 (1H, s), 7.06 (2H, d, J=9.03 Hz), 7.25 (2H, d, J=9.03 Hz), 7.35 (2H, d, J=8.78 Hz), 7.39 (1H, s), 7.54 (1H, s), 8.44 (1H, d, J=5.37 Hz)

Mass spectrometric value (ESI-MS, m/z): 472 (M−1)

$[\alpha]_D^{24}$+34.3° (c0.5, CHCl$_3$)

Example 55

N-[(1R)-1-(3-Bromophenyl)ethyl]-N'-{2-chloro-4-[(6,7-dimethoxy-4-quinolyl)oxy]phenyl}urea 2-Chloro-4-[(6,7-dimethoxy-4-quinolyl)oxy]aniline (83 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of (1R)-1-(3-bromophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (64 mg, yield 46%).

$^1$H-NMR (CDCl$_3$): 1.49 (3H, d, J=6.08 Hz), 4.02 (3H, s), 4.03 (3H, s), 4.95 (1H, m), 5.89 (1H, d, J=6.59 Hz), 6.46 (1H, d, J=5.37 Hz), 7.05-7.10 (2H, overlapped), 7.16 (1H, d, J=2.68 Hz), 7.20 (1H, dd, J=7.81, 7.81 Hz), 7.30 (1H, d, J=7.81 Hz), 7.38 (1H, m), 7.41 (1H, s), 7.50 (1H, s), 7.52 (1H, s), 8.27 (1H, d, J=9.03 Hz), 8.48 (1H, d, J=5.37 Hz)

Mass spectrometric value (ESI-MS, m/z): 554, 556 (M−1)

$[\alpha]_D^{24}$+32.3° (c0.5, CHCl$_3$)

Example 56

N-[(1R)-1-(3-Bromophenyl)ethyl]-N'-{4-[(6,7-dimethoxy-4-quinolyl)oxy]-2,5-dimethylphenyl}urea 4-[(6,7-Dimethoxy-4-quinolyl)oxy]-2,5-dimethylaniline (83 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of (1R)-1-(3-bromophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (63 mg, yield 45%).

$^1$H-NMR (CDCl$_3$): 1.47 (3H, d, J=7.08 Hz), 2.12 (3H, s), 2.13 (3H, s), 4.04 (3H, s), 4.05 (3H, s), 4.97 (1H, m), 5.26 (1H, d, J=7.32 Hz), 6.26 (1H, s), 6.29 (1H, d, J=5.37 Hz), 6.92 (1H, s), 7.21 (1H, dd, J=7.81, 7.81 Hz), 7.28 (1H, d, J=7.81 Hz), 7.39 (1H, d, J=7.81 Hz), 7.42 (1H, s), 7.48 (1H, s), 7.54 (1H, s), 7.57 (1H, s), 8.44 (1H, d, J=5.37 Hz)

Mass spectrometric value (ESI-MS, m/z): 548, 550 (M−1)

$[\alpha]_D^{24}$−7.6° (c0.5, CHCl$_3$)

Example 57

N-[(1R)-1-(3-Bromophenyl)ethyl]-N'-{3-chloro-4-[(6,7-dimethoxy-4-quinolyl)oxy]phenyl}urea 3-Chloro-4-[(6,7-dimethoxy-4-quinolyl)oxy]aniline (78 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of (1R)-1-(3-bromophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (41 mg, yield 31%).

$^1$H-NMR (CDCl$_3$): 1.45 (3H, d, J=6.83 Hz), 4.01 (3H, s), 4.05 (3H, s), 4.95 (1H, m), 5.87 (1H, d, J=7.32 Hz), 6.28 (1H, d, J=5.37 Hz), 7.09 (1H, d, J=8.78 Hz), 7.17 (1H, dd, J=7.81, 7.81 Hz), 7.26 (2H, overlapped), 7.35 (1H, d, J=7.81 Hz), 7.40 (1H, s), 7.46 (1H, s), 7.59 (1H, s), 7.62 (1H, d, J=2.44 Hz), 7.67 (1H, s), 8.41 (1H, d, J=5.37 Hz)

Mass spectrometric value (ESI-MS, m/z): 554, 556 (M−1)

$[\alpha]_D^{24}$+43.4° (c0.5, CHCl$_3$)

Example 58

N-[(1R)-1-(3-Bromophenyl)ethyl]-N'-{4-[(6,7-dimethoxy-4-quinolyl)oxy]-2-methylphenyl}urea 4-[(6,7-Dimethoxy-4-quinolyl)oxy]-2-methylaniline (82 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of (1R)-1-(3-bromophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (17 mg, yield 12%).

$^1$H-NMR (CDCl$_3$): 1.47 (3H, d, J=6.83 Hz), 2.17 (3H, s), 4.03 (3H, s), 4.04 (3H, s), 4.96 (1H, m), 5.19 (1H, d, J=7.08 Hz), 6.25 (1H, s), 6.48 (1H, d, J=5.12 Hz), 7.01 (1H, s), 7.03 (1H, overlapped), 7.21 (1H, dd, J=7.81, 7.81 Hz), 7.27 (1H, overlapped), 7.38 (1H, d, J=8.29 Hz), 7.42 (1H, s), 7.48 (1H, s), 7.52 (1H, s), 7.62 (1H, d, J=9.51 Hz), 8.41 (1H, d, J=5.12 Hz)

Mass spectrometric value (ESI-MS, m/z): 534, 536 (M−1)

$[\alpha]_D^{24}$−17.0° (c0.5, CHCl$_3$)

Example 59

N-[(1R)-1-(3-Bromophenyl)ethyl]-N'-{4-[(6,7-dimethoxy-4-quinolyl)oxy]-2-methoxyphenyl}urea 4-[(6,7-Dimethoxy-4-quinolyl)oxy]-2-methoxyaniline (91 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of (1R)-1-(3-bromophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (23 mg, yield 15%).

$^1$H-NMR (CDCl$_3$): 1.51 (3H, d, J=6.83 Hz), 3.76 (3H, s), 4.04 (3H, s), 4.05 (3H, s), 4.94 (1H, m), 5.14 (1H, d, J=6.59 Hz), 6.45 (1H, d, J=5.12 Hz), 6.67 (1H, d, J=2.68 Hz), 6.77 (1H, dd, J=8.78, 2.44 Hz), 6.87 (1H, s), 7.23 (1H, dd, J=7.81, 7.81 Hz), 7.33 (1H, d, J=7.81 Hz), 7.41 (1H, overlapped), 7.42 (1H, s), 7.53 (1H, s), 7.55 (1H, s), 8.16 (1H, d, J=8.73 Hz), 8.46 (1H, d, J=5.12 Hz)

Mass spectrometric value (ESI-MS, m/z): 550, 552 (M−1)

$[\alpha]_D^{24}$+16.2° (c0.5, CHCl$_3$)

Example 60

N-[(1R)-1-(3-Bromophenyl)ethyl]-N'-[4-[(6,7-dimethoxy-4-quinolyl)oxy]-2-(trifluoromethyl)phenyl]urea 4-[(6,7-Dimethoxy-4-quinolyl)oxy]-2-(trifluoromethyl) aniline (82 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of (1R)-1-(3-bromophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (39 mg, yield 29%).

$^1$H-NMR (CDCl$_3$): 1.50 (3H, d, J=7.08 Hz), 4.04 (3H, s), 4.05 (3H, s), 4.94 (1H, m), 5.51 (1H, d, J=6.59 Hz), 6.45 (1H, d, J=5.37 Hz), 6.72 (1H, s), 7.22 (1H, dd, J=7.81, 7.56 Hz), 7.28-7.34 (2H, overlapped), 7.39-7.41 (2H, overlapped), 7.44 (1H, s), 7.50 (2H, s), 8.13 (1H, d, J=9.03 Hz), 8.50 (1H, d, J=5.37 Hz)

Mass spectrometric value (ESI-MS, m/z): 588, 590 (M−1)

$[\alpha]_D^{24}$+42.6° (c0.5, CHCl$_3$)

Example 61

N-[(1R)-1-(3-Bromophenyl)ethyl]-N'-{4-[(6,7-dimethoxy-4-quinolyl)oxy]-3-methoxyphenyl}urea 4-[(6,7-Dimethoxy-4-quinolyl)oxy]-3-methoxyaniline (79 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of (1R)-1-(3-bromophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (39 mg, yield 29%).

$^1$H-NMR (CDCl$_3$): 1.46 (3H, d, J=6.83 Hz), 3.70 (3H, s), 4.01 (3H, s), 4.04 (3H, s), 4.98 (1H, m), 5.76 (1H, d, J=7.32 Hz), 6.30 (1H, d, J=5.37 Hz), 6.67 (1H, dd, J=8.54, 2.44 Hz), 6.99 (1H, d, J=8.54 Hz), 7.17 (1H, dd, J=7.81, 7.56 Hz), 7.27 (1H, overlapped), 7.35 (1H, d, J=8.05 Hz), 7.40 (1H, s), 7.46-7.48 (3H, overlapped), 7.61 (1H, s), 8.39 (1H, d, J=5.37 Hz)

Mass spectrometric value (ESI-MS, m/z): 550, 552 (M−1)

$[\alpha]_D^{24}$−28.0° (c0.5, CHCl$_3$)

Example 62

N-[(1R)-1-(3-Bromophenyl)ethyl]-N'-{4-[(6,7-dimethoxy-4-quinolyl)oxy]-2,3-dimethylphenyl}urea 4-[(6,7-Dimethoxy-4-quinolyl)oxy]-2,3-dimethylaniline (79 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of (1R)-1-(3-bromophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (34 mg, yield 26%).

$^1$H-NMR (CDCl$_3$): 1.46 (3H, d, J=7.07 Hz), 2.11 (3H, s), 2.18 (3H, s), 4.05 (3H, s), 4.06 (3H, s), 4.99 (1H, m), 5.12 (1H, d, J=7.32 Hz), 6.27 (1H, d, J=5.37 Hz), 6.31 (1H, s), 6.99 (1H, d, J=8.72 Hz), 7.20 (1H, dd, J=7.81, 7.81 Hz), 7.27 (1H, overlapped), 7.35-7.39 (2H, overlapped), 7.45 (1H, s), 7.46 (1H, s), 7.59 (1H, s), 8.43 (1H, d, J=5.37 Hz)

Mass spectrometric value (ESI-MS, m/z): 548, 550 (M−1)

$[\alpha]_D^{24}$−31.3° (c0.5, CHCl$_3$)

Example 63

N-[(1R)-1-(3-Bromophenyl)ethyl]-N'-{4-[(6,7-dimethoxy-4-quinolyl)oxy]-2-fluorophenyl}urea 4-[(6,7-Dimethoxy-4-quinolyl)oxy]-2-fluoroaniline (79 mg) was dissolved in chloroform (2 ml) and triethylamine (0.2 ml) to prepare a solution. A solution of triphosgene (70 mg) in chloroform (0.4 ml) was then added to the solution, and the mixture was stirred at room temperature for one hr. Next, a solution of (1R)-1-(3-bromophenyl)ethylamine (70 mg) in chloroform (0.4 ml) was added thereto, and the mixture was stirred at room temperature for 10 hr. The stirred mixture was purified by chromatography on silica gel using chloroform/methanol for development to give the title compound (58 mg, yield 43%).

$^1$H-NMR (CDCl$_3$): 1.48 (3H, d, J=7.07 Hz), 4.02 (3H, s), 4.03 (3H, s), 4.96 (1H, m), 5.76 (1H, d, J=6.83 Hz), 6.47 (1H, d, J=5.37 Hz), 6.89 (1H, dd, J=11.47, 2.44 Hz), 6.94 (1H, dd, J=8.78, 2.44 Hz), 7.05 (1H, brs), 7.19 (1H, dd, J=7.81, 7.81 Hz), 7.28 (1H, d, J=7.81 Hz), 7.37 (1H, ddd, J=7.81, 1.71, 1.22 Hz), 7.42 (1H, s), 7.49 (1H, dd, J=1.71, 1.71 Hz), 7.50 (1H, s), 8.18 (1H, dd, J=9.03, 9.03 Hz), 8.47 (1H, d, J=5.37 Hz)

Mass spectrometric value (ESI-MS, m/z): 538, 540 (M−1)

$[\alpha]_D^{24}$+53.4° (c0.5, CHCl$_3$)

Example 64

N-(3-Fluoro-4-{[6-methoxy-7-(3-morpholinopropoxy)-4-quinolyl]oxy}phenyl)-N'-[1-(4-fluorophenyl)ethyl]urea 3-Fluoro-4-{[6-methoxy-7-(3-morpholinopropoxy)-4-quinolyl]oxy}-aniline (30 mg) was dissolved in chloroform (3 ml) and triethylamine (0.3 ml) to prepare a solution. A solution of triphosgene (17 mg) in chloroform (0.2 ml) was then added to the solution, and the mixture was stirred at room temperature for 25 min. Next, a solution of 1-(4-fluorophenyl)ethylamine (12 mg) in chloroform (0.2 ml) was added thereto, and the mixture was stirred at room temperature for 5 hr. The stirred mixture was purified by chromatography on silica gel using chloroform/methanol for development to give the title compound (22 mg, yield 52%).

¹H-NMR (CDCl₃, 400 MHz): δ 1.50 (d, J=6.8 Hz, 3H), 2.09-2.15 (m, 2H), 2.48 (br, 4H), 2.57 (t, J=7.1 Hz, 2H), 3.71-3.73 (m, 4H), 4.02 (s, 3H), 4.24 (t, J=6.6 Hz, 2H), 4.96-5.00 (m, 1H), 5.28 (br, 1H), 6.37 (d, J=4.4 Hz, 1H), 7.00-7.05 (m, 3H), 7.12 (d, J=8.5 Hz, 1H), 7.32 (dd, J=5.4, 8.5 Hz, 1H), 7.41 (s, 1H), 7.48 (dd, J=2.4, 12.2 Hz, 1H), 7.56 (s, 1H), 8.44 (d, J=5.1 Hz, 1H)

Mass spectrometric value (ESI-MS, m/z): 593 (M⁺+1)

Example 65

N-[1-(3,4-Difluorophenyl)ethyl]-N'-(3-fluoro-4-{[6-methoxy-7-(3-morpholinopropoxy)-4-quinolyl]oxy}phenyl)urea 3-Fluoro-4-{[6-methoxy-7-(3-morpholinopropoxy)-4-quinolyl]oxy}-aniline (30 mg) was dissolved in chloroform (3 ml) and triethylamine (0.3 ml) to prepare a solution. A solution of triphosgene (17 mg) in chloroform (0.2 ml) was then added to the solution, and the mixture was stirred at room temperature for 25 min. Next, a solution of 1-(3,4-difluorophenyl)ethylamine (14 mg) in chloroform (0.2 ml) was added thereto, and the mixture was stirred at room temperature for 5 hr. The stirred mixture was purified by chromatography on silica gel using chloroform/methanol for development to give the title compound (12 mg, yield 29%).

¹H-NMR (CDCl₃, 400 MHz): δ 1.47 (d, J=6.8 Hz, 3H), 2.08-2.15 (m, 2H), 2.48 (br, 4H), 2.57 (t, J=7.1 Hz, 2H), 3.72 (t, J=4.4 Hz, 4H), 4.03 (s, 3H), 4.24 (t, J=6.6 Hz, 2H), 4.95-5.00 (m, 1H), 5.34 (br, 1H), 6.37 (d, J=4.4 Hz, 1H), 7.02-7.22 (m, 5H), 7.41 (s, 1H), 7.49 (dd, J=2.4, 12.2 Hz, 1H), 7.57 (s, 1H), 8.45 (d, J=5.4 Hz, 1H)

Mass spectrometric value (ESI-MS, m/z): 609 (M⁺−1)

Example 66

N-[1-(2,4-Difluorophenyl)ethyl]-N'-(3-fluoro-4-{[6-methoxy-7-(3-morpholinopropoxy)-4-quinolyl]oxy}phenyl)urea 3-Fluoro-4-{[6-methoxy-7-(3-morpholinopropoxy)-4-quinolyl]oxy}-aniline (30 mg) was dissolved in chloroform (3 ml) and triethylamine (0.3 ml) to prepare a solution. A solution of triphosgene (17 mg) in chloroform (0.2 ml) was then added to the solution, and the mixture was stirred at room temperature for 25 min. Next, a solution of 1-(2,4-difluorophenyl)ethylamine (14 mg) in chloroform (0.2 ml) was added thereto, and the mixture was stirred at room temperature for 5 hr. The stirred mixture was purified by chromatography on silica gel using chloroform/methanol for development to give the title compound (25 mg, yield 57%).

¹H-NMR (CDCl₃, 400 MHz): δ 1.54 (d, J=6.6 Hz, 3H), 2.11-2.16 (m, 2H), 2.49 (br, 4H), 2.58 (t, J=6.8 Hz, 2H), 3.73 (t, J=4.6 Hz, 4H), 4.03 (s, 3H), 4.26 (t, J=6.8 Hz, 2H), 5.13-5.19 (m, 1H), 6.37 (d, J=5.4 Hz, 1H), 6.57 (s, 1H), 6.79-6.88 (m, 2H), 6.97-7.06 (m, 1H), 7.14 (t, J=8.8 Hz, 1H), 7.29-7.35 (m, 1H), 7.42 (s, 1H), 7.49 (dd, J=2.4, 12.2 Hz, 1H), 7.56 (s, 1H), 8.45 (d, J=5.4 Hz, 1H)

Mass spectrometric value (ESI-MS, m/z): 609 (M⁺−1)

Example 67

N-(2-Fluoro-4-{[6-methoxy-7-(3-morpholinopropoxy)-4-quinolyl]oxy}phenyl)-N'-[1-(4-fluorophenyl)ethyl]urea 2-Fluoro-4-{[6-methoxy-7-(3-morpholinopropoxy)-4-quinolyl]oxy}-aniline (30 mg) was dissolved in chloroform (3 ml) and triethylamine (0.3 ml) to prepare a solution. A solution of triphosgene (17 mg) in chloroform (0.2 ml) was then added to the solution, and the mixture was stirred at room temperature for 25 min. Next, a solution of 1-(4-fluorophenyl)ethylamine (12 mg) in chloroform (0.2 ml) was added thereto, and the mixture was stirred at room temperature for 5 hr. The stirred mixture was purified by chromatography on silica gel using chloroform/methanol for development to give the title compound (31 mg, yield 73%).

¹H-NMR (CDCl₃, 400 MHz): δ 1.53 (d, J=6.8 Hz, 3H), 2.09-2.16 (m, 2H), 2.48 (br, 4H), 2.57 (t, J=7.1 Hz, 2H), 3.72 (t, J=4.9 Hz, 4H), 4.01 (s, 3H), 4.26 (t, J=6.8 Hz, 2H), 4.95-4.99 (m, 1H), 5.04 (d, J=6.8 Hz, 1H), 6.46 (d, J=5.1 Hz, 1H), 6.48 (d, J=2.9 Hz, 1H), 6.89-6.96 (m, 2H), 7.05 (t, J=8.5 Hz, 2H), 7.35 (dd, J=5.4, 8.8 Hz, 2H), 7.42 (s, 1H), 7.48 (s, 1H), 8.16 (t, J=9.0 Hz, 1H), 8.48 (d, J=5.4 Hz, 1H)

Mass spectrometric value (ESI-MS, m/z): 591 (M⁺−1)

Example 68

N-[1-(3,4-Difluorophenyl)ethyl]-N'-(2-fluoro-4-{[6-methoxy-7-(3-morpholinopropoxy)-4-quinolyl]oxy}phenyl)urea 2-Fluoro-4-{[6-methoxy-7-(3-morpholinopropoxy)-4-quinolyl]oxy}-aniline (30 mg) was dissolved in chloroform (3 ml) and triethylamine (0.3 ml) to prepare a solution. A solution of triphosgene (17 mg) in chloroform (0.2 ml) was then added to the solution, and the mixture was stirred at room temperature for 25 min. Next, a solution of 1-(3,4-difluorophenyl)ethylamine (14 mg) in chloroform (0.2 ml) was added thereto, and the mixture was stirred at room temperature for 5 hr. The stirred mixture was purified by chromatography on silica gel using chloroform/methanol for development to give the title compound (27 mg, yield 60%).

¹H-NMR (CDCl₃, 400 MHz): δ 1.52 (d, J=6.8 Hz, 3H), 2.09-2.16 (m, 2H), 2.49 (br, 4H), 2.58 (t, J=7.1 Hz, 2H), 3.73 (t, J=4.6 Hz, 4H), 4.01 (s, 3H), 4.26 (t, J=6.6 Hz, 2H), 4.95-5.00 (m, 1H), 5.09 (d, J=6.8 Hz, 1H), 6.47 (d, J=5.4 Hz, 1H), 6.54 (d, J=3.2 Hz, 1H), 6.91-6.96 (m, 2H), 7.09-7.23 (m, 3H), 7.42 (s, 1H), 7.48 (s, 1H), 8.14 (t, J=8.8 Hz, 2H), 8.48 (d, J=5.1 Hz, 1H)

Mass spectrometric value (ESI-MS, m/z): 609 (M⁺−1)

Example 69

N-[1-(2,4-Difluorophenyl)ethyl]-N'-(2-fluoro-4-{[6-methoxy-7-(3-morpholinopropoxy)-4-quinolyl]oxy}phenyl)urea 2-Fluoro-4-{[6-methoxy-7-(3-morpholinopropoxy)-4-quinolyl]oxy}-aniline (30 mg) was dissolved in chloroform (3 ml) and triethylamine (0.3 ml) to prepare a solution. A solution of triphosgene (17 mg) in chloroform (0.2 ml) was then added to the solution, and the mixture was stirred at room temperature for 25 min. Next, a solution of 1-(2,4-difluorophenyl)ethylamine (14 mg) in chloroform (0.2 ml) was added thereto, and the mixture was stirred at room temperature for 5 hr. The stirred mixture was purified by chromatography on silica gel using chloroform/methanol for development to give the title compound (29 mg, yield 66%).

$^1$H-NMR (CDCl$_3$, 400 MHz): δ 1.55 (d, J=6.6 Hz, 3H), 2.09-2.16 (m, 2H), 2.49 (br, 4H), 2.58 (t, J=6.8 Hz, 2H), 3.73 (t, J=4.6 Hz, 4H), 4.01 (s, 3H), 4.27 (t, J=6.8 Hz, 2H), 5.14-5.17 (m, 1H), 5.22 (d, J=7.8 Hz, 1H), 6.46 (d, J=5.1 Hz, 1H), 6.50 (d, J=2.7 Hz, 1H), 6.80-6.88 (m, 2H), 6.91-7.00 (m, 2H), 7.33 (dd, J=8.5, 14.6 Hz, 1H), 7.43 (s, 1H), 7.48 (s, 1H), 8.14 (t, J=8.8 Hz, 2H), 8.48 (d, J=5.4 Hz, 1H)

Mass spectrometric value (ESI-MS, m/z): 609 (M$^+$−1)

Example 70

N-{4-[(6,7-Dimethoxy-4-quinolyl)oxy]-2-fluorophenyl}-N'-[1-(1,3-thiazol-2-yl)ethyl]urea 4-[(6,7-Dimethoxy-4-quinolyl)oxy]-2-fluoroaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (35 mg, yield 79%).

$^1$H-NMR (CDCl$_3$, 400 MHz): δ 1.70 (d, J=7.1 Hz, 3H), 4.04 (s, 3H), 4.05 (s, 3H), 5.37-5.42 (m, 1H), 5.80 (d, J=7.3 Hz, 1H), 6.49 (d, J=5.1 Hz, 1H), 6.93-6.98 (m, 2H), 7.01 (br, 1H), 7.31 (d, J=3.0 Hz, 1H), 7.42 (s, 1H), 7.50 (s, 1H), 7.74 (d, J=3.2 Hz, 1H), 8.17 (d, J=9.3 Hz, 1H), 8.50 (d, J=5.4 Hz, 1H)

Mass spectrometric value (ESI-MS, m/z): 469 (M$^+$+1)

Example 71

N-{4-[(6,7-Dimethoxy-4-quinolyl)oxy]-2-fluorophenyl}-N'-[(1S)-1-(1,3-thiazol-2-yl)ethyl]urea 4-[(6,7-Dimethoxy-4-quinolyl)oxy]-2-fluoroaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (30 mg, yield 66%).

$^1$H-NMR (CDCl$_3$, 400 MHz): δ 1.71 (d, J=6.8 Hz, 3H), 4.07 (s, 3H), 4.10 (s, 3H), 5.34-5.39 (m, 1H), 6.60 (d, J=6.1 Hz, 1H), 6.61 (s, 1H), 6.90 (dd, J=2.7, 11.0 Hz, 1H), 6.97-6.99 (m, 1H), 7.27 (s, 1H), 7.57 (s, 1H), 7.70 (d, J=3.4 Hz, 1H), 7.74 (br, 1H), 7.77 (s, 1H), 8.33 (dd, J=9.0, 9.0 Hz, 1H), 8.47 (d, J=6.1 Hz, 1H)

Mass spectrometric value (ESI-MS, m/z): 469 (M$^+$+1)
[α]$_D^{25}$−39.2° (c0.5, CHCl$_3$)

Example 72

N-{4-[(6,7-Dimethoxy-4-quinolyl)oxy]-2-fluorophenyl}-N'-[(1R)-1-(1,3-thiazol-2-yl)ethyl]urea 4-[(6,7-Dimethoxy-4-quinolyl)oxy]-2-fluoroaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (28 mg, yield 62%).

$^1$H-NMR (CDCl$_3$, 400 MHz): δ 1.70 (d, J=7.1 Hz, 3H), 4.06 (s, 3H), 4.07 (s, 3H), 5.35-5.42 (m, 1H), 6.48 (d, J=6.8 Hz, 1H), 6.55 (d, J=5.9 Hz, 1H), 6.91 (dd, J=2.7, 11.2 Hz, 1H), 6.94-6.98 (m, 1H), 7.28 (d, J=3.2 Hz, 1H), 7.54 (s, 1H), 7.60 (br, 1H), 7.63 (s, 1H), 7.71 (d, J=3.4 Hz, 1H), 8.26 (d, J=9.0 Hz, 1H), 8.48 (d, J=5.6 Hz, 1H)

Mass spectrometric value (ESI-MS, m/z): 469 (M$^+$+1)
[α]$_D^{25}$+40.7° (c0.5, CHCl$_3$)

Example 73

N-{4-[(6,7-Dimethoxy-4-quinolyl)oxy]-3-fluorophenyl}-N'-[1-(1,3-thiazol-2-yl)ethyl]urea 4-[(6,7-Dimethoxy-4-quinolyl)oxy]-3-fluoroaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (39 mg, yield 87%).

$^1$H-NMR (CDCl$_3$, 400 MHz): δ 1.69 (d, J=6.8 Hz, 3H), 4.03 (s, 3H), 4.04 (s, 3H), 5.33-5.42 (m, 1H), 5.95 (d, J=7.3 Hz, 1H), 6.39 (dd, J=1.0, 5.1 Hz, 1H), 7.05 (dd, J=1.5, 8.8 Hz, 1H), 7.13 (d, J=8.8, 8.8 Hz, 1H), 7.34 (d, J=3.2 Hz, 1H), 7.41 (s, 1H), 7.53 (d, J=2.4, 12.2 Hz, 1H), 7.57 (s, 1H), 7.74 (d, J=3.2 Hz, 1H), 8.47 (d, J=5.4 Hz, 1H)

Mass spectrometric value (ESI-MS, m/z): 469 (M$^+$+1)

Example 74

N-{4-[(6,7-Dimethoxy-4-quinolyl)oxy]-2-methoxyphenyl}-N'-[1-(1,3-thiazol-2-yl)ethyl]urea 4-[(6,7-Dimethoxy-4-quinolyl)oxy]-2-methoxyaniline (816 mg) was dissolved in chloroform (40 ml) and triethylamine (2.0 ml) to prepare a solution. A solution of triphosgene (368 mg) in chloroform (1.0 ml) was then added to the solution, and the mixture was stirred at room temperature for one hr. Next, a solution of 1-(1,3-thiazol-2-yl)-1-ethylamine (352 mg) in chloroform (1.0 ml) was added thereto, and the mixture was stirred at room temperature overnight. Water (40 ml) was added thereto, and the mixture was stirred for 10 min, followed by extraction with chloroform. The organic layer was washed with saturated brine and was dried over sodium sulfate. The solvent was removed by evaporation, and the residue was purified by chromatography on silica gel using chloroform/acetone for development to give the title compound (860 mg, 72%).

$^1$H-NMR (CDCl$_3$, 400 MHz): δ 1.69 (d, J=6.8 Hz, 3H), 3.83 (s, 3H), 4.06 (s, 3H), 4.07 (s, 3H), 5.37-5.45 (m, 1H), 5.67 (d, J=7.3 Hz, 1H), 6.51 (d, J=5.4 Hz, 1H), 6.70 (d, J=2.4 Hz, 1H), 6.79 (dd, J=2.4, 8.8 Hz, 1H), 7.02 (s, 1H), 7.30 (d, J=3.4 Hz, 1H), 7.53 (s, 1H), 7.57 (s, 1H), 7.73 (d, J=3.4 Hz, 1H), 8.19 (d, J=8.8 Hz, 1H), 8.47 (d, J=5.4 Hz, 1H)

Mass spectrometric value (ESI-MS, m/z): 481 (M$^+$+1)

Example 75

N-{4-[(6,7-Dimethoxy-4-quinolyl)oxy]-2-methoxyphenyl}-N'-[(1S)-1-(1,3-thiazol-2-yl)ethyl]urea 4-[(6,7-Dimethoxy-4-quinolyl)oxy]-2-methoxyaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (33 mg, yield 75%).

$^1$H-NMR (CDCl$_3$, 400 MHz): δ 1.68 (d, J=6.8 Hz, 3H), 3.78 (s, 3H), 4.05 (s, 3H), 4.07 (s, 3H), 5.38-5.45 (m, 1H), 6.08 (d, J=7.6 Hz, 1H), 6.52 (d, J=5.6 Hz, 1H), 6.67 (d, J=2.4 Hz, 1H), 6.77 (dd, J=2.7, 8.8 Hz, 1H), 7.21 (s, 1H), 7.30 (d, J=3.4 Hz, 1H), 7.57 (s, 1H), 7.59 (s, 1H), 7.72 (d, J=3.2 Hz, 1H), 8.21 (d, J=8.8 Hz, 1H), 8.46 (d, J=5.6 Hz, 1H)

Mass spectrometric value (ESI-MS, m/z): 481 (M$^+$+1)
[α]$_D^{25}$−16.4° (c0.5, CHCl$_3$)

Example 76

N-{4-[(6,7-Dimethoxy-4-quinolyl)oxy]-2-methoxyphenyl}-N'-[(1R)-1-(1,3-thiazol-2-yl)ethyl]urea 4-[(6,7-Dimethoxy-4-quinolyl)oxy]-2-methoxyaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (36 mg, yield 82%).

$^1$H-NMR (CDCl$_3$, 400 MHz): δ 1.68 (d, J=6.8 Hz, 3H), 3.78 (s, 3H), 4.05 (s, 3H), 4.07 (s, 3H), 5.38-5.45 (m, 1H), 6.08 (d, J=7.6 Hz, 1H), 6.52 (d, J=5.6 Hz, 1H), 6.67 (d, J=2.4 Hz, 1H), 6.77 (dd, J=2.7, 8.8 Hz, 1H), 7.21 (s, 1H), 7.30 (d, J=3.4 Hz, 1H), 7.57 (s, 1H), 7.59 (s, 1H), 7.72 (d, J=3.2 Hz, 1H), 8.21 (d, J=8.8 Hz, 1H), 8.46 (d, J=5.6 Hz, 1H)

Mass spectrometric value (ESI-MS, m/z): 481 (M$^+$+1)
[α]$_D^{24}$+14.1° (c0.5, CHCl$_3$)

Example 77

N-{4-[(6,7-Dimethoxy-4-quinolyl)oxy]phenyl}-N'-[1-(1,3-thiazol-2-yl)ethyl]urea

4-[(6,7-Dimethoxy-4-quinolyl)oxy]aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (36 mg, yield 78%).

$^1$H-NMR (CDCl$_3$, 400 MHz): δ 1.69 (d, J=7.1 Hz, 3H), 4.06 (s, 3H), 4.07 (s, 3H), 5.34-5.40 (m, 1H), 6.51 (d, J=6.6 Hz, 1H), 6.70 (s, 1H), 7.05 (d, J=9.0 Hz, 1H), 7.20 (d, J=3.2 Hz, 1H), 7.64 (s, 1H), 7.65 (d, J=3.2 Hz, 1H), 7.72 (d, J=9.0 Hz, 1H), 7.89 (s, 1H), 8.26 (d, J=6.6 Hz, 1H), 8.91 (s, 1H)

Mass spectrometric value (ESI-MS, m/z): 451 (M$^+$+1)

Example 78

N-{4-[(6,7-Dimethoxy-4-quinolyl)oxy]phenyl}-N'-[(S)-1-(1,3-thiazol-2-yl)ethyl]urea 4-[(6,7-Dimethoxy-4-quinolyl)oxy]aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (31 mg, yield 68%).

$^1$H-NMR (CDCl$_3$, 400 MHz): δ 1.68 (d, J=6.8 Hz, 3H), 4.09 (s, 3H), 4.10 (s, 3H), 5.32-5.38 (m, 1H), 6.51 (d, J=6.3 Hz, 1H), 6.55 (br, 1H), 7.06 (d, J=8.8 Hz, 1H), 7.22 (d, J=3.2 Hz, 1H), 7.64 (d, J=1.2 Hz, 1H), 7.66 (d, J=3.4 Hz, 1H), 7.67 (s, 1H), 7.79 (s, 1H), 8.31 (d, J=6.3 Hz, 1H), 8.59 (s, 1H)

Mass spectrometric value (ESI-MS, m/z): 451 (M$^+$+1)
[α]$_D^{25}$−24.6° (c0.5, CHCl$_3$)

Example 79

N-{4-[(6,7-Dimethoxy-4-quinolyl)oxy]phenyl}-N'-[(1R)-1-(1,3-thiazol-2-yl)ethyl]urea 4-[(6,7-Dimethoxy-4-quinolyl)oxy]aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (28 mg, yield 62%).

$^1$H-NMR (CDCl$_3$, 400 MHz): δ 1.69 (d, J=7.1 Hz, 3H), 4.11 (s, 3H), 4.12 (s, 3H), 5.31-5.37 (m, 1H), 6.51 (d, J=6.6 Hz, 1H), 6.70 (s, 1H), 7.05 (d, J=9.0 Hz, 1H), 7.20 (d, J=3.2 Hz, 1H), 7.65 (s, 1H), 7.65 (d, J=3.2 Hz, 1H), 7.72 (d, J=9.0 Hz, 1H), 7.89 (s, 1H), 8.26 (d, J=6.6 Hz, 1H), 8.91 (s, 1H)

Mass spectrometric value (ESI-MS, m/z): 451 (M$^+$+1)
[α]$_D^{24}$+23.9° (c0.5, CHCl$_3$)

Example 80

N-{4-[(6,7-Dimethoxy-4-quinolyl)oxy]-3-methoxyphenyl}-N'-[1-(1,3-thiazol-2-yl)ethyl]urea 4-[(6,7-Dimethoxy-4-quinolyl)oxy]-3-methoxyaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (28 mg, yield 62%).

$^1$H-NMR (CDCl$_3$, 400 MHz): δ 1.69 (d, J=6.8 Hz, 3H), 3.71 (s, 3H), 4.09 (s, 3H), 4.10 (s, 3H), 5.34-5.39 (m, 1H), 6.38 (d, J=6.3 Hz, 1H), 6.70 (br, 1H), 6.94 (dd, J=2.2, 8.5 Hz, 1H), 6.99 (d, J=8.8 Hz, 1H), 7.20 (d, J=3.2 Hz, 1H), 7.66 (d, J=2.9 Hz, 1H), 7.66 (s, 1H), 7.73 (d, J=2.2 Hz, 1H), 7.80 (s, 1H), 8.23 (d, J=6.6 Hz, 1H), 8.78 (br, 1H)

Mass spectrometric value (ESI-MS, m/z): 479 (M$^+$−1)

Example 81

N-{4-[(6,7-Dimethoxy-4-quinolyl)oxy]-3-methoxyphenyl}-N'-[(1S)-1-(1,3-thiazol-2-yl)ethyl]urea 4-[(6,7-Dimethoxy-4-quinolyl)oxy]-3-methoxyaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (31 mg, yield 72%).

$^1$H-NMR (CDCl$_3$, 400 MHz): δ 1.70 (d, J=6.8 Hz, 3H), 3.70 (s, 3H), 4.11 (s, 3H), 4.13 (s, 3H), 5.33-5.39 (m, 1H), 6.39 (d, J=6.6 Hz, 1H), 6.87 (s, 1H), 6.99 (s, 1H), 7.18 (d, J=3.2 Hz, 1H), 7.65 (d, J=3.4 Hz, 1H), 7.68 (s, 1H), 7.82 (s, 1H), 7.92 (s, 1H), 8.17 (d, J=6.6 Hz, 1H), 9.16 (s, 1H)

Mass spectrometric value (ESI-MS, m/z): 479 (M$^+$−1)
[α]$_D^{25}$−24.0° (c0.5, CHCl$_3$)

Example 82

N-{4-[(6,7-Dimethoxy-4-quinolyl)oxy]-3-methoxyphenyl}-N'-[(1R)-1-(1,3-thiazol-2-yl)ethyl]urea 4-[(6,7-Dimethoxy-4-quinolyl)oxy]-3-methoxyaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (31 mg, yield 71%).

$^1$H-NMR (CDCl$_3$, 400 MHz): δ 1.68 (d, J=6.8 Hz, 3H), 3.71 (s, 3H), 4.06 (s, 3H), 4.07 (s, 3H), 5.35-5.43 (m, 1H), 6.36 (d, J=6.1 Hz, 1H), 6.48 (s, 1H), 6.86 (dd, J=2.2, 8.5 Hz, 1H), 7.00 (d, J=8.5 Hz, 1H), 7.25 (d, J=3.4 Hz, 1H), 7.59 (d, J=2.2 Hz, 1H), 7.62 (s, 1H), 7.63 (s, 1H), 7.67 (d, J=3.2 Hz, 1H), 8.26 (s, 1H), 8.33 (d, J=5.9 Hz, 1H)

Mass spectrometric value (ESI-MS, m/z): 479 (M$^+$+1)
[α]$_D^{25}$+26.7° (c0.5, CHCl$_3$)

Example 83

N-[4-[(6,7-Dimethoxy-4-quinolyl)oxy]-2-(trifluoromethyl)phenyl]-N'-[1-(1,3-thiazol-2-yl)ethyl]urea 4-[(6,7-Dimethoxy-4-quinolyl)oxy]-2-(trifluoromethyl)aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room is temperature for one hr. Next, a solution of 1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (29 mg, yield 68%).

$^1$H-NMR (CDCl$_3$, 400 MHz): δ 1.71 (d, J=7.1 Hz, 3H), 4.08 (s, 3H), 4.12 (s, 3H), 5.34-5.40 (m, 1H), 6.29 (br, 1H), 6.61 (d, J=6.1 Hz, 1H), 7.21 (s, 1H), 7.30 (d, J=3.4 Hz, 1H), 7.38 (dd, J=2.9, 9.0 Hz, 1H), 7.44 (d, J=2.9 Hz, 1H), 7.57 (s, 1H), 7.72 (d, J=3.2 Hz, 1H), 7.87 (br, 1H), 8.27 (d, J=9.0 Hz, 1H), 8.50 (d, J=6.1 Hz, 1H)

Mass spectrometric value (ESI-MS, m/z): 517 (M$^+$−1)

Example 84

N-[4-[(6,7-Dimethoxy-4-quinolyl)oxy]-2-(trifluoromethyl)phenyl]-N'-[(1S)-1-(1,3-thiazol-2-yl)ethyl]urea 4-[(6,7-Dimethoxy-4-quinolyl)oxy]-2-(trifluoromethyl)aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (29 mg, yield 68%).

$^1$H-NMR (CDCl$_3$, 400 MHz): δ 1.70 (d, J=6.8 Hz, 3H), 4.07 (s, 3H), 4.10 (s, 3H), 5.34-5.41 (m, 1H), 6.26 (d, J=6.8 Hz, 1H), 6.58 (d, J=5.9 Hz, 1H), 7.16 (s, 1H), 7.30 (d, J=3.2 Hz, 1H), 7.37 (dd, J=2.9, 9.0 Hz, 1H), 7.44 (d, J=2.7 Hz, 1H), 7.55 (s, 1H), 7.72 (d, J=3.4 Hz, 1H), 7.75 (br, 1H), 8.23 (d, J=9.0 Hz, 1H), 8.51 (d, J=5.9 Hz, 1H)

Mass spectrometric value (ESI-MS, m/z): 517 (M$^+$−1)
[α]$_D^{25}$−34.3° (c0.5, CHCl$_3$)

Example 85

N-[4-[(6,7-Dimethoxy-4-quinolyl)oxy]-2-(trifluoromethyl)phenyl]-N'-[(1R)-1-(1,3-thiazol-2-yl)ethyl]urea 4-[(6,7-Dimethoxy-4-quinolyl)oxy]-2-(trifluoromethyl)aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (30 mg, yield 71%).

$^1$H-NMR (CDCl$_3$, 400 MHz): δ 1.70 (d, J=6.8 Hz, 3H), 4.06 (s, 3H), 4.09 (s, 3H), 5.35-5.42 (m, 1H), 6.33 (d, J=7.1 Hz, 1H), 6.55 (d, J=5.9 Hz, 1H), 7.17 (s, 1H), 7.30 (d, J=3.2 Hz, 1H), 7.36 (dd, J=2.9, 9.0 Hz, 1H), 7.43 (d, J=2.9 Hz, 1H), 7.54 (s, 1H), 7.67 (s, 1H), 7.71 (d, J=3.4 Hz, 1H), 8.20 (d, J=9.0 Hz, 1H), 8.51 (d, J=5.9 Hz, 1H)

Mass spectrometric value (ESI-MS, m/z): 517 (M$^+$−1)
[α]$_D^{25}$+36.6° (c0.5, CHCl$_3$)

Example 86

N-{4-[(6,7-Dimethoxy-4-quinolyl)oxy]-2,5-dimethylphenyl}-N'-[(1S)-1-(1,3-thiazol-2-yl)ethyl]urea 4-[(6,7-Dimethoxy-4-quinolyl)oxy]-2,5-dimethylaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1S)-1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (30 mg, yield 68%).

$^1$H-NMR (CDCl$_3$, 400 MHz): δ 1.68 (d, J=6.8 Hz, 3H), 2.10 (s, 3H), 2.30 (s, 3H), 4.09 (s, 3H), 4.11 (s, 3H), 5.33-5.39 (m, 1H), 6.29 (br, 1H), 6.47 (d, J=6.1 Hz, 1H), 6.92 (s, 1H), 7.16 (br, 1H), 7.63 (s, 1H), 7.67 (d, J=3.2 Hz, 1H), 7.75 (s, 1H), 7.84 (s, 1H), 8.38 (d, J=6.1 Hz, 1H)

Mass spectrometric value (ESI-MS, m/z): 479 (M$^+$+1)
$[\alpha]_D^{25}$+10.6° (c0.5, CHCl$_3$)

Example 87

N-{4-[(6,7-Dimethoxy-4-quinolyl)oxy]-2,5-dimethylphenyl}-N'-[(1R)-1-(1,3-thiazol-2-yl)ethyl]urea 4-[(6,7-Dimethoxy-4-quinolyl)oxy]-2,5-dimethylaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of (1R)-1-(1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (30 mg, yield 68%).

$^1$H-NMR (CDCl$_3$, 400 MHz): δ 1.67 (d, J=6.8 Hz, 3H), 2.12 (s, 3H), 2.25 (s, 3H), 4.07 (s, 3H), 4.07 (s, 3H), 5.35-5.42 (m, 1H), 6.13 (d, J=7.1 Hz, 1H), 6.38 (d, J=5.6 Hz, 1H), 6.92 (s, 1H), 6.98 (s, 1H), 7.27 (d, J=3.2 Hz, 1H), 7.60 (s, 1H), 7.65 (s, 1H), 7.68 (d, J=3.4 Hz, 1H), 8.42 (d, J=5.6 Hz, 1H)

Mass spectrometric value (ESI-MS, m/z): 479 (M$^+$+1)
$[\alpha]_D^{25}$−9.0° (c0.5, CHCl$_3$)

Example 88

N-{4-[(6,7-Dimethoxy-4-quinolyl)oxy]-2-fluorophenyl}-N'-[1-(4-methyl-1,3-thiazol-2-yl)ethyl]urea 4-[(6,7-Ddimethoxy-4-quinolyl)oxy]-2-fluoroaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(4-methyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (38 mg, yield 83%).

$^1$H-NMR (CDCl$_3$, 400 MHz): δ 1.68 (d, J=7.1 Hz, 3H), 2.43 (d, J=1.0 Hz, 3H), 4.06 (s, 3H), 4.08 (s, 3H), 5.26-5.33 (m, 1H), 6.38 (br, 1H), 6.57 (d, J=5.9 Hz, 1H), 6.81 (d, J=1.0 Hz, 1H), 6.91 (dd, J=2.7, 11.0 Hz, 1H), 6.95-6.98 (m, 1H), 7.55 (s, 1H), 7.69 (s, 1H), 7.69 (br, 1H), 8.28 (t, J=9.0 Hz, 1H), 8.48 (d, J=5.9 Hz, 1H)

Mass spectrometric value (ESI-MS, m/z): 483 (M$^+$+1)

Example 89

N-{4-[(6,7-Dimethoxy-4-quinolyl)oxy]-3-fluorophenyl}-N'-[1-(4-methyl-1,3-thiazol-2-yl)ethyl]urea 4-[(6,7-Dimethoxy-4-quinolyl)oxy]-3-fluoroaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(4-methyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (29 mg, yield 63%).

$^1$H-NMR (CDCl$_3$, 400 MHz): δ 1.65 (d, J=6.8 Hz, 3H), 2.40 (d, J=0.7 Hz, 3H), 4.04 (s, 3H), 4.06 (s, 3H), 5.25-5.32 (m, 1H), 6.43 (br, 1H), 6.46 (d, J=4.9 Hz, 1H), 6.80 (d, J=1.2 Hz, 1H), 7.08 (t, J=8.8 Hz, 1H), 7.14 (dd, J=2.2, 8.8 Hz, 1H), 7.57 (s, 1H), 7.58-7.62 (m, 2H), 8.41 (d, J=5.9 Hz, 1H), 8.44 (br, 1H)

Mass spectrometric value (ESI-MS, m/z): 483 (M$^+$+1)

Example 90

N-{4-[(6,7-Dimethoxy-4-quinolyl)oxy]-2-methoxyphenyl}-N'-[1-(4-methyl-1,3-thiazol-2-yl)ethyl]urea 4-[(6,7-Dimethoxy-4-quinolyl)oxy]-2-methoxyaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(4-methyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (22 mg, yield 48%).

$^1$H-NMR (CDCl$_3$, 400 MHz): δ 1.66 (d, J=7.1 Hz, 3H), 2.44 (d, J=1.0 Hz, 3H), 3.82 (s, 3H), 4.07 (s, 3H), 4.11 (s, 3H), 5.29-5.36 (m, 1H), 6.01 (d, J=7.1 Hz, 1H), 6.60 (d, J=6.1 Hz, 1H), 6.68 (d, J=2.7 Hz, 1H), 6.78 (dd, J=2.7, 9.0 Hz, 1H), 6.82 (d, J=1.2 Hz, 1H), 7.23 (s, 1H), 7.60 (s, 1H), 7.84 (br, 1H), 8.28 (d, J=8.8 Hz, 1H), 8.45 (d, J=6.1 Hz, 1H)

Mass spectrometric value (ESI-MS, m/z): 495 (M$^+$+1)

Example 91

N-{4-[(6,7-Dimethoxy-4-quinolyl)oxy]phenyl}-N'-[1-(4-methyl-1,3-thiazol-2-yl)ethyl]urea 4-[(6,7-Dimethoxy-4-quinolyl)oxy]-2-methoxyaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(4-methyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (32 mg, yield 68%).

$^1$H-NMR (CDCl$_3$, 400 MHz): δ 1.65 (d, J=6.8 Hz, 3H), 2.40 (d, J=1.0 Hz, 3H), 4.06 (s, 3H), 4.07 (s, 3H), 5.25-5.32 (m, 1H), 6.24 (br, 1H), 6.48 (d, J=5.6 Hz, 1H), 6.78 (d, J=1.0 Hz, 1H), 7.06 (d, J=9.0 Hz, 1H), 7.54 (d, J=9.0 Hz, 1H), 7.58 (s, 1H), 7.60 (s, 1H), 8.09 (br, 1H), 8.39 (d, J=5.9 Hz, 1H)

Mass spectrometric value (ESI-MS, m/z): 465 (M$^+$+1)

Example 92

N-[4-[(6,7-Dimethoxy-4-quinolyl)oxy]-2-(trifluoromethyl)phenyl]-N'-[1-(4-methyl-1,3-thiazol-2-yl)ethyl]urea 4-[(6,7-Dimethoxy-4-quinolyl)oxy]-2-(trifluoromethyl)aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(4-methyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (35 mg, yield 80%).

$^1$H-NMR (CDCl$_3$, 400 MHz): δ 1.67 (d, J=6.8 Hz, 3H), 2.42 (d, J=1.0 Hz, 3H), 4.06 (s, 3H), 4.08 (s, 3H), 5.27-5.34 (m, 1H), 6.33 (d, J=6.8 Hz, 1H), 6.53 (d, J=5.6 Hz, 1H), 6.82 (d, J=1.0 Hz, 1H), 7.10 (br, 1H), 7.30 (dd, J=2.7, 9.0 Hz, 1H), 7.42 (d, J=2.7 Hz, 1H), 7.53 (s, 1H), 7.62 (s, 1H), 7.21 (d, J=9.0 Hz, 1H), 8.51 (d, J=5.6 Hz, 1H)

Mass spectrometric value (ESI-MS, m/z): 533 (M$^+$+1)

Example 93

N-{4-[(6,7-Dimethoxy-4-quinolyl)oxy]-2,5-dimethylphenyl}-N'-[1-(4-methyl-1,3-thiazol-2-yl)ethyl]urea 4-[(6,7-Dimethoxy-4-quinolyl)oxy]-2,5-dimethylaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(4-methyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (27 mg, yield 59%).

$^1$H-NMR (CDCl$_3$, 400 MHz): δ 1.65 (d, J=6.8 Hz, 3H), 2.11 (s, 3H), 2.27 (s, 3H), 2.40 (d, J=1.0 Hz, 1H), 4.08 (s, 3H), 4.09 (s, 3H), 5.25-5.34 (m, 1H), 6.08 (br, 1H), 6.42 (d, J=5.9 Hz, 1H), 6.80 (s, 1H), 6.93 (s, 1H), 6.96 (br, 1H), 7.61 (s, 1H), 7.68-7.73 (m, 2H), 8.41 (d, J=5.9 Hz, 1H)

Mass spectrometric value (ESI-MS, m/z): 493 (M$^+$+1)

Example 94

N-{4-[(6,7-Dimethoxy-4-quinolyl)oxy]phenyl}-N'-[1-(4,5-dimethyl-1,3-thiazol-2-yl)ethyl]urea 4-[(6,7-Dimethoxy-4-quinolyl)oxy]aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(4,5-dimethyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (19 mg, yield 40%).

$^1$H-NMR (CDCl$_3$, 400 MHz): δ 1.60 (d, J=6.8 Hz, 3H), 2.28 (s, 3H), 2.31 (s, 3H), 4.03 (s, 3H), 4.04 (s, 3H), 5.19-5.26 (m, 1H), 6.29 (br, 1H), 6.44 (d, J=5.4 Hz, 1H), 7.05 (d, J=8.8 Hz, 2H), 7.46 (d, J=9.0 Hz, 2H), 7.48 (s, 1H), 7.55 (s, 1H), 8.04 (br, 1H), 8.43 (d, J=5.4 Hz, 1H)

Mass spectrometric value (ESI-MS, m/z): 479 (M$^+$+1)

Example 95

N-{4-[(6,7-Dimethoxy-4-quinolyl)oxy]-2-fluorophenyl}-N'-[1-(4,5-dimethyl-1,3-thiazol-2-yl)ethyl]urea 4-[(6,7-Dimethoxy-4-quinolyl)oxy]-2-fluoroaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(4,5-dimethyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (18 mg, yield 38%).

$^1$H-NMR (CDCl$_3$, 400 MHz): δ 1.62 (d, J=6.8 Hz, 3H), 2.30 (s, 3H), 2.32 (s, 3H), 4.03 (s, 3H), 4.05 (s, 3H), 5.19-5.25 (m, 1H), 6.50 (d, J=5.4 Hz, 1H), 6.58 (br, 1H), 6.87-7.05 (m, 2H), 7.51 (s, 1H), 7.71 (br, 1H), 8.22 (d, J=9.0 Hz, 1H), 8.48 (d, J=5.4 Hz, 1H)

Mass spectrometric value (ESI-MS, m/z): 497 (M$^+$+1)

Example 96

N-{4-[(6,7-Dimethoxy-4-quinolyl)oxy]-2-methylphenyl}-N'-[1-(4,5-dimethyl-1,3-thiazol-2-yl)ethyl]urea 4-[(6,7-Dimethoxy-4-quinolyl)oxy]-2-methylaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(4,5-dimethyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (18 mg, yield 39%).

$^1$H-NMR (CDCl$_3$, 400 MHz): δ 1.60 (d, J=6.8 Hz, 3H), 2.23 (s, 3H), 2.25 (s, 3H), 2.31 (s, 3H), 4.03 (s, 3H), 4.05 (s, 3H), 5.19-5.27 (m, 1H), 6.24 (br, 1H), 6.50 (d, J=5.4 Hz, 1H), 6.99 (d, J=2.7 Hz, 1H), 7.01 (s, 1H), 7.10 (s, 1H), 7.47 (s, 1H), 7.54 (s, 1H), 7.75 (d, J=9.5 Hz, 1H), 8.47 (d, J=5.6 Hz, 1H)

Mass spectrometric value (ESI-MS, m/z): 493 (M$^+$+1)

Example 97

N-[4-[(6,7-Dimethoxy-4-quinolyl)oxy]-2-(trifluoromethyl)phenyl]-N'-[1-(4,5-dimethyl-1,3-thiazol-2-yl)ethyl]urea 4-[(6,7-Dimethoxy-4-quinolyl)oxy]-2-(trifluoromethyl)aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(4,5-dimethyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (14 mg, yield 31%).

$^1$H-NMR (CDCl$_3$, 400 MHz): δ 1.62 (d, J=6.8 Hz, 3H), 2.29 (s, 3H), 2.32 (s, 3H), 4.04 (s, 3H), 4.06 (s, 3H), 5.21-5.25 (m, 1H), 6.49 (d, J=5.4 Hz, 1H), 6.65 (s, 1H), 7.15 (s, 1H), 7.33 (d, J=8.8 Hz, 1H), 7.40 (d, J=2.2 Hz, 1H), 7.52 (s, 1H), 7.52 (s, 1H), 8.20 (dd, J=9.0 Hz, 1H), 8.51 (d, J=5.4 Hz, 1H)

Mass spectrometric value (ESI-MS, m/z): 547 (M$^+$+1)

Example 98

N-{4-[(6,7-Dimethoxy-4-quinolyl)oxy]-2,5-dimethylphenyl}-N'-[1-(4,5-dimethyl-1,3-thiazol-2-yl)ethyl]urea 4-[(6,7-Dimethoxy-4-quinolyl)oxy]-2,5-dimethylaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(4,5-dimethyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (14 mg, yield 29%).

$^1$H-NMR (CDCl$_3$, 400 MHz): δ 1.61 (d, J=6.8 Hz, 3H), 2.12 (s, 3H), 2.21 (s, 3H), 2.26 (s, 3H), 2.29 (s, 3H), 4.05 (s, 3H), 4.06 (s, 3H), 5.20-5.26 (m, 1H), 6.13 (s, 1H), 6.36 (d, J=5.4 Hz, 1H), 6.91 (s, 1H), 6.91 (s, 1H), 7.55 (s, 1H), 7.59 (s, 1H), 7.66 (s, 1H), 8.43 (d, J=5.4 Hz, 1H)

Mass spectrometric value (ESI-MS, m/z): 507 (M$^+$+1)

Example 99

N-{4-[(6,7-Dimethoxy-4-quinolyl)oxy]-2-methoxyphenyl}-N'-[1-(4,5-dimethyl-1,3-thiazol-2-yl)ethyl]urea 4-[(6,7-Dimethoxy-4-quinolyl)oxy]-2-methoxyaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(4,5-dimethyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (45 mg, yield 100%).

$^1$H-NMR (CDCl$_3$, 400 MHz): δ 1.61 (d, J=6.8 Hz, 3H), 2.31 (s, 3H), 2.33 (s, 3H), 3.66 (s, 3H), 4.01 (s, 3H), 4.04 (s, 3H), 5.26-5.29 (m, 1H), 6.46 (d, J=5.4 Hz, 1H), 6.62 (d, J=2.4 Hz, 1H), 6.73 (dd, J=2.4, 8.8 Hz, 1H), 6.76 (s, 1H), 6.78 (s, 1H), 6.76 (s, 1H), 7.41 (s, 1H), 7.46 (s, 1H), 7.54 (s, 1H), 8.20 (d, J=8.8 Hz, 1H), 8.46 (d, J=5.4 Hz, 1H)

Mass spectrometric value (ESI-MS, m/z): 509 (M$^+$+1)

Example 100

N-{4-[(6,7-Dimethoxy-4-quinolyl)oxy]phenyl}-N'-[1-(5-methyl-1,3-thiazol-2-yl)ethyl]urea 4-[(6,7-Dimethoxy-4-quinolyl)oxy]aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(5-methyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (14 mg, yield 31%).

$^1$H-NMR (CDCl$_3$, 400 MHz): δ 1.49 (d, J=6.8 Hz, 3H), 2.39 (d, J=1.2 Hz, 3H), 3.92 (s, 3H), 3.93 (s, 3H), 5.00-5.06 (m, 1H), 6.40 (d, J=5.1 Hz, 1H), 6.87 (d, J=7.8 Hz, 1H), 7.15 (d, J=8.8 Hz, 2H), 7.37 (s, 1H), 7.38 (d, J=1.2 Hz, 1H), 7.50 (s, 1H), 7.52 (d, J=8.8 Hz, 2H), 8.44 (d, J=5.1 Hz, 1H), 8.70 (s, 1H)

Mass spectrometric value (ESI-MS, m/z): 465 (M$^+$+1)

Example 101

N-{4-[(6,7-Dimethoxy-4-quinolyl)oxy]-2-fluorophenyl}-N'-[1-(5-methyl-1,3-thiazol-2-yl)ethyl]urea 4-[(6,7-Dimethoxy-4-quinolyl)oxy]-2-fluoroaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(5-methyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (13 mg, yield 29%).

$^1$H-NMR (CDCl$_3$, 400 MHz): δ 1.66 (d, J=7.1 Hz, 3H), 2.42 (d, J=0.7 Hz, 3H), 4.07 (s, 3H), 4.10 (s, 3H), 5.24-5.28 (m, 1H), 6.57 (br, 1H), 6.60 (d, J=5.9 Hz, 1H), 6.90 (dd, J=2.7, 10.7 Hz, 1H), 6.96-6.98 (m, 1H), 7.32 (d, J=1.2 Hz, 1H), 7.57 (s, 1H), 7.75 (br, 1H), 7.78 (s, 1H), 8.33 (t, J=8.8 Hz, 1H), 8.48 (d, J=6.1 Hz, 1H)

Mass spectrometric value (ESI-MS, m/z): 483 (M$^+$+1)

Example 102

N-{4-[(6,7-Dimethoxy-4-quinolyl)oxy]-3-fluorophenyl}-N'-[1-(5-methyl-1,3-thiazol-2-yl)ethyl]urea 4-[(6,7-Dimethoxy-4-quinolyl)oxy]-3-fluoroaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(5-methyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (16 mg, yield 35%).

$^1$H-NMR (CDCl$_3$, 400 MHz): δ 1.63 (d, J=7.1 Hz, 3H), 2.41 (s, 3H), 4.04 (s, 3H), 4.06 (s, 3H), 5.23-5.27 (m, 1H), 6.47 (d, J=5.6 Hz, 1H), 6.54 (br, 1H), 7.08 (t, J=8.5 Hz, 1H), 7.17 (d, J=8.5 Hz, 1H), 7.29 (s, 1H), 7.59-7.63 (m, 3H), 8.42 (d, J=5.9 Hz, 1H), 8.57 (s, 1H)

Mass spectrometric value (ESI-MS, m/z): 483 (M$^+$+1)

Example 103

N-{4-[(6,7-Dimethoxy-4-quinolyl)oxy]-2-methylphenyl}-N'-[1-(5-methyl-1,3-thiazol-2-yl)ethyl]urea 4-[(6,7-Dimethoxy-4-quinolyl)oxy]-2-methylaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(5-methyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (14 mg, yield 31%).

$^1$H-NMR (CDCl$_3$, 400 MHz): δ 1.63 (d, J=7.1 Hz, 3H), 2.30 (s, 3H), 2.42 (s, 3H), 4.06 (s, 3H), 4.07 (s, 3H), 5.25-5.28 (m, 1H), 6.20 (s, 1H), 6.56 (d, J=5.9 Hz, 1H), 7.00 (s, 1H), 7.01 (d, J=2.9 Hz, 1H), 7.17 (s, 1H), 7.28 (s, 1H), 7.57 (s, 1H), 7.64 (s, 1H), 7.79 (d, J=9.5 Hz, 1H), 8.44 (d, J=5.9 Hz, 1H)

Mass spectrometric value (ESI-MS, m/z): 479 (M$^+$+1)

Example 104

N-[4-[(6,7-Dimethoxy-4-quinolyl)oxy]-2-(trifluoromethyl)phenyl]-N'-[1-(5-methyl-1,3-thiazol-2-yl)ethyl]urea 4-[(6,7-Dimethoxy-4-quinolyl)oxy]-2-(trifluoromethyl)aniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(5-methyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (12 mg, yield 26%).

$^1$H-NMR (CDCl$_3$, 400 MHz): δ 1.65 (d, J=6.8 Hz, 3H), 2.44 (d, J=0.7 Hz, 3H), 4.07 (s, 3H), 4.09 (s, 3H), 5.23-5.30 (m, 1H), 6.37 (d, J=6.3 Hz, 1H), 6.56 (d, J=5.6 Hz, 1H), 7.18 (s, 1H), 7.33 (d, J=1.2 Hz, 1H), 7.36 (dd, J=2.7, 9.0 Hz, 1H), 7.43 (d, J=2.7 Hz, 1H), 7.55 (s, 1H), 7.71 (s, 1H), 8.22 (d, J=9.0 Hz, 1H), 8.51 (d, J=5.9 Hz, 1H)

Mass spectrometric value (ESI-MS, m/z): 533 (M$^+$+1)

Example 105

N-{4-[(6,7-Dimethoxy-4-quinolyl)oxy]-2-methoxyphenyl}-N'-[1-(5-methyl-1,3-thiazol-2-yl)ethyl]urea 4-[(6,7-Dimethoxy-4-quinolyl)oxy]-2-methoxyaniline (30 mg) was dissolved in chloroform (1 ml) and triethylamine (0.1 ml) to prepare a solution. A solution of triphosgene (35 mg) in chloroform (0.2 ml) was then added to the solution, and the mixture was stirred at room temperature for one hr. Next, a solution of 1-(5-methyl-1,3-thiazol-2-yl)-1-ethylamine (35 mg) in chloroform (0.2 ml) was added thereto, and the mixture was stirred at room temperature for 10 hr. The stirred mixture was purified by chromatography on silica gel using chloroform/methanol for development to give the title compound (38 mg, yield 83%).

$^1$H-NMR (CDCl$_3$, 400 MHz): δ 1.63 (d, J=6.8 Hz, 3H), 2.44 (s, 3H), 3.70 (s, 3H), 4.03 (s, 3H), 4.04 (s, 3H), 5.28-5.35 (m, 1H), 6.47 (d, J=5.4 Hz, 1H), 6.49 (s, 1H), 6.76 (dd, J=2.2, 8.8 Hz, 1H), 7.35 (s, 1H), 7.37 (s, 1H), 7.46 (s, 1H), 7.56 (s, 1H), 8.21 (d, J=8.8 Hz, 1H), 8.47 (d, J=5.4 Hz, 1H)

Mass spectrometric value (ESI-MS, m/z): 495 (M$^+$+1)

Compounds of Examples 1 to 38 and 41 to 105 had the following respective chemical structures and c-fms autophosphorylation 50% inhibitory concentrations (IC$_{50}$).

TABLE 1

| Example | Chemical structure | IC$_{50}$ (μm) |
|---|---|---|
| 1 | 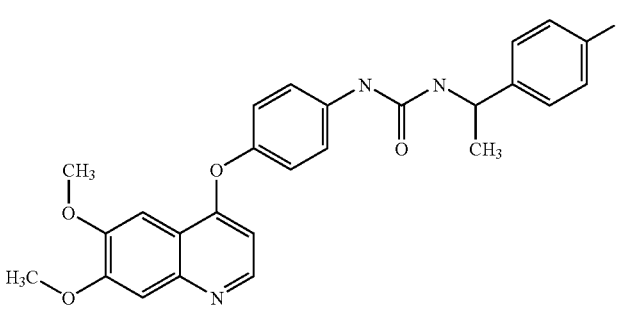 | 0.0024 |

TABLE 1-continued
| Example | Chemical structure | IC$_{50}$ (μm) |
|---|---|---|
| 2 | 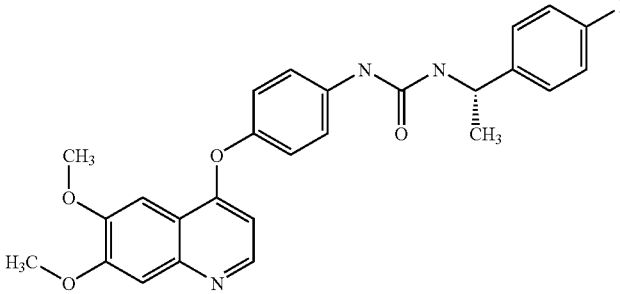 | 0.0022 |
| 3 | 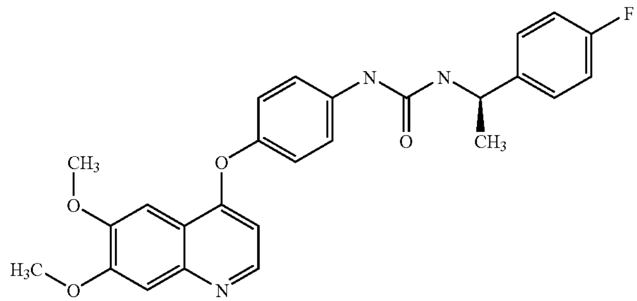 | 0.0024 |
| 4 | 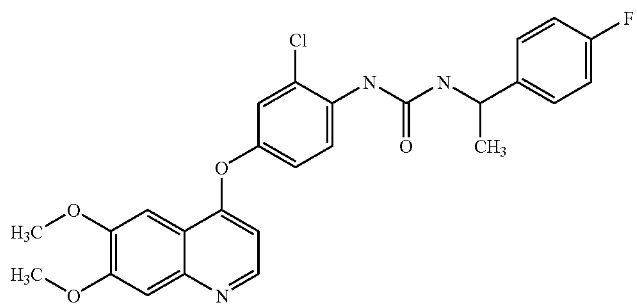 | 0.0040 |
| 5 | 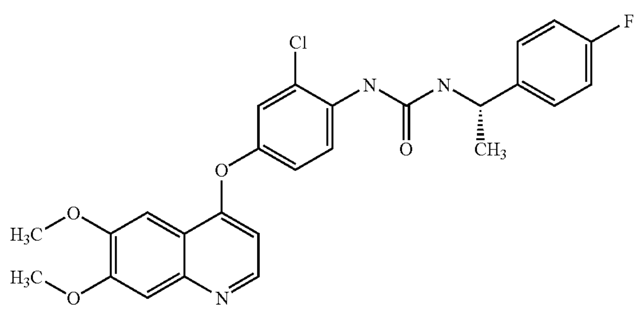 | 0.0022 |
| 6 | 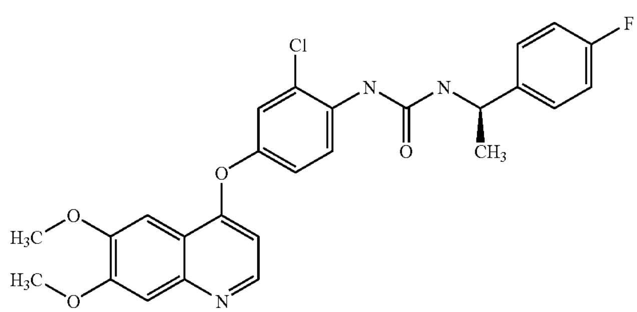 | 0.0060 |

TABLE 1-continued

| Example | Chemical structure | IC$_{50}$ (μm) |
|---|---|---|
| 7 | 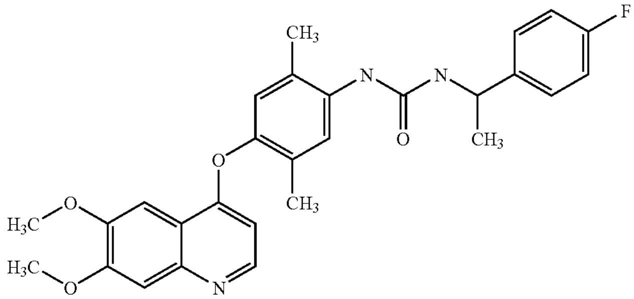 | 0.0202 |
| 8 | 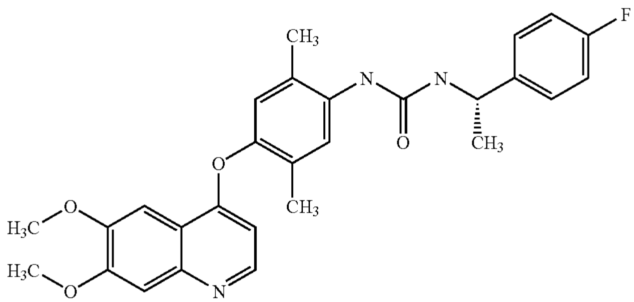 | 0.0225 |
| 9 | 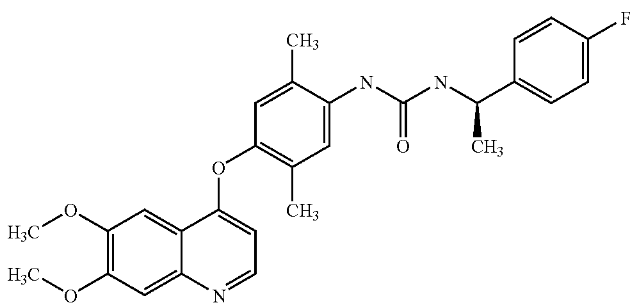 | 0.0174 |
| 10 | 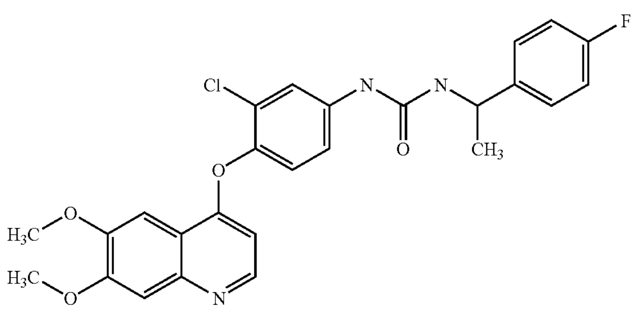 | 0.0071 |
| 11 | 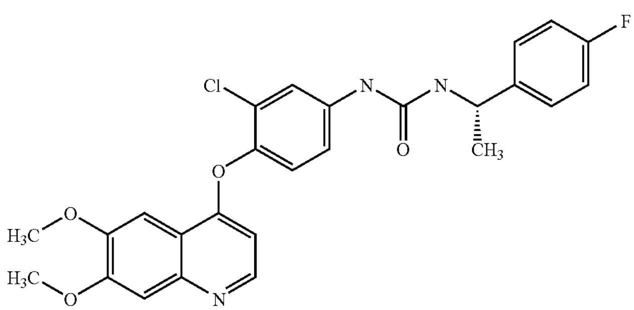 | 0.0117 |

TABLE 1-continued

| Example | Chemical structure | IC$_{50}$ (μm) |
|---|---|---|
| 12 | 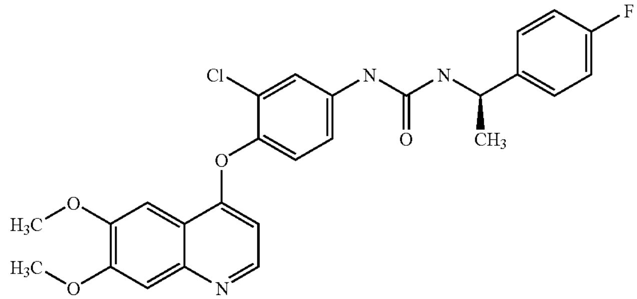 | 0.0109 |
| 13 | 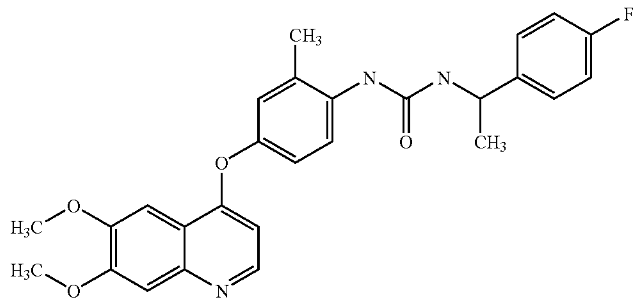 | 0.0061 |
| 14 | 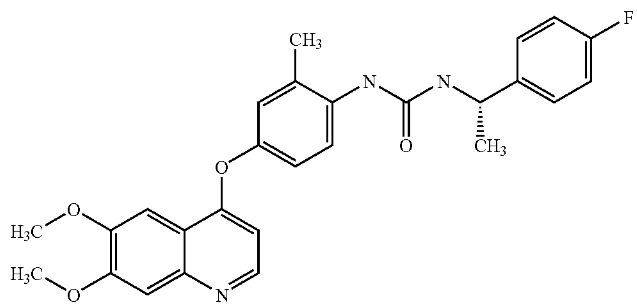 | 0.0130 |
| 15 | 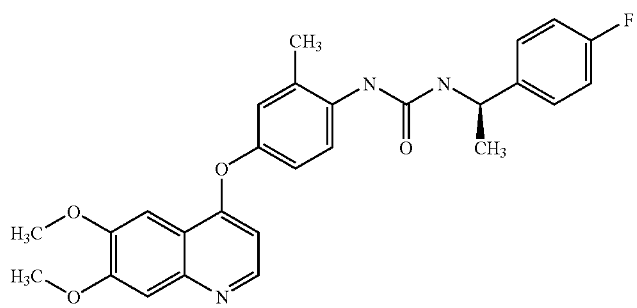 | 0.0057 |
| 16 | 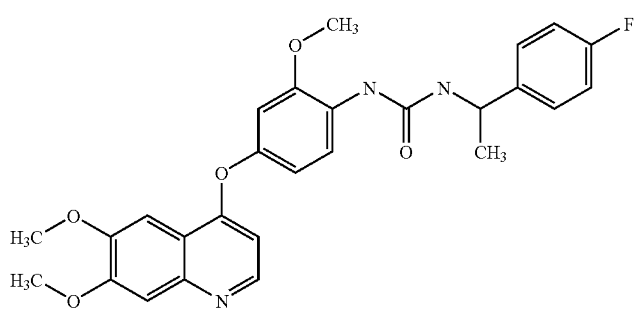 | 0.0020 |

TABLE 1-continued

| Example | Chemical structure | IC$_{50}$ (μm) |
|---|---|---|
| 17 | 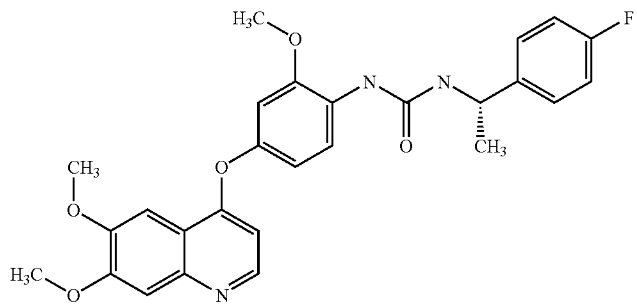 | 0.0039 |
| 18 | 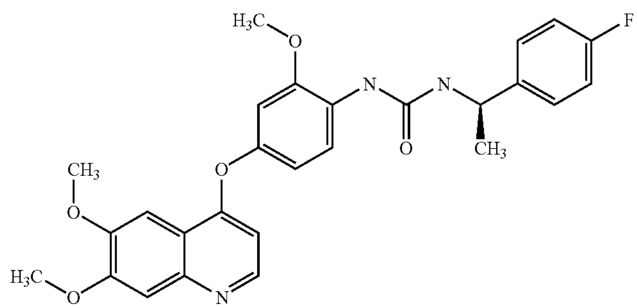 | 0.0037 |
| 19 | 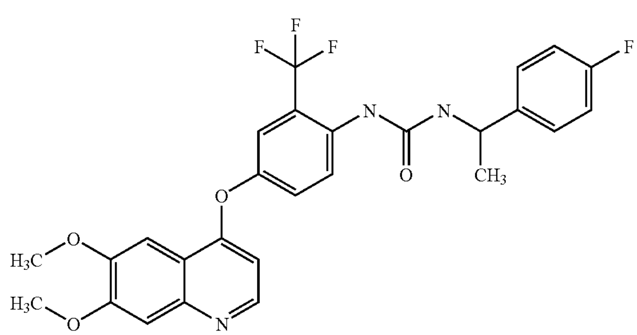 | 0.0081 |
| 20 | 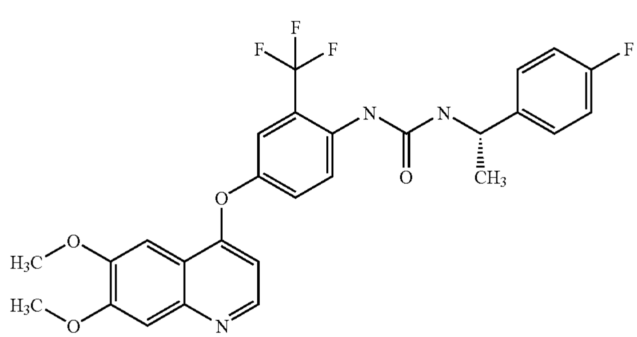 | 0.0062 |

TABLE 1-continued

| Example | Chemical structure | IC$_{50}$ (μm) |
|---|---|---|
| 21 | 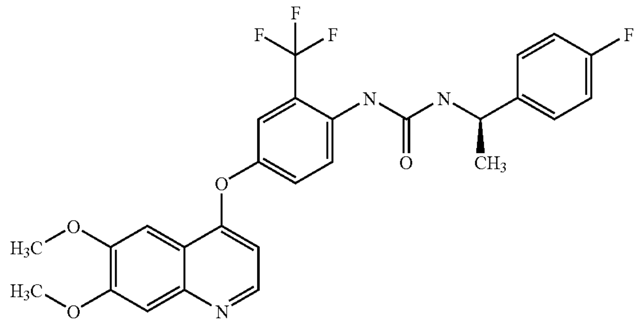 | 0.0098 |
| 22 | 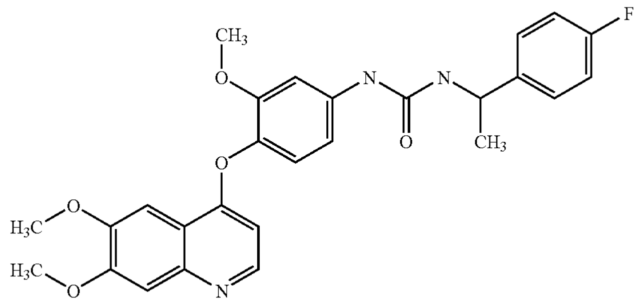 | 0.0077 |
| 23 | 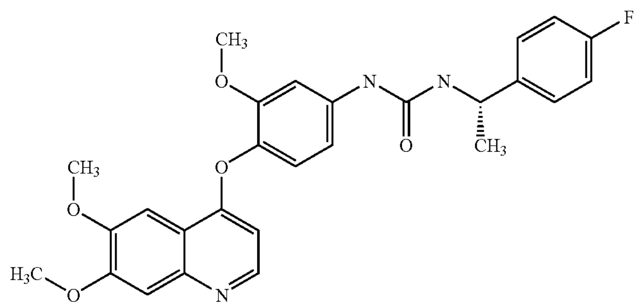 | 0.0102 |
| 24 | 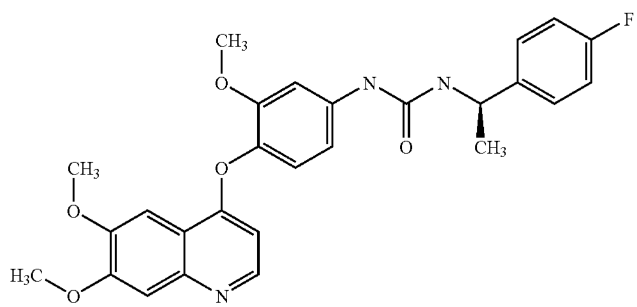 | 0.0132 |
| 25 | 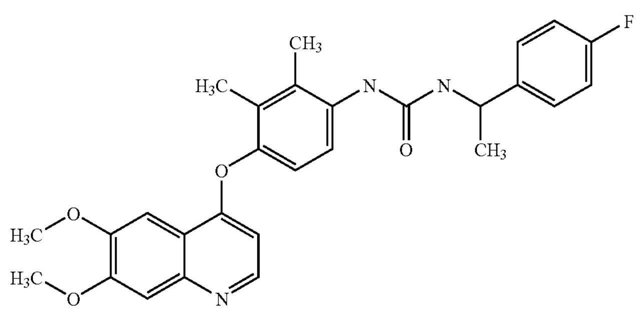 | 0.0219 |

TABLE 1-continued

| Example | Chemical structure | IC$_{50}$ (μm) |
|---|---|---|
| 26 | 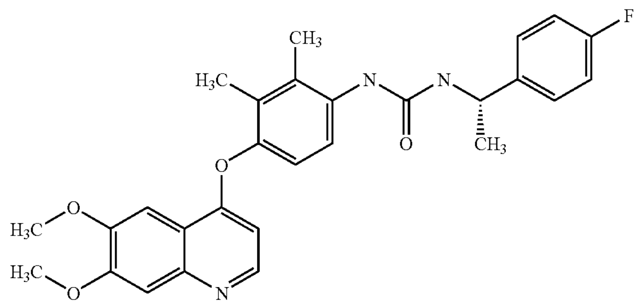 | 0.0163 |
| 27 | 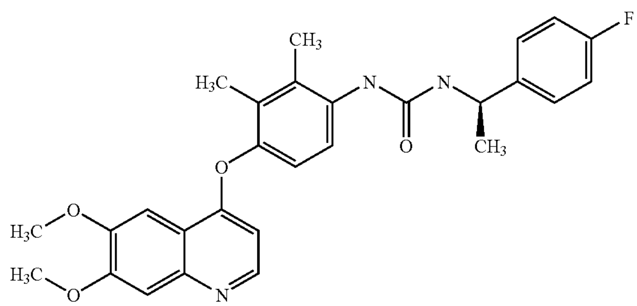 | 0.0076 |
| 28 | 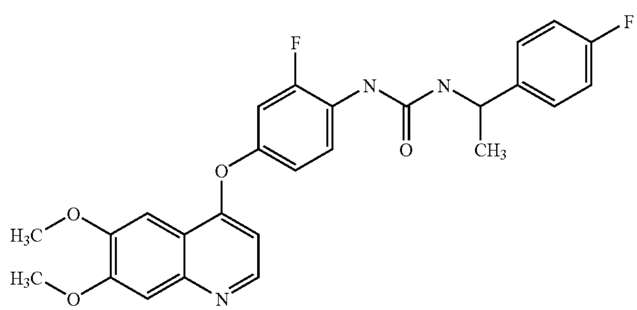 | 0.0065 |
| 29 | 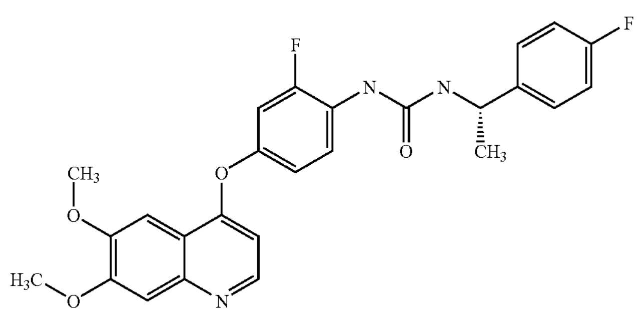 | 0.0023 |
| 30 | 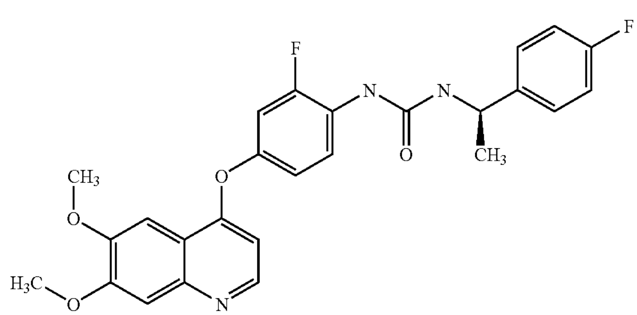 | 0.0031 |

TABLE 1-continued

| Example | Chemical structure | IC$_{50}$ (μm) |
|---|---|---|
| 31 | 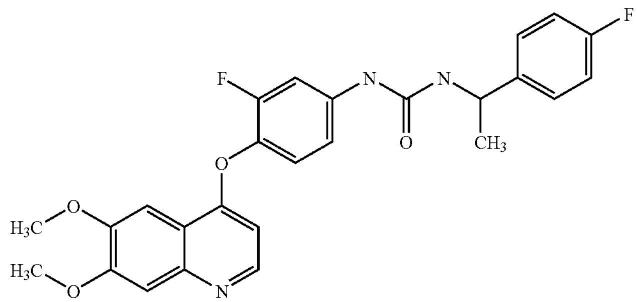 | 0.0129 |
| 32 | 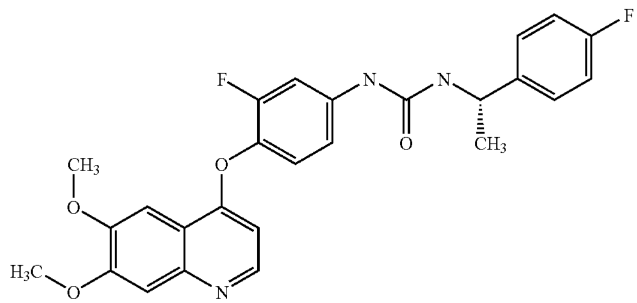 | 0.0035 |
| 33 | 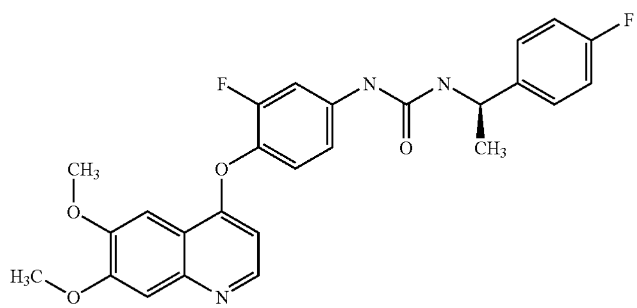 | 0.0065 |
| 34 | 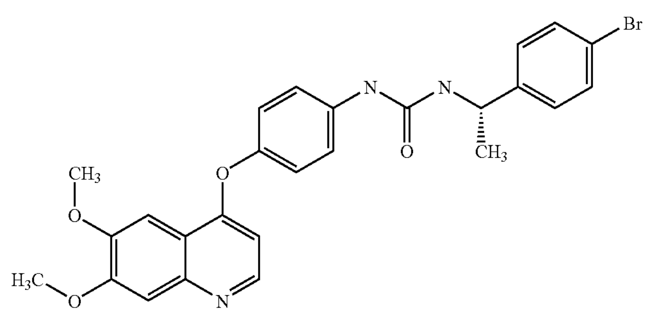 | 0.0063 |
| 35 | 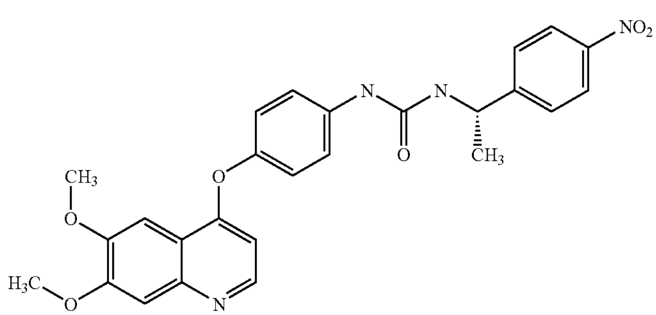 | 0.0121 |

TABLE 1-continued

| Example | Chemical structure | IC$_{50}$ (μm) |
|---|---|---|
| 36 | 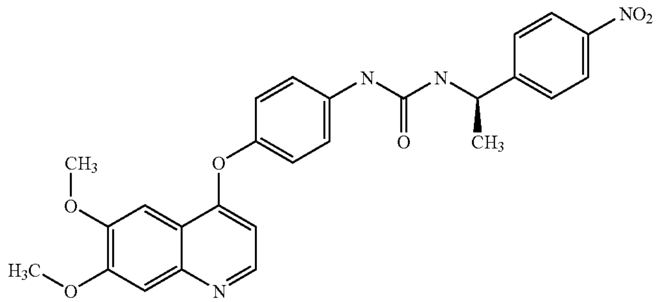 | 0.0311 |
| 37 | 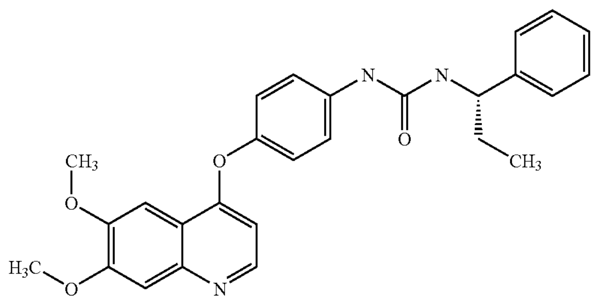 | 0.0050 |
| 38 | 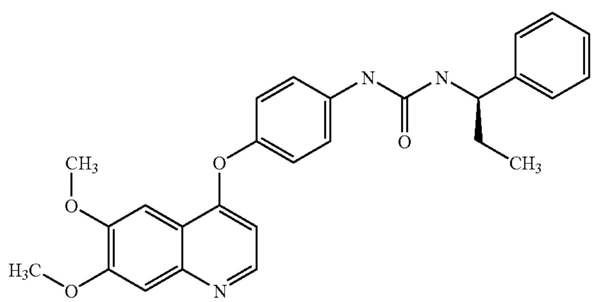 | 0.0057 |
| 41 | 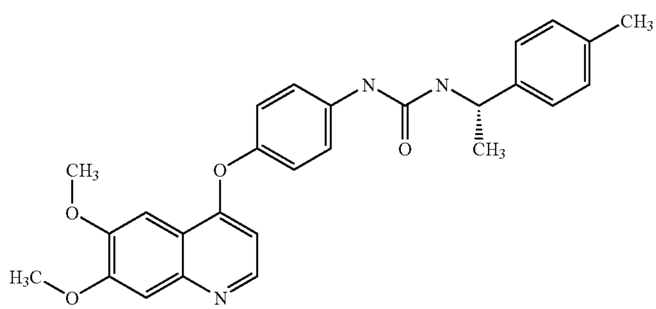 | 0.0028 |
| 42 | 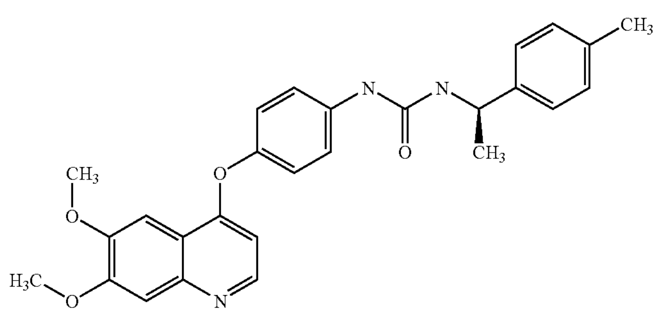 | 0.0385 |

TABLE 1-continued

| Example | Chemical structure | IC$_{50}$ (μm) |
|---|---|---|
| 43 | 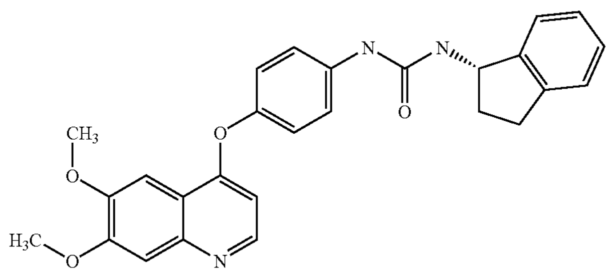 | 0.0031 |
| 44 | 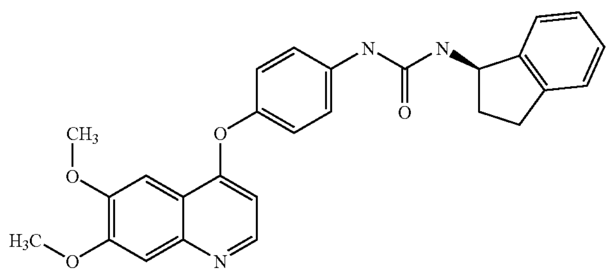 | 0.0018 |
| 45 | 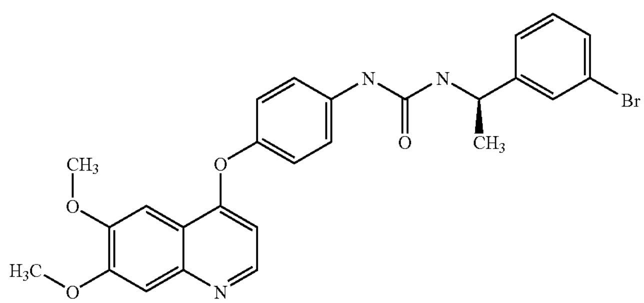 | 0.0222 |
| 46 | 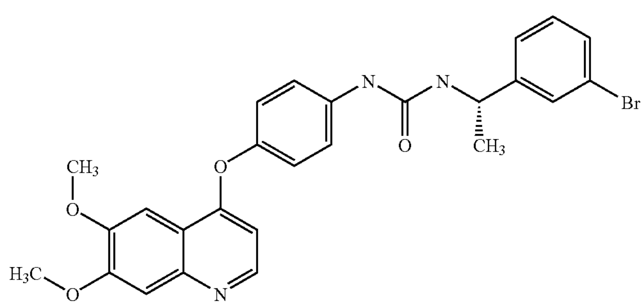 | 0.0073 |
| 47 | 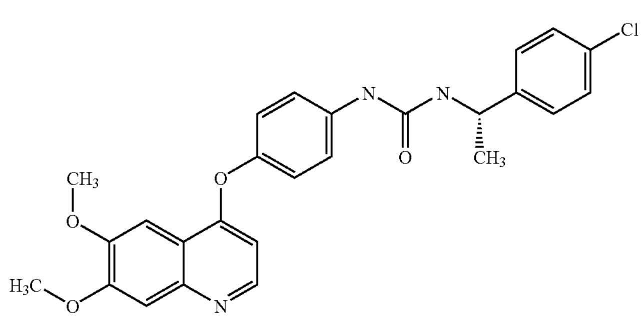 | 0.0038 |

TABLE 1-continued

| Example | Chemical structure | IC$_{50}$ (μm) |
|---|---|---|
| 48 | 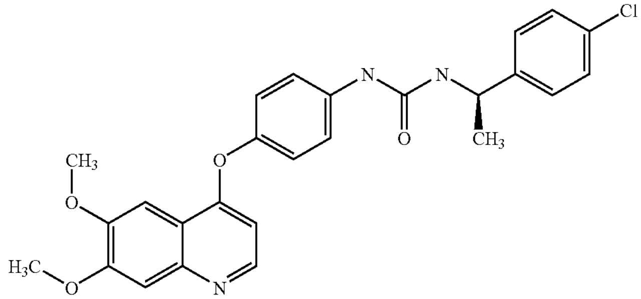 | 0.0400 |
| 49 | 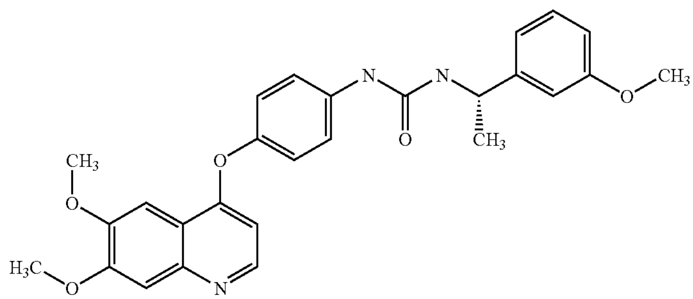 | 0.0032 |
| 50 | 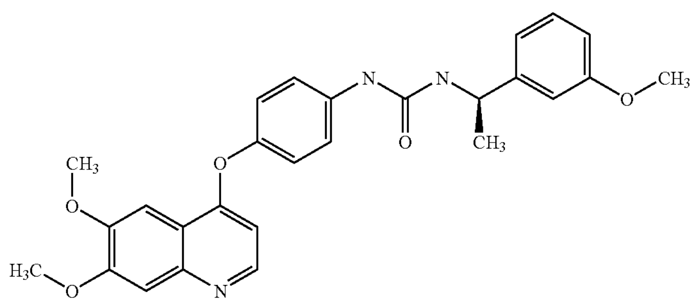 | 0.0072 |
| 51 | 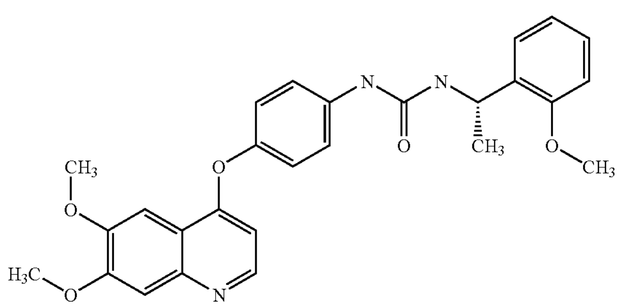 | 0.0076 |
| 52 | 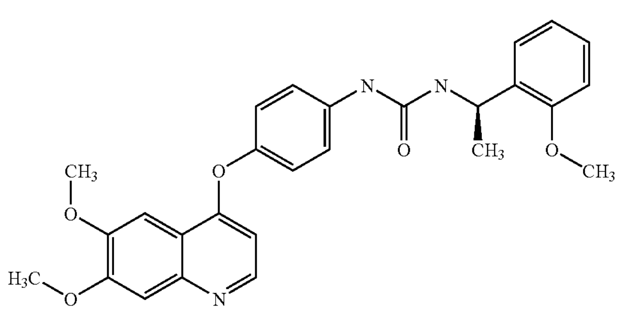 | 0.0055 |

TABLE 1-continued

| Example | Chemical structure | IC$_{50}$ (μm) |
|---|---|---|
| 53 | 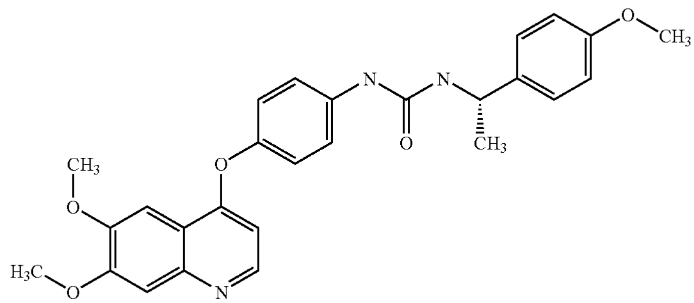 | 0.0027 |
| 54 | 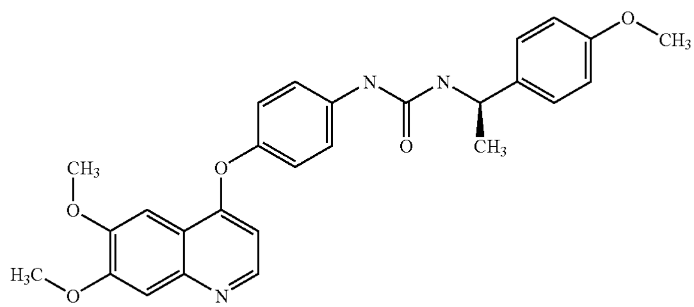 | 0.0695 |
| 55 | 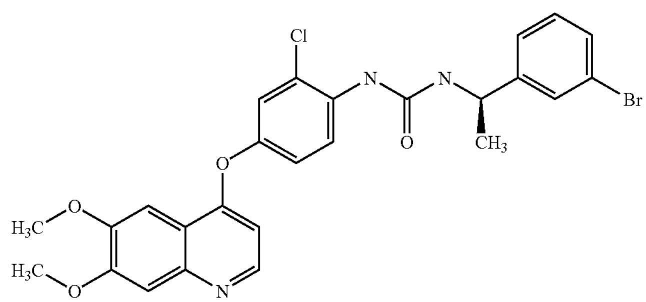 | 0.0454 |
| 56 | 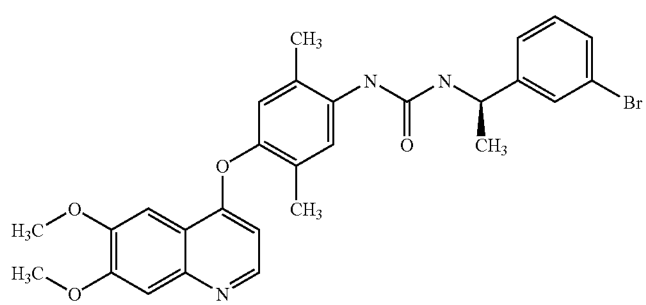 | 0.1933 |
| 57 | 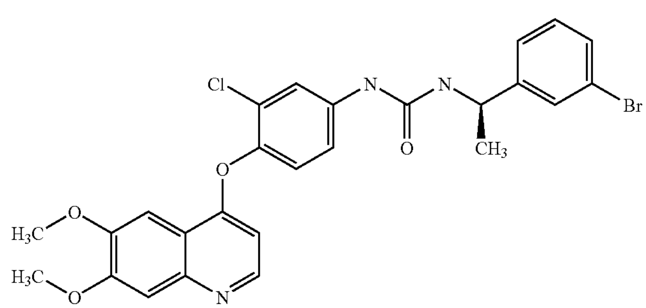 | 0.1275 |

TABLE 1-continued
| Example | Chemical structure | IC$_{50}$ (μm) |
|---|---|---|
| 58 | 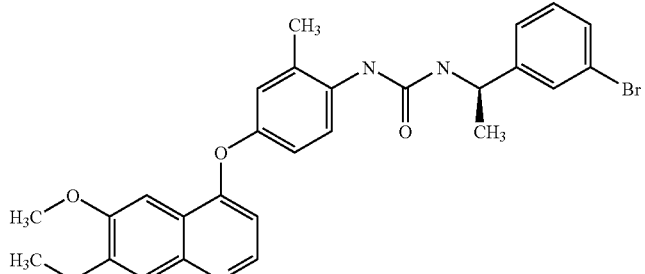 | 0.0809 |
| 59 | 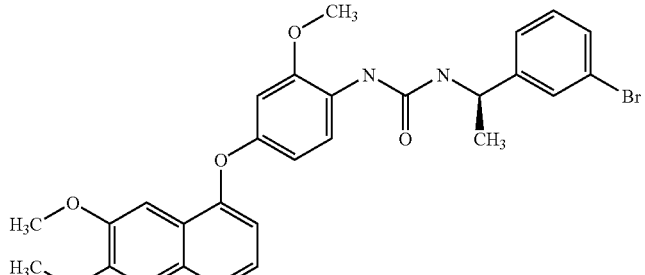 | 0.0203 |
| 60 | 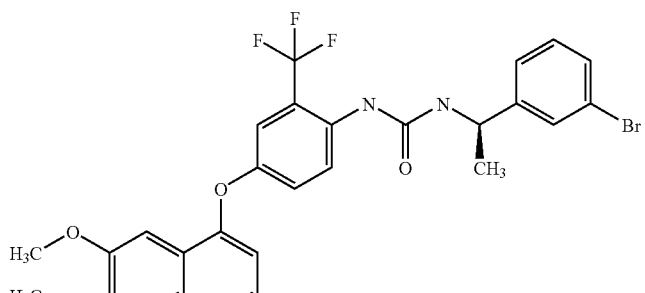 | 0.1152 |
| 61 | 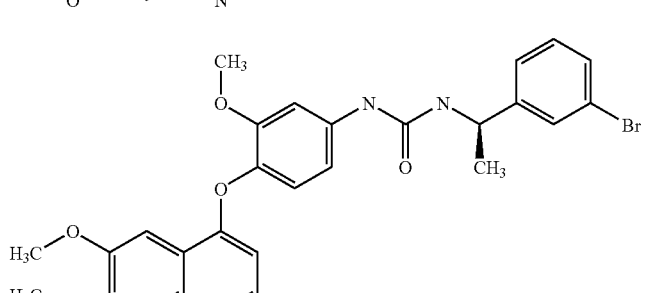 | 0.0443 |
| 62 | 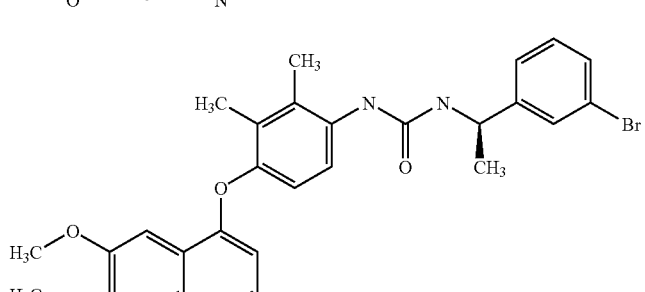 | 0.0294 |

TABLE 1-continued

| Example | Chemical structure | IC$_{50}$ (μm) |
|---|---|---|
| 63 | 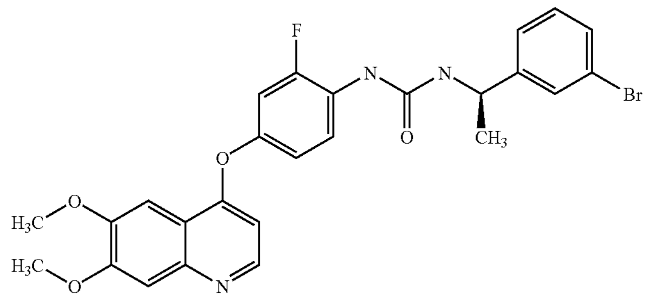 | 0.0309 |
| 64 | 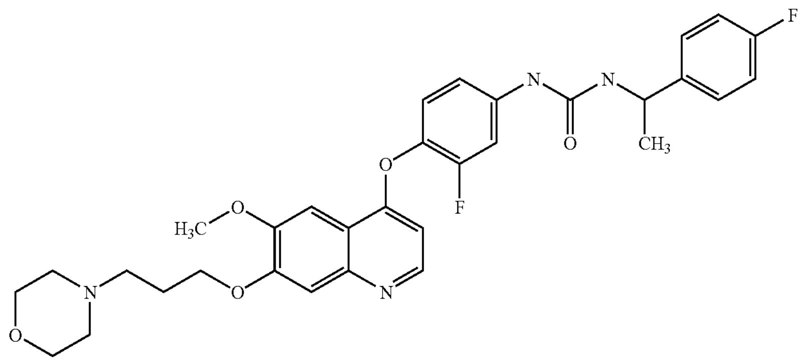 | 0.0094 |
| 65 | 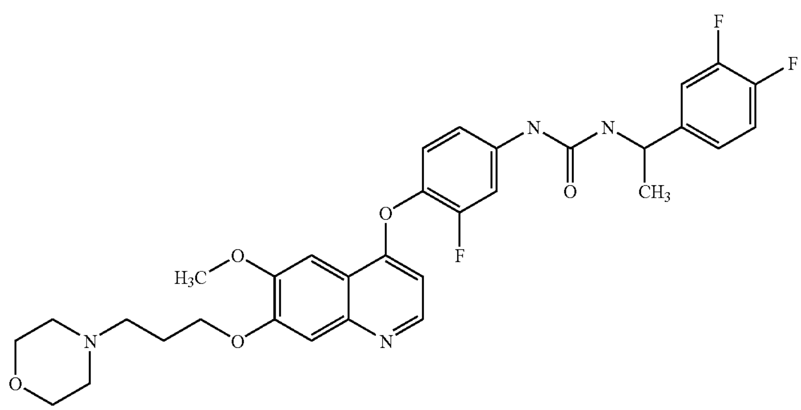 | 0.0139 |
| 66 | 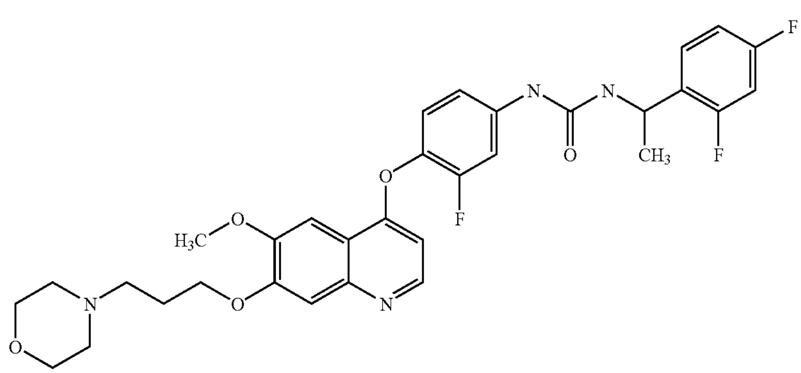 | 0.0147 |

TABLE 1-continued
| Example | Chemical structure | IC$_{50}$ (μm) |
|---|---|---|
| 67 | 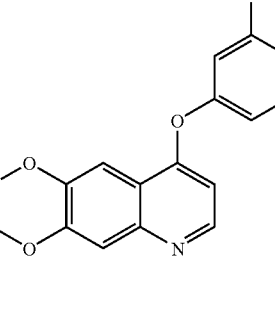 | 0.0057 |
| 68 | 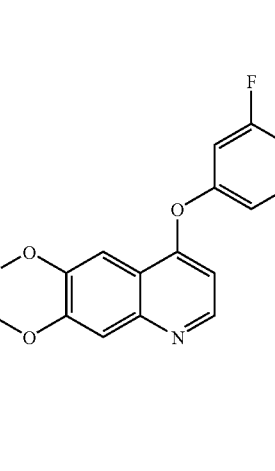 | 0.0098 |
| 69 | 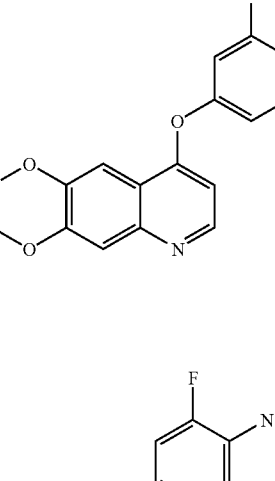 | 0.0115 |
| 70 | 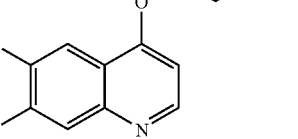 | 0.0036 |

TABLE 1-continued

| Example | Chemical structure | IC$_{50}$ (μm) |
|---|---|---|
| 71 | (6,7-dimethoxyquinolin-4-yloxy)-2-fluorophenyl urea with (S)-1-(thiazol-2-yl)ethyl | 0.0030 |
| 72 | (6,7-dimethoxyquinolin-4-yloxy)-2-fluorophenyl urea with 1-(thiazol-2-yl)ethyl | 0.0049 |
| 73 | 4-(6,7-dimethoxyquinolin-4-yloxy)-3-fluorophenyl urea with 1-(thiazol-2-yl)ethyl | 0.0030 |
| 74 | 4-(6,7-dimethoxyquinolin-4-yloxy)-2-methoxyphenyl urea with 1-(thiazol-2-yl)ethyl | 0.0050 |
| 75 | 4-(6,7-dimethoxyquinolin-4-yloxy)-2-methoxyphenyl urea with (S)-1-(thiazol-2-yl)ethyl | 0.0021 |

TABLE 1-continued

| Example | Chemical structure | IC$_{50}$ (μm) |
|---|---|---|
| 76 | 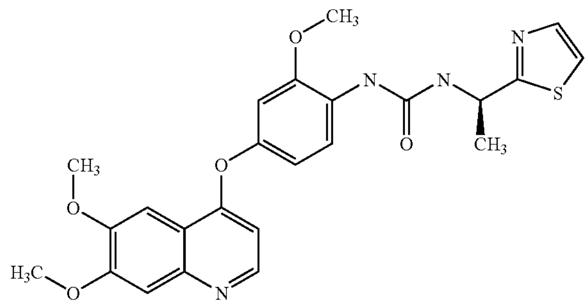 | 0.0071 |
| 77 | 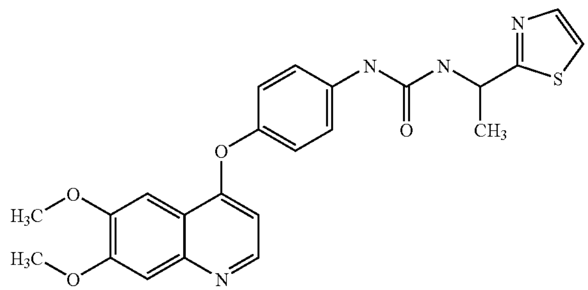 | 0.0047 |
| 78 | 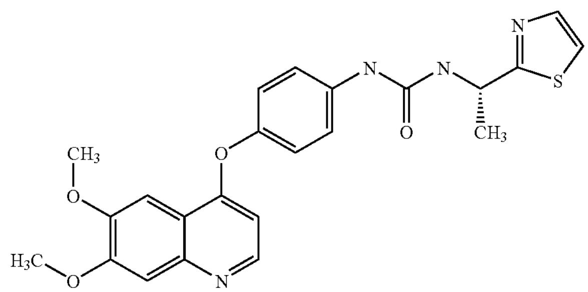 | 0.0029 |
| 79 | 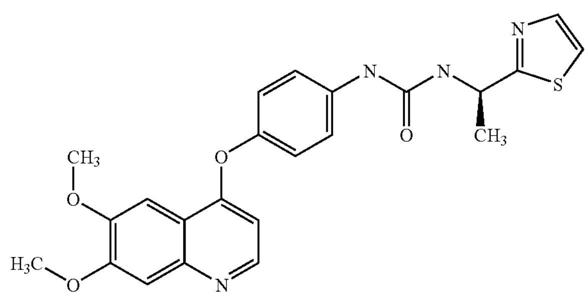 | 0.0069 |
| 80 | 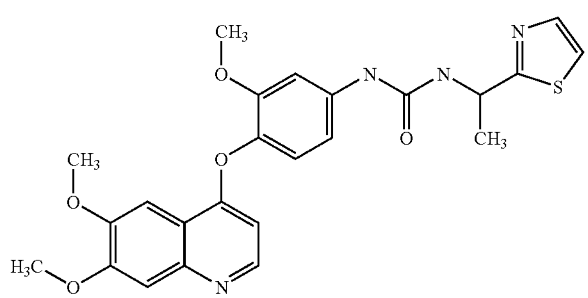 | 0.0062 |

TABLE 1-continued

| Example | Chemical structure | IC$_{50}$ (μm) |
|---|---|---|
| 81 | 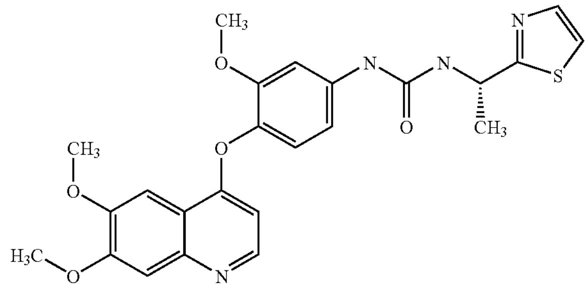 | 0.0062 |
| 82 | 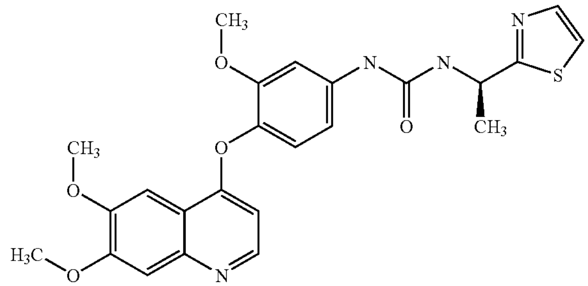 | 0.0089 |
| 83 | 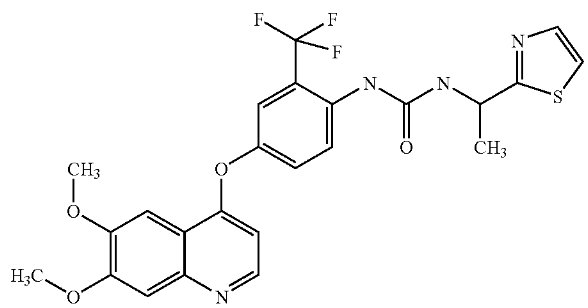 | 0.0102 |
| 84 | 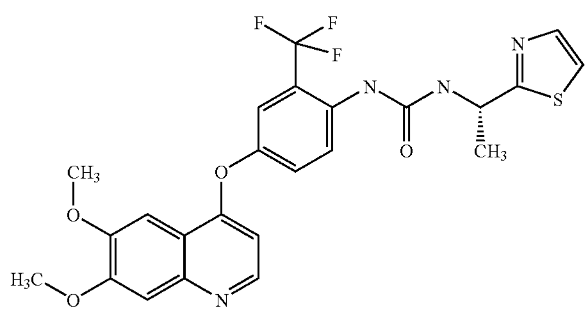 | 0.0102 |
| 85 | 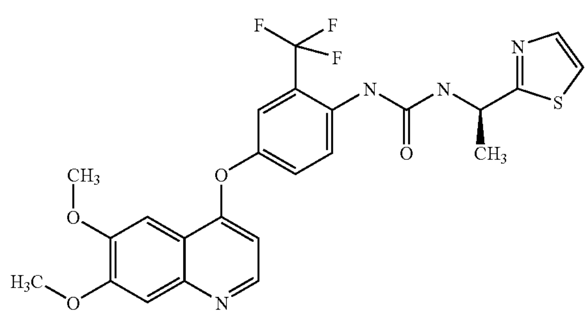 | 0.0174 |

TABLE 1-continued

| Example | Chemical structure | IC$_{50}$ (μm) |
|---|---|---|
| 86 | 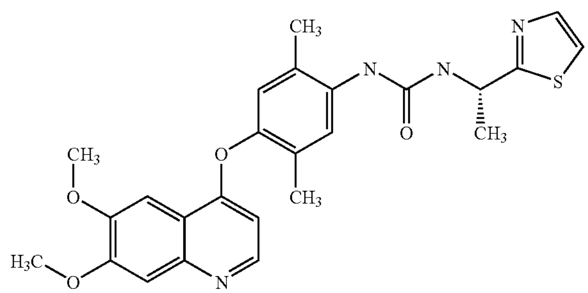 | 0.0125 |
| 87 | 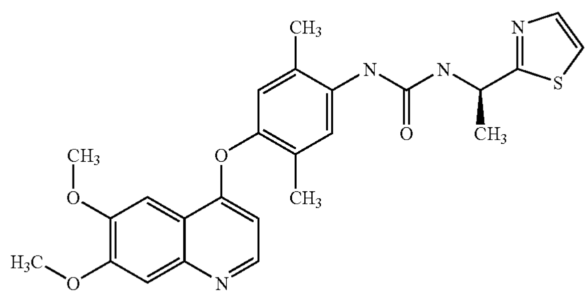 | 0.0265 |
| 88 | 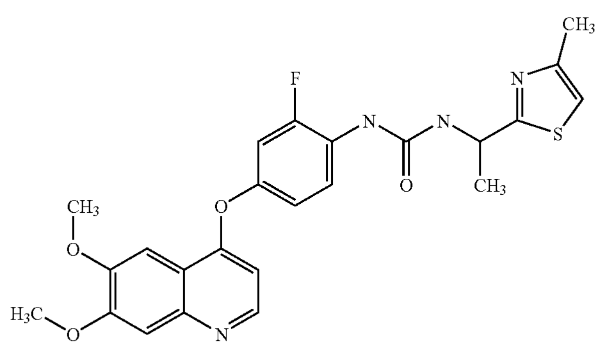 | 0.0029 |
| 89 | 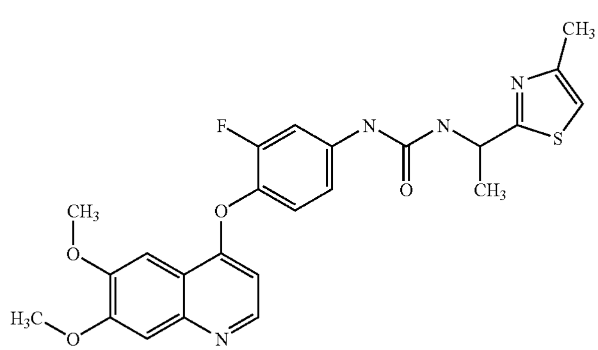 | 0.0031 |

TABLE 1-continued

| Example | Chemical structure | IC$_{50}$ (μm) |
|---|---|---|
| 90 | 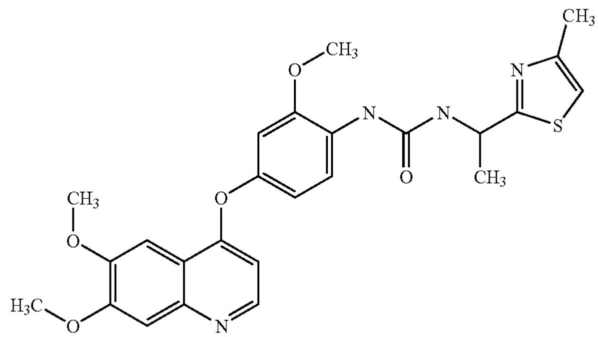 | 0.0036 |
| 91 | 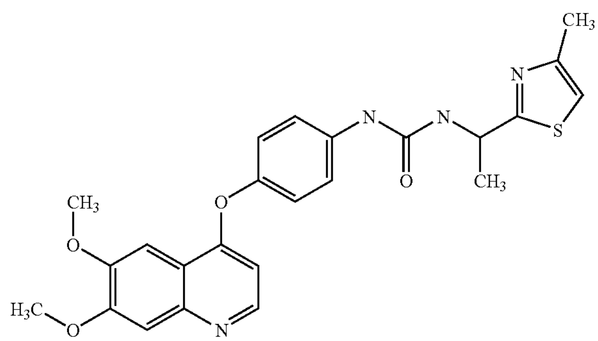 | 0.0032 |
| 92 | 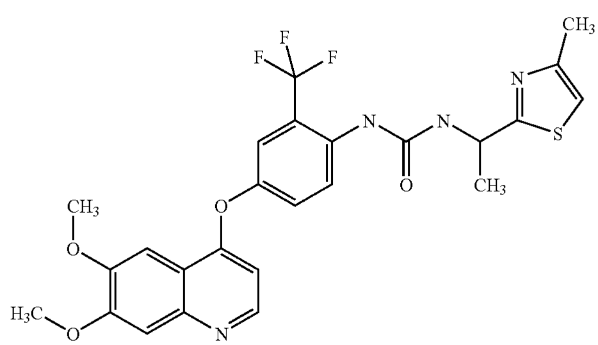 | 0.0084 |
| 93 | 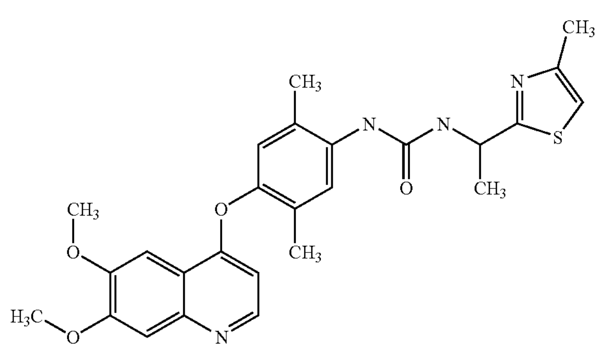 | 0.0386 |

TABLE 1-continued
| Example | Chemical structure | IC$_{50}$ (μm) |
|---|---|---|
| 94 | 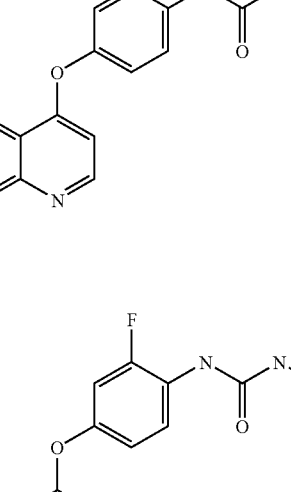 | 0.0535 |
| 95 | 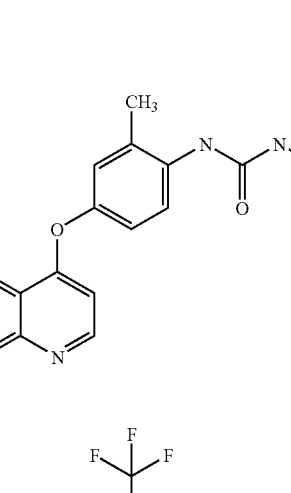 | 0.0383 |
| 96 | 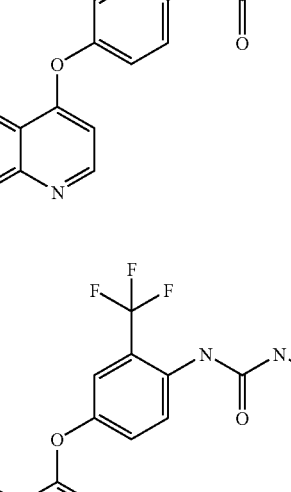 | 0.1468 |
| 97 | 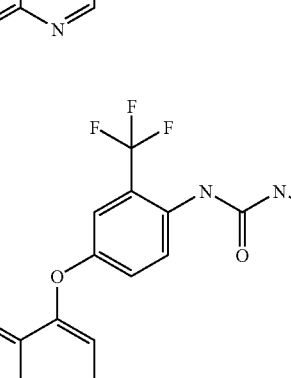 | 0.1202 |

TABLE 1-continued

| Example | Chemical structure | IC$_{50}$ (μm) |
|---------|-------------------|----------------|
| 98 | 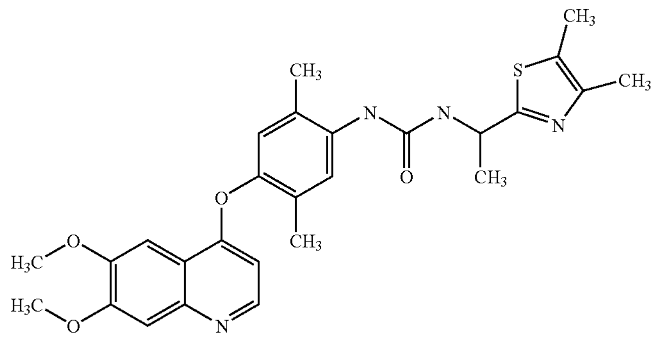 | 0.4260 |
| 99 | 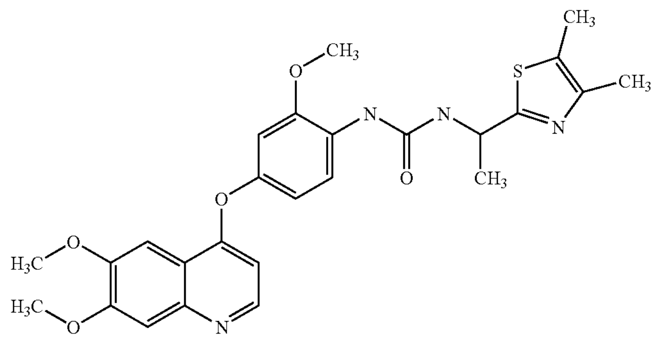 | 0.0126 |
| 100 | 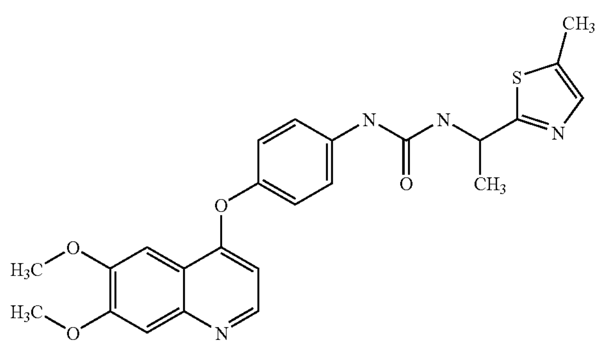 | 0.0157 |
| 101 | 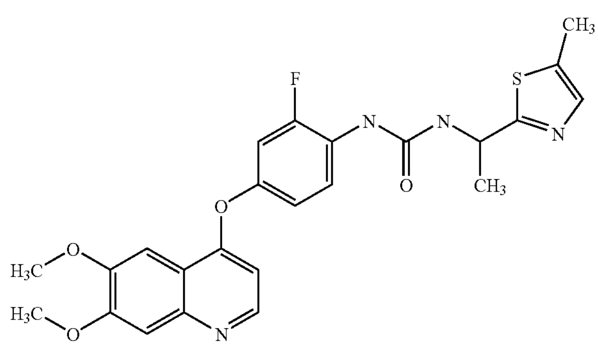 | 0.0201 |

TABLE 1-continued

| Example | Chemical structure | IC$_{50}$ (μm) |
|---|---|---|
| 102 | 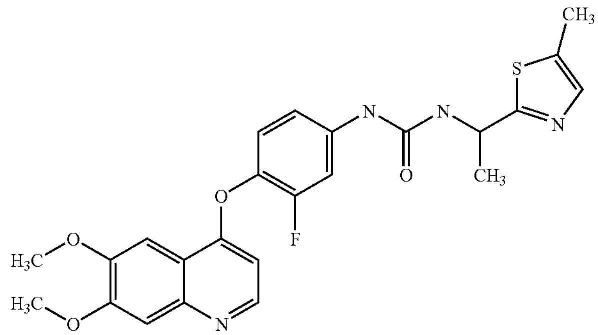 | 0.0203 |
| 103 | 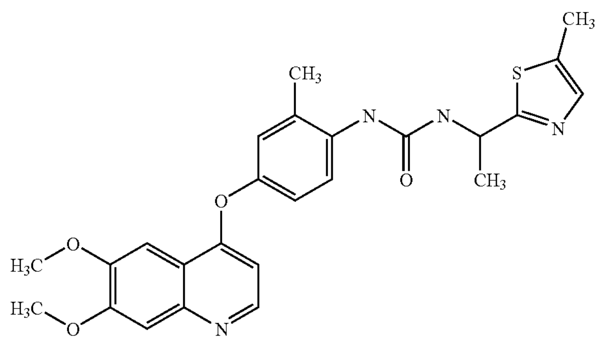 | 0.0696 |
| 104 | 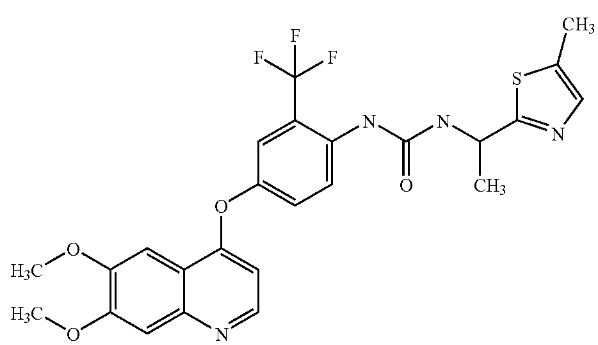 | 0.0220 |
| 105 | 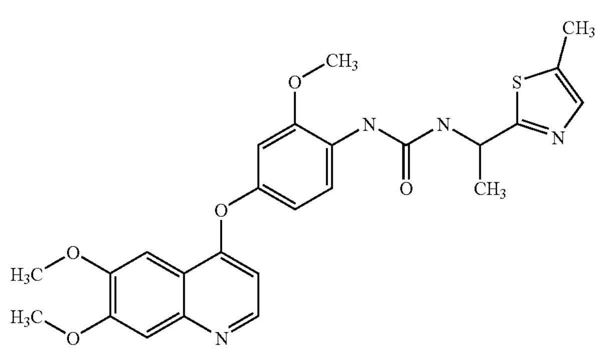 | 0.0127 |

Pharmacological Test Example 1

Measurement of Inhibitory Activity Against c-fms Tyrosine Kinase Activity within Macrophage-Like Cell Line BAC-1.2F5 by M-CSF Stimulation Macrophage-like cell line BAC-1.2F5 which expresses c-fms as a M-CSF receptor on cell membranes (CLAUDIA M. et al., J. Cell. Physiol., 130, 420-427 (1987), "Isolation and Characterization of a Cloned Growth Factor Dependent Macrophage Cell Line, BAC1.2F5") was cultured at 37° C. in a DMEM medium containing L-cell supernatant and 10% fetal calf serum (GIBCO BRL) in a 5% $CO_2$ incubator until about 50 to 70% confluent. The harvested cells were inoculated into wells, each containing the same medium, in a collagen type I coat 96-well flat-bottom plate in an amount of $5.0 \times 10^4$ per well, and cultured at 37° C. for 12 hr. Thereafter, the medium was replaced with a DMEM medium containing a 0.1% fetal calf serum and cultured for 12 hr. Thereafter, a test compound dissolved in dimethyl sulfoxide was added to each well, and cells were incubated at 37° C. for one hr. Human recombinant M-CSF was added to a final concentration of 50 ng/ml, and cells were stimulated at 37° C. for 6 min. After the medium was removed, 50 µl of a solubilization buffer (20 mM HEPES (pH 7.4), 150 mM NaCl, 0.2% Triton X-100, 10% glycerol, 5 mM sodium orthovanadylate, 5 mM disodium ethylenediaminetetraacetate, and 2 mM $Na_4P_2O_7$) was added thereto. The mixture was shaken at 4° C. for 2 hr to prepare a cell extract as an assay sample which was then used for an ELISA assay.

The plate for the ELISA assay was prepared as follows. Phosphate buffered saline (50 µl, pH 7.4) containing 5 µg/ml of anti-phospho-tyrosine antibody (PY20; Transduction Laboratories) was added to a microplate for ELISA (Maxisorp; purchased from NUNC), followed by standing at 4° C. overnight to be immobilized on the wells. Thereafter, each well was washed twice with 200 µl of a Ca- and Mg-free phosphate buffer containing 0.1% Tween-20 (hereinafter referred to as "PBS-T"), and 200 µl of a blocking solution (Dainippon Pharmaceutical Co. Ltd.: BlockAce) was added to each well, and the wells were then allowed to stand at room temperature for 2 hr for blocking.

Separately, phosphate buffered saline (50 µl, pH 7.4) containing 5 µg/ml of anti-phospho-tyrosine antibody (PY20; Transduction Laboratories) was added to a microplate for ELISA (Maxisorp; purchased from NUNC), followed by standing at 4° C. overnight to form a solid phase on the wells. After washing of the plate, 300 µl of a blocking solution was added, followed by standing at room temperature for 2 hr to perform blocking. After washing, the whole quantity of the cell extract was transferred to the wells, and the plate was then allowed to stand at 4° C. overnight. After washing, anti-c-fms antiserum (Upstate Biotechnology, Inc.) was allowed to react at room temperature for one hr, and, after washing, a peroxidase-labeled anti-rabbit Ig antibody (Amersham) was allowed to react at room temperature for one hr. After washing, a chromophoric substrate for peroxidase (Sumitomo Bakelite Co., Ltd.) was added thereto to initiate a reaction. After a suitable level of color development, a reaction termination solution was added to stop the reaction, and the absorbance at 450 nm was measured with a microplate reader. The c-fms phosphorylation activity for each well was determined by presuming the absorbance without the addition of the test compound and with the addition of M-CSF to be 100% c-fms phosphorylation activity and the absorbance without the addition of the test compound and M-CSF to be 0% c-fms phosphorylation activity. The concentration of the test compound was varied on several levels, the c-fms phosphorylation inhibitory rate was determined for each case, and the concentration of the test compound necessary for inhibiting 50% of c-fms phosphorylation ($IC_{50}$) was calculated. The results were as shown in the table described before.

Pharmacological Test Example 2

Measurement of Inhibitory Activity Against M-CSF-Dependent Cell Growth of Macrophage-Like Cell Line BAC-1.2F5

Macrophage-like cell line BAC-1.2F5 which expresses c-fms as a M-CSF receptor on cell membranes (CLAUDIA M. et al., J. Cell. Physiol., 130, 420-427 (1987), "Isolation and Characterization of a Cloned Growth Factor Dependent Macrophage Cell Line, BAC1.2F5") was cultured at 37° C. in a DMEM medium containing L-cell supernatant and 10% fetal calf serum (purchased from GIBCO BRL) in a 5% $CO_2$ incubator until about 50 to 70% confluent. The harvested cells were inoculated into wells, each containing a 10% fetal calf serum-containing DMEM medium with human recombinant M-CSF being added thereto to a final concentration of 50 ng/ml, in a 96-well flat-bottom plate at a density of $5.0 \times 10^3$ per well, and cultured at 37° C. for 24 hr. A test compound dissolved in dimethyl sulfoxide was then added to each well to a target concentration, and cells were incubated at 37° C. in a 5% $CO_2$ incubator for 72 hr. Thereafter, 20 µl of an MTS reagent (purchased from Promega) was added to each well, followed by incubation at 37° C. in a 5% $CO_2$ incubator for 2 hr. Thereafter, absorbance at 490 nm was measured with a microplate reader. The cell growth rate with the addition of the test compound was determined by presuming the absorbance without the addition of the test compound and with the addition of M-CSF to be 100% cell growth and the absorbance without the addition of the test compound and M-CSF to be 0% cell growth. The concentration of the test compound was varied on several levels, and the cell growth rate in each case was calculated. As a result, a group of compounds according to the present invention inhibited M-CSF-dependent cell growth of BAC-1.2F5 cell line in a concentration-dependent manner. A representative example thereof is shown in FIG. 1.

Pharmacological Test Example 3

Osteoclast Differentiation-Inducing Test by Cocultivation of Mouse Bone Marrow Cells and Cell Line for Osteoblasts Mouse osteoblast-like cell line KS483 (YAMASHITA T. et al., Bone, 19, 429-436 (1996), "Subcloning of Three Osteoblastic Cell with Distinct Differentiation Phenotypes from the Mouse Osteoblastic Cell line KS-4") was cultured in an α-MEM medium containing a 10% fetal calf serum (purchased from GIBCO BRL) until about 90% confluent. The cells were seeded into wells, each containing the same medium containing a 10% fetal calf serum, in a 48 well flat-bottom plate at a density of $2.0 \times 10^3$ per well. Bone marrow cells harvested from femorotibialis of 4-week old male DDY mice (purchased from Japan SLC, Inc.) were seeded into the same wells in which KS483 was cultured at a density of $2.0 \times 10^4$ per well, and $1,25(OH)_2VD_3$ was added to a final concentration of $10^{-8}$ mol/L. Further, the test compound dissolved in dimethyl sulfoxide was added to each well to a target concentration, followed by incubation in a 5% $CO_2$ incubator at 37° C. for 6 days. The medium was replaced every two days, and each time the replacement was carried out, $1,25(OH)_2VD_3$ and the test compound were added to the above concentration. Staining (ACID PHOSPHATASE LEUKOCYTE; SIGMA) and observation were carried out after cultivation for 6 days using tartaric acid-resistant acid phosphatase (hereinafter referred to as "TRAP") activity (a specific marker found on the surface of osteoclast cell) as an index. After staining, observation under an optical microscope was carried out. As a result, it was found that a group of compounds according to the present invention reduced the number of osteoclasts stained by TRAP activity in a concentration-dependent manner. At the same time, the TRAP activity was evaluated by the measurement of enzyme activity using p-nitrophenylphosphate (SIGMA104 phosphatase substrate; SIGMA; hereinafter referred to as "PNP"). The measurement of enzyme activity was carried out with PNP as follows. The medium in each well was removed after 6 days culture, and cells were fixed with an acetone-water-citrate buffer (weight ratio=15:9:1) mixed solution. After washing, PNP was dissolved in a water-acetate buffer-tartrate buffer (weight ratio=22:1:1) mixed solution to a final concentration of 0.4 mg/ml. This PNP solution was added to each well and was stirred at room temperature for one hr. After stirring, 50 µl of 0.5 N NaOH was further added, and 100 µl of the reaction solution in each well was dispensed in a 96 well flat-bottom plate, and absorbance at 405 nm was then measured with a microplate reader. For each well, TRAP activity was measured by presuming the absorbance in the case of culture without the addition of the test compound and with the addition of only KS483 and mouse bone marrow cells in the presence of $1,25(OH)_2VD_3$ to 100% TRAP activity and the absorbance without the addition of the test compound and the mouse bone marrow cells to 0% TRAP activity. The concentration of the test compound was varied on several levels, and, for each case, the rate of inhibition against TRAP activity was determined. As a result, a group of compounds according to the present invention reduced TRAP activity in a concentration-dependent manner. That is, the differentiation of osteoclasts was inhibited in a dose-dependent manner. A typical example thereof is shown in FIG. 2.

Pharmacological Test Example 4

Inhibitory Effect in Nude Mouse Bone Metastasis Model Using Human Melanoma Cells (A375)

An A375 human melanoma cell line (obtained from Japanese Foundation for Cancer Research) was inoculated under anesthesia with Ketamine-Medetomidine into the left ventricle of nude mice to $1.0 \times 10^5$ cells/head, and, on the day of transplantation, the mice were grouped so that the groups each consisted of five mice and had an identical body weight. From the next day of the transplantation, for 28 days twice a day, the test compound was orally administered to the treatment group at 40 mg/kg/day, and the medium was orally administered to the control group. On 21 and 28 days after the transplantation, the mice were radiographed. For the images thus obtained, the bone resorption pore area in femora and fibiae attributable to bone metastasis of melanoma in each individual were calculated with an image analysis software (Image Gauge, FUJI FILM) to determine the average value for each group. The drug efficacy was evaluated by comparing the area of the test compound administered group with the area of the control group. As a result, a group of compounds according to the present invention were found to inhibit the expansion of the area of bone resorption attributable to bone metastatic melanoma cells. A representative example thereof is shown in FIG. 3.

Pharmacological Test Example 5

Inhibitory Effect in Nude Rat Bone Metastasis Model Using Human Melanoma Cells (A375)

Figure 4:
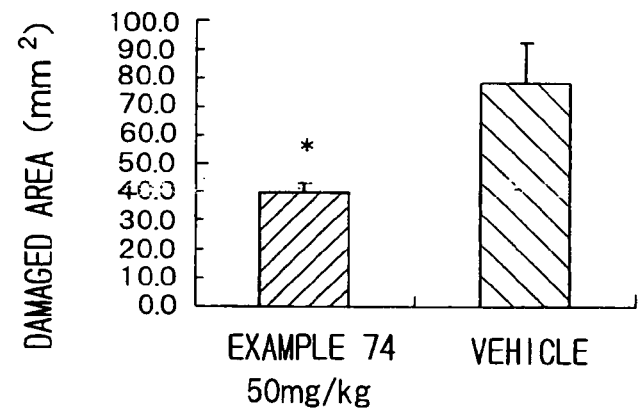
FIG. 4 is a diagram showing the effect of inhibiting the expansion of bone resorption area involved in bone metastasis of melanoma of compounds according to the present invention in a nude rat bone metastasis model, wherein the values are average value±SE, and *: $p<0.05$ (vs. vehicle control)

An A375 human melanoma cell line (obtained from Japanese Foundation for Cancer Research) was inoculated under anesthesia with Ketamine-Medetomidine into the left ventricle of nude mice to $5.0 \times 10^5$ cells/head, and, on the day of transplantation, the mice were grouped so that the groups each consisted of eight mice and had an identical body weight. From the next day of the transplantation, for 21 days once a day, the test compound was orally administered to the treatment group at 50 mg/kg, and the vehicle was orally administered to the control group. On 21 day after the transplantation, the mice were radiographed. For the images thus obtained, the femorotibial bone resorption pore area attributable to bone metastasis of melanoma in each individual were calculated with an image analysis software (Image Gauge, FUJI FILM) to determine the average value for each group. The drug efficacy was evaluated by comparing the area of the test compound administered group with the area of the control group. As a result, a group of compounds according to the present invention were found to inhibit the expansion of the area of bone resorption attributable to bone metastatic melanoma cells. A representative example thereof is shown in FIG. 4.

Pharmacological Test Example 6

Effect of Inhibiting Increase in Number of Osteoclasts in Spayed Model Rats

Figure 5:
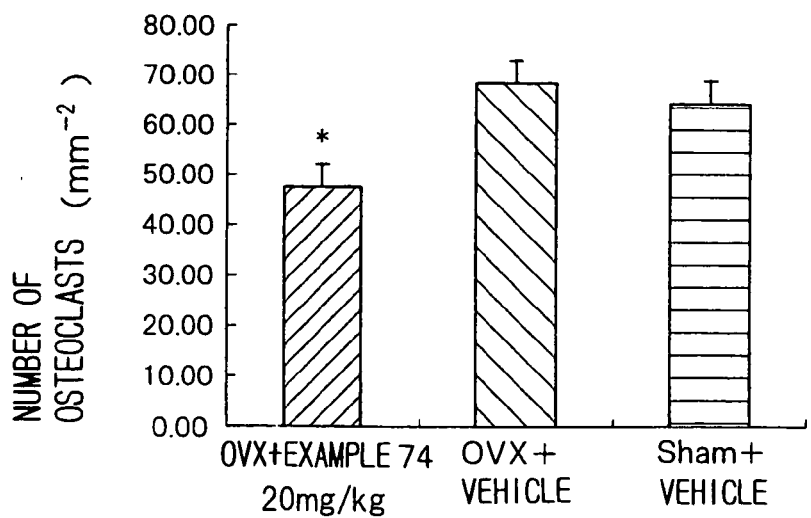
FIG. 5 is a diagram showing the effect of inhibiting an increase in the number of osteoclasts by a compound of the present invention in an ovariectomy model rats, wherein OVX represents a group of ovariectomy rats and Sham a group of sham operation rats; the values are average value±SE; and *: $p<0.05$ (vs. OVX-vehicle).

Six-week old female SD rats (purchased from Japan SLC, Inc.) were grouped so that the groups each consisted of six rats and had an identical body weight. On the 7th day after grouping, both ovaries were spayed to prepare an osteoporosis model. For 28 days from the day of grouping once a day, the test compound was orally administered at 20 mg/kg/day, and the vehicle was orally administered to the control group. On the 21st day after the transplantation, tibias of both feet were harvested and were fixed with 10% buffered formalin. Sections were then prepared, and TRAP staining was carried out. An optical microscope was interlocked with a personal computer, and the number of TRAP-positive osteoclasts in a primary cancellous zone of tibial metaphyseal part was measured with a bone form analysis software (Luzex F Bone System, NIRECO CORPORATION). TRAP-positive cells having two or more nuclei were regarded as osteoclasts. In the measurement, a line connecting one end of the growth cartilage to a metaphyseal junction (hereinafter referred to as "GCMJ") or a line which is parallel to a line connecting both ends of the growth cartilage in its lower part and is in contact with GCMJ is provided as a base line. A rectangular region showing an area of 0.96 mm² defined by about 0.4 mm from the base line toward shaft and, in the lateral direction, about 2.4 mm distant from GCMJ as the center was set as a measurement viewing field. As a result, a group of compounds according to the present invention significantly reduced the number of osteoclasts. A typical example thereof is shown in FIG. 5.

Pharmacological Test Example 7

Measurement of Inhibitory Activity Against KDR Phosphorylation Using ELISA Method Human KDR-transfected NIH3T3 cells (Sawano A et al., Cell Growth & Differentiation, 7, 213-221 (1996)) were cultured in a DMEM medium containing 10% fetal calf serum (purchased from GIBCO BRL) within a 5% carbon dioxide incubator until 50 to 70% confluent. The harvested cells were seeded into wells, containing the same medium, in a collagen type 1 coat 96-well flat-bottom plate in an amount of $1.5 \times 10^4$ per well, and cultured at 37° C. overnight. The medium was replaced with a 0.1% fetal calf serum-containing DMEM medium. The test compound dissolved in dimethyl sulfoxide was added to each well, and the cultivation was continued at 37° C. for additional one hr. A human recombinant vascular endothelial growth factor (hereinafter abbreviated to "VEGF") was added to a final concentration of 100 ng/ml, followed by stimulation of cells at 37° C. for 2 min. The medium was removed, and the cells were washed with phosphate buffered saline (pH 7.4). A solubilization buffer (50 µl) (20 mM HEPES (pH 7.4), 150 mM NaCl, 0.2% Triton X-100, 10% glycerol, 5 mM sodium orthovanadylate, 5 mM disodium ethylenediaminetetraacetate, and 2 mM $Na_4P_2O_7$) was then added thereto. The mixture was shaken at 4° C. for 2 hr to prepare a cell extract.

Separately, phosphate buffered saline (50 µl, pH 7.4) containing 5 µg/ml of anti-phospho-tyrosine antibody (PY20; purchased from Transduction Laboratories) was added to a microplate for ELISA (Maxisorp; purchased from NUNC), followed by standing at 4° C. overnight to be immobilized on the wells. After washing of the plate, 300 µl of a blocking solution was added, followed by standing at room temperature for 2 hr to perform blocking. After washing, the whole cell extract was transferred and was allowed to stand at 4° C. overnight. After washing, an anti-KDR antibody (purchased from Santa Cruz Biotechnology) was allowed to react at room temperature for one hr. Further, after washing, a peroxidase-labeled anti-rabbit Ig antibody (purchased from Amersham) was allowed to react at room temperature for one hr. After washing, a chromophoric substrate for peroxidase (purchased from Sumitomo Bakelite Co., Ltd.) was added thereto to initiate a reaction. After a suitable level of color development, a reaction termination solution was added to stop the reaction, and the absorbance at 450 nm was measured with a microplate reader. The KDR phosphorylation activity for each well was determined by presuming the absorbance without the addition of the test compound and with the addition of VEGF to be 100% KDR phosphorylation activity and the absorbance without the addition of the test compound and VEGF to be 0% KDR phosphorylation activity. The concentration of the test compound was varied on several levels, the KDR phosphorylation inhibitory rate was determined for each case, and the concentration of the test compound necessary for inhibiting 50% of KDR phosphorylation ($IC_{50}$) was calculated.

KDR phosphorylation 50% inhibitory concentration ($IC_{50}$) regarding typical examples of a group of compounds according to the present invention was as shown in Table 2. The selection ratio of the KDR phosphorylation inhibitory activity to the c-fms phosphorylation inhibitory activity is also shown in Table 2. When KDR phosphorylation 50% inhibitory concentration [µM]/c-fms phosphorylation 50% inhibitory concentration [µM] was less than 5, the selection ratio was indicated as "0"; when the value was 5 or more, the selection ratio was indicated as "1"; when the value was 10 or more, the selection ratio was indicated as "2"; and when the value was 50 or more, the selection ratio was indicated as "3."

TABLE 2

| Ex. No. | KDR (µM) | Selection ratio |
|---|---|---|
| 1 | 0.0011 | 0 |
| 2 | 0.0323 | 2 |
| 3 | <0.0010 | 0 |
| 4 | 0.0010 | 0 |
| 5 | 0.0214 | 1 |
| 6 | 0.0018 | 0 |
| 7 | 0.0031 | 0 |
| 8 | 0.3897 | 2 |
| 9 | 0.0027 | 0 |
| 10 | 0.0030 | 0 |
| 11 | 0.1232 | 2 |
| 12 | 0.0028 | 0 |
| 13 | <0.0010 | 0 |
| 14 | 0.0688 | 1 |
| 15 | <0.0010 | 0 |
| 16 | 0.0031 | 0 |
| 17 | 0.3149 | 3 |
| 18 | 0.0018 | 0 |
| 19 | 0.0015 | 0 |
| 20 | 0.1462 | 2 |
| 21 | 0.0021 | 0 |
| 22 | 0.0039 | 0 |
| 23 | 0.6000 | 3 |
| 24 | 0.0024 | 0 |
| 25 | 0.0035 | 0 |
| 26 | 0.1550 | 1 |
| 27 | 0.0020 | 0 |
| 28 | <0.0010 | 0 |
| 29 | 0.0273 | 2 |
| 30 | <0.0010 | 0 |
| 31 | 0.0010 | 0 |
| 32 | 0.0294 | 1 |
| 33 | <0.0010 | 0 |
| 34 | 0.2963 | 2 |
| 35 | 0.3097 | 2 |
| 36 | 0.1343 | 0 |
| 41 | 0.0188 | 1 |
| 42 | 0.0166 | 0 |
| 45 | 0.0025 | 0 |
| 46 | 0.5071 | 3 |
| 47 | 0.3097 | 3 |
| 48 | 0.0027 | 0 |
| 49 | 0.0454 | 2 |
| 50 | 0.0283 | 0 |
| 51 | 0.0382 | 1 |
| 52 | 0.0072 | 0 |
| 53 | 0.0374 | 2 |
| 54 | 0.5740 | 1 |
| 55 | 0.0016 | 0 |
| 56 | 0.0096 | 0 |
| 57 | 0.0036 | 0 |
| 58 | 0.0021 | 0 |
| 59 | 0.0087 | 0 |
| 60 | 0.0019 | 0 |
| 61 | 0.0192 | 0 |
| 62 | 0.0027 | 0 |
| 63 | 0.0026 | 0 |
| 64 | 0.0098 | 0 |
| 65 | 0.0319 | 0 |
| 66 | 0.0165 | 0 |
| 67 | 0.0029 | 0 |
| 68 | 0.0056 | 0 |
| 69 | 0.0052 | 0 |
| 70 | 0.0551 | 2 |
| 71 | 0.0399 | 2 |
| 72 | 0.0356 | 1 |
| 73 | 0.0433 | 2 |
| 74 | 0.3176 | 3 |
| 75 | 0.1463 | 3 |
| 76 | 0.4368 | 3 |

TABLE 2-continued

| Ex. No. | KDR (μM) | Selection ratio |
| --- | --- | --- |
| 77 | 0.1012 | 2 |
| 78 | 0.0539 | 2 |
| 79 | 0.0952 | 2 |
| 80 | 0.5257 | 3 |
| 81 | 1.0521 | 3 |
| 82 | 0.6501 | 3 |
| 83 | 0.0079 | 0 |
| 84 | 0.6609 | 3 |
| 85 | 0.0216 | 0 |
| 86 | 0.2081 | 2 |
| 87 | 0.2731 | 2 |
| 88 | 0.0087 | 0 |
| 89 | 0.0174 | 1 |
| 90 | 0.1110 | 2 |
| 91 | 0.0288 | 1 |
| 92 | 0.0043 | 0 |
| 93 | 0.2680 | 1 |
| 99 | 0.2924 | 2 |
| 100 | 0.3108 | 2 |
| 101 | 0.2387 | 2 |
| 102 | 0.2193 | 2 |
| 103 | 0.0909 | 0 |
| 104 | 0.0361 | 0 |
| 105 | 0.3096 | 2 |

Thus, the compounds according to the present invention have high c-fms phosphorylation inhibitory activity in vitro and selectively inhibit c-fms phosphorylation rather than KDR phosphorylation in vitro.

The invention claimed is:

1. A compound of formula (Ib) or a pharmaceutically acceptable salt thereof:

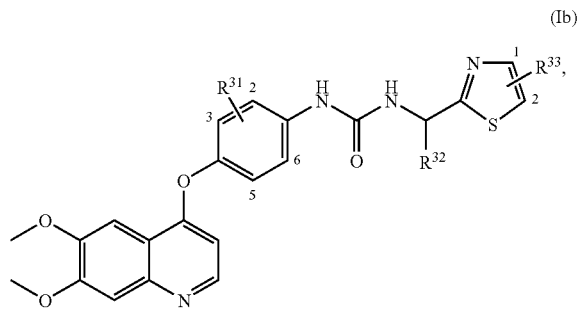

(Ib)

wherein
$R^{31}$ represents a hydrogen atom, a fluorine atom at 2-position, a fluorine atom at 3-position, methoxy at 2-position, methoxy at 3-position, or methyl at 2- and 5-positions,
$R^{32}$ represents methyl, and
$R^{33}$ represents a hydrogen atom, methyl at 1-position, methyl at 2-position, or methyl at 1- and 2-positions.

2. The compound according to claim 1, wherein the compound represented by formula (Ib) is represented by formula (Ib-I):

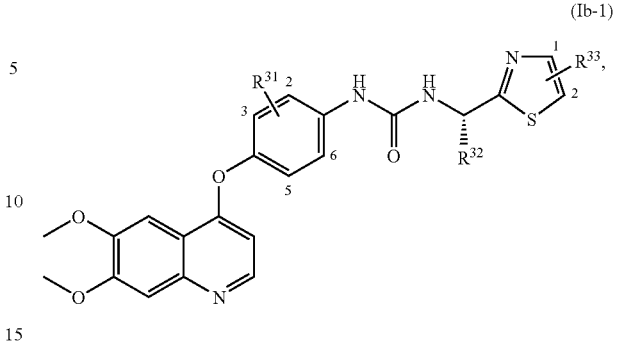

(Ib-1)

wherein $R^{31}$, $R^{32}$, and $R^{33}$ are as defined in formula (Ib).

3. The compound according to claim 1, wherein the compound represented by formula (Ib) is represented by formula (Ib-2):

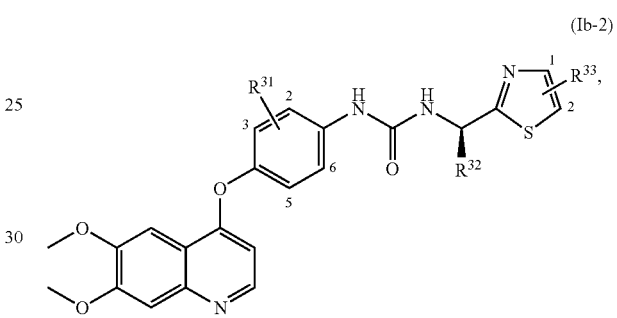

(Ib-2)

wherein $R^{31}$, $R^{32}$, and $R^{33}$ are as defined in formula (Ib).

4. A compound of formula (Ic) or a pharmaceutically acceptable salt thereof:

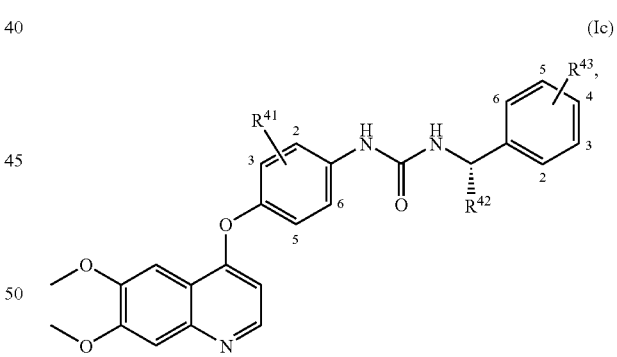

(Ic)

wherein
$R^{41}$ represents a hydrogen atom, a fluorine atom at 2-position, a fluorine atom at 3-position, a chlorine atom at 2-position, a chlorine atom at 3-position, methyl at 2- and 3-positions, methyl at 2- and 5-positions, methoxy at 2-position, methoxy at 3-position, methyl at 2-position, or trifluoromethyl at 2-position,
$R^{42}$ represents methyl,
$R^{43}$ represents a fluorine atom at 4-position, a bromine atom at 3-position, a bromine atom at 4-position, methoxy at 2-position, methoxy at 3-position, methoxy at 4-position, a chlorine atom at 4-position, methyl at 4-position, or nitro at 4-position.

5. A compound of formula (Id) or a pharmaceutically acceptable salt thereof:

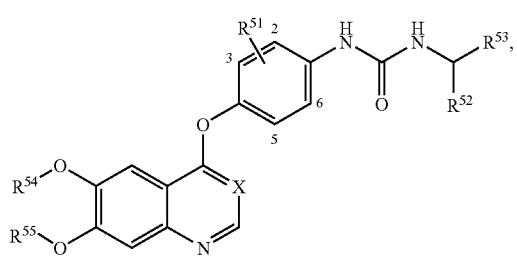

wherein
X represents CH or N,
R$^{51}$ represents a hydrogen atom, a fluorine atom at 2-position, a fluorine atom at 3-position, methoxy at 2-position, methoxy at 3-position, or methyl at 2- and 5-positions,
R$^{52}$ represents methyl,
R$^{53}$ represents imidazolyl, pyrazolyl, oxazolyl, isoxazolyl, thiazolyl, or isothiazolyl in which one or two hydrogen atoms on the groups are optionally substituted by a halogen atom or C$_{1-4}$ alkyl, and
R$^{54}$ and R$^{55}$ which may be the same or different, represent a hydrogen atom or C$_{1-6}$ alkyl in which the alkyl group is optionally substituted by hydroxyl; a halogen atom; —OR$^{56}$ wherein R$^{56}$ represents C$_{1-4}$ alkyl; —NR$^{57}$R$^{58}$ wherein R$^{57}$ and R$^{58}$, which may be the same or different, represent a hydrogen atom or C$_{1-4}$ alkyl in which the alkyl group is optionally substituted by hydroxyl or —OR$^{59}$ wherein R$^{59}$ represents C$_{1-4}$ alkyl; or a saturated or unsaturated three- to seven-membered carbocyclic or heterocyclic group in which the carbocyclic and heterocyclic groups are optionally substituted by one or two halogen atoms or C$_{1-4}$ alkyl.

6. The compound according to claim 5, wherein X represents CH, and R$^{52}$ represents

7. The compound according to claim 6, wherein R$^{54}$ and R$^{55}$ represent methyl.
8. The compound according to claim 6, wherein
R$^{54}$ represents methyl, and
R$^{55}$ represents C$_{1-4}$ alkyl substituted by a saturated or unsaturated five- or six-membered carbocyclic or heterocyclic group.
9. The compound according to claim 5, wherein
X represents CH, and
R$^{52}$ represents

10. The compound according to claim 9, wherein R$^{54}$ and R$^{55}$ represent methyl.

11. The compound according to claim 9, wherein
R$^{54}$ represents methyl, and
R$^{55}$ represents C$_{1-4}$ alkyl substituted by a saturated or unsaturated five- or six-membered carbocyclic or heterocyclic group.
12. The compound according to claim 5, wherein
X represents N, and
R$^{52}$ represents

13. The compound according to claim 12, wherein R$^{54}$ and R$^{55}$ represent methyl.
14. The compound according to claim 12, wherein
R$^{54}$ represents methyl, and
R$^{55}$ represents C$_{1-4}$ alkyl substituted by a saturated or unsaturated five- or six-membered carbocyclic or heterocyclic group.
15. The compound according to claim 5, wherein
X represents N, and
R$^{52}$ represents

16. The compound according to claim 15, wherein R$^{54}$ and R$^{55}$ represent methyl.
17. The compound according to claim 15, wherein
R$^{54}$ represents methyl, and
R$^{55}$ represents C$_{1-4}$ alkyl substituted by a saturated or unsaturated five- or six-membered carbocyclic or heterocyclic group.
18. A compound of formula (Ie) or a pharmaceutically acceptable salt ef-sel*ate thereof:

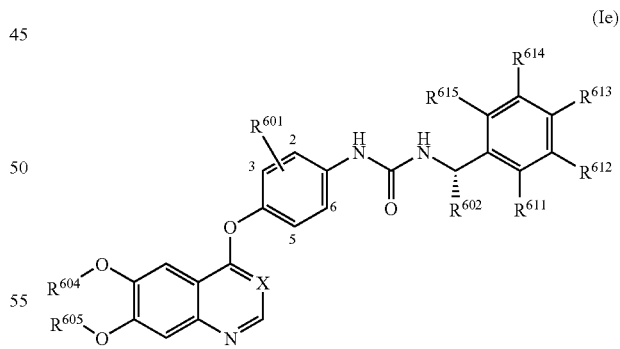

wherein
R$^{601}$ represents a hydrogen atom, a fluorine atom at 2-position, a fluorine atom at 3-position, a chlorine atom at 2-position, a chlorine atom at 3-position, methyl at 2- and 3-positions, methyl at 2- and 5-positions, methoxy at 2-position, methoxy at 3-position, methyl at 2-position, or trifluoromethyl at 2-position,
R$^{602}$ represents methyl,
X represents N or CH, $R^{604}$ and $R^{605}$, which may be the same or different, represent a hydrogen atom or $C_{1-6}$ alkyl in which the alkyl group is optionally substituted by hydroxyl; a halogen atom; —$OR^{606}$ wherein $R^{606}$ represents $C_{1-4}$ alkyl; —$NR^{607}R^{608}$, wherein $R^{607}$ and $R^{608}$, which may be the same or different, represent a hydrogen atom or $C_{1-4}$ alkyl in which the alkyl group is optionally substituted by hydroxyl or —$OR^{609}$ wherein $R^{609}$ represents $C_{1-4}$ alkyl; or a saturated or unsaturated three- to seven-membered carbocyclic or heterocyclic group in which the carbocyclic and heterocyclic groups are optionally substituted by one or two halogen atoms or $C_{1-4}$ alkyl, and $R^{611}$, $R^{612}$, $R^{613}$, $R^{614}$, and $R^{615}$, which may be the same or different, represent a hydrogen atom; $C_{1-6}$ alkyl; —$OR^{616}$ wherein $R^{616}$ represents $C_{1-4}$ alkyl; a halogen atom; nitro; or —$NNR^{617}R^{618}$ wherein $R^{617}$ and $R^{618}$, which may be the same or different, represent a hydrogen atom or $C_{1-4}$ alkyl in which the alkyl group is optionally substituted by hydroxyl, —$OR^{619}$ wherein $R^{619}$ represents $C_{1-4}$ alkyl or $NR^{620}R^{621}$ wherein $R^{620}$ and $R^{621}$, which may be the same or different, represent a hydrogen atom or $C_{1-4}$ alkyl.

19. The compound according to claim 18, wherein X represents CH and all of $R^{611}$, $R^{612}$, $R^{613}$, $R^{614}$, and $R^{615}$ represent a hydrogen atom, or any one of $R^{611}$, $R^{612}$, $R^{613}$, $R^{614}$, and $R^{615}$ represents a group other than a hydrogen atom and the remaining groups represent a hydrogen atom.

20. The compound according to claim 19, wherein all of $R^{611}$, $R^{612}$, $R^{613}$, $R^{614}$, and $R^{614}$, represent a hydrogen atom, or any one of $R^{611}$, $R^{612}$, $R^{613}$, $R^{614}$, and $R^{615}$ represents $C_{1-6}$ alkyl, —$OR^{616}$, a halogen atom, or nitro and the remaining groups represent a hydrogen atom.

21. The compound according to claim 20, wherein $R^{611}$ represents methoxy and $R^{612}$, $R^{613}$, $R^{614}$, and $R^{615}$ represent a hydrogen atom, or $R^{612}$ represents a bromine atom or methoxy and $R^{611}$, $R^{613}$, $R^{614}$, and $R^{615}$ represent a hydrogen atom, or $R^{613}$ represents a bromine atom, a chlorine atom, a fluorine atom, methyl, methoxy, or nitro and $R^{611}$, $R^{612}$, $R^{614}$ and $R^{615}$ represent a hydrogen atom.

22. The compound according to claim 19, wherein $R^{604}$ and $R^{605}$ represent methyl.

23. The compound according to claim 19, wherein $R^{604}$ represents methyl and $R^{605}$ represents $C_{1-4}$ alkyl substituted by a saturated or unsaturated five- or six-membered carbocyclic or heterocyclic group.

24. The compound according to claim 18, wherein X represents N and all of $R^{611}$, $R^{612}$, $R^{613}$, $R^{614}$, and $R^{615}$ represent a hydrogen atom, or any one of $R^{611}$, $R^{612}$, $R^{613}$, $R^{614}$, and $R^{615}$ represents a group other than a hydrogen atom and the remaining groups represent a hydrogen atom.

25. The compound according to claim 24, wherein all of $R^{611}$, $R^{612}$, $R^{613}$, $R^{614}$, $R^{615}$ represent a hydrogen atom, or any one of $R^{611}$, $R^{612}$, $R^{613}$, $R^{614}$, and $R^{615}$ represents $C_{1-6}$ alkyl, —$OR^{616}$, a halogen atom, or nitro and the remaining groups represent a hydrogen atom.

26. The compound according to claim 25, wherein $R^{611}$ represents methoxy and $R^{612}$, $R^{613}$, $R^{614}$, and $R^{615}$ represent a hydrogen atom, or $R^{612}$ represents a bromine atom or methoxy and $R^{611}$, $R^{613}$ $R^{614}$, and $R^{615}$ represent a hydrogen atom, or $R^{613}$ represents a bromine atom, a chlorine atom, a fluorine atom, methyl, methoxy, or nitro and $R^{611}$, $R^{612}$, $R^{614}$, and $R^{615}$ represent a hydrogen atom.

27. The compound according to claim 24, wherein $R^{604}$ and $R^{605}$ represent methyl.

28. The compound according to claim 24, wherein $R^{604}$ represents methyl and $R^{605}$ represents $C_{1-4}$ alkyl substituted by a saturated or unsaturated five- or six-membered carbocyclic or heterocyclic group.

29. A compound of formula (If) or a pharmaceutically acceptable salt thereof:

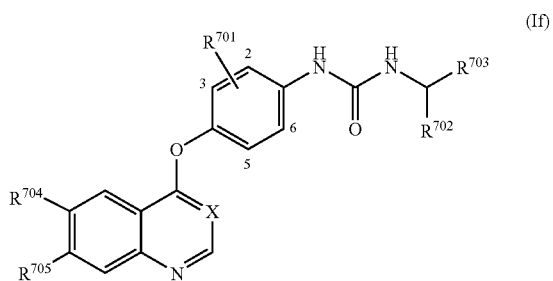

wherein

X represents CH or N, $R^{701}$ represents a hydrogen atom, a fluorine atom at 2-position, a fluorine atom at 3-position, methoxy at 2-position, methoxy at 3-position, or methyl at 2- and 5-positions, $R^{702}$ represents $C_{1-4}$ alkyl, $R^{703}$ represents imidazolyl, pyrazolyl, oxazolyl, isoxazolyl, thiazolyl, or isothiazolyl in which one or two hydrogen atoms on the groups are optionally substituted by a halogen atom or $C_{1-4}$ alkyl, and $R^{704}$ and $R^{705}$, which may be the same or different, represent a hydrogen atom; hydroxyl; nitro; cyano; a halogen atom; —$NR^{706}R^{707}$ wherein $R^{706}$ and $R^{707}$, which may be the same or different, represent a hydrogen atom or $C_{1-4}$ alkyl in which the alkyl group is optionally substituted by hydroxyl, $OR^{708}$ wherein $R^{708}$ represents $C_{1-4}$ alkyl, or —$NR^{709}R^{710}$ wherein $R^{709}$ and $R^{710}$, which may be the same or different, represent a hydrogen atom or alkyl; $CONR^{711}R^{712}$ wherein $R^{711}$ and $R^{712}$, which may be the same or different, represent a hydrogen atom or $C_{1-4}$ alkyl in which the alkyl group is optionally substituted by hydroxyl, —$OR^{713}$ wherein $R^{713}$ represents $C_{1-4}$ or —$NR^{714}R^{715}$ wherein $R^{714}$ and $R^{715}$, which may be the same or different, represent a hydrogen atom or $C_{1-4}$ alkyl; $COOR^{716}$ wherein $R^{716}$ represents a hydrogen atom or $C_{1-4}$ alkyl in which the alkyl group is optionally substituted by hydroxyl, —$OR^{717}$ wherein $R^{717}$ represents $C_{1-4}$ alkyl, or —$NR^{718}R^{719}$ wherein $R^{718}$ and $R^{719}$, which may be the same or different, represent a hydrogen atom or $C_{1-4}$ alkyl; $C_{1-6}$ alkyl; $C_{2-6}$ alkenyl; $C_{2-6}$ alkynyl; or $C_{1-6}$ alkoxy, in which the alkyl, alkenyl, alkynyl, and alkoxy groups are optionally substituted by hydroxyl, a halogen atom, —$OR^{720}$ in which $R^{720}$ represents $C_{1-4}$ alkyl, —$NR^{721}R^{722}$ wherein $R^{721}$ and $R^{722}$, which may be the same or different, represent a hydrogen atom or $C_{1-4}$ alkyl in which the alkyl group is optionally substituted by hydroxyl or —$OR^{723}$ wherein $R^{723}$ represents $C_{1-4}$ alkyl, or a saturated or unsaturated three- to seven-membered carbocyclic or heterocyclic group in which the carbocyclic and heterocyclic groups are optionally substituted by one or two halogen atoms or $C_{1-4}$ alkyl.

30. The compound according to claim 20, wherein X represents CH, and $R^{702}$ represents

31. The compound according to claim 30, wherein $R^{702}$ represents methyl.
32. The compound according to claim 30, wherein $R^{704}$ and $R^{705}$ represent methoxy.
33. The compound according to claim 30, wherein $R^{704}$ represents methoxy, and $R^{705}$ represents $C_{1-4}$ alkoxy substituted by a saturated or unsaturated five- or six-membered carbocyclic or heterocyclic group.
34. The compound according to claim 29, wherein X represents CH, and $R^{702}$ represents

35. The compound according to claim 34, wherein $R^{702}$ represents methyl.
36. The compound according to claim 34, wherein $R^{704}$ and $R^{705}$ represent methoxy.
37. The compound according to claim 34, wherein R704 represents methoxy, and $R^{705}$ represents $C_{1-4}$ alkoxy substituted by a saturated or unsaturated five- or six-membered carbocyclic or heterocyclic group.
38. The compound according to claim 29, wherein X represents N, and $R^{702}$ represents

39. The compound according to claim 38, wherein $R^{702}$ represents methyl.
40. The compound according to claim 38, wherein $R^{704}$ and $R^{705}$ represent methoxy.
41. The compound according to claim 38, wherein $R^{704}$ represents methoxy, $R^{705}$ represents $C_{1-4}$ alkoxy substituted by a saturated or unsaturated five- or six-membered carbocyclic or heterocyclic group.
42. The compound according to claim 29, wherein X represents N, and $R^{702}$ represents

43. The compound according to claim 42, wherein $R^{702}$ represents methyl.
44. The compound according to claim 42, wherein $R^{704}$ and $R^{705}$ represent methoxy.
45. The compound according to claim 42, wherein $R^{704}$ represents methoxy, and $R^{705}$ represents $C_{1-4}$ alkoxy substituted by a saturated or unsaturated five- or six-membered carbocyclic or heterocyclic group.

46. A compound of formula (Ig) or a pharmaceutically acceptable salt thereof:

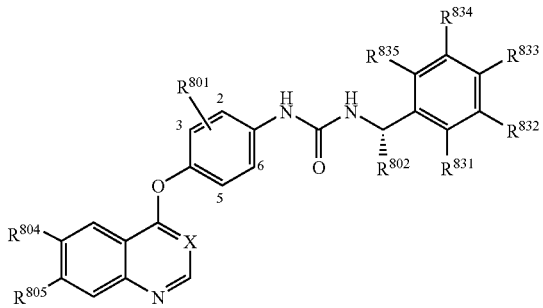

wherein
X represents CH or N,
$R^{801}$ represents a hydrogen atom, a fluorine atom at 2-position, a fluorine atom at 3-position, a chlorine atom at 2-position, a chlorine atom at 3-position, methyl at 2- and 3-positions, methyl at 2- and 5-positions, methoxy at 2-position, methoxy at 3-position, methyl at 2-position, or trifluoromethyl at 2-position,
$R^{802}$ represents $C_{1-4}$ alkyl,
$R^{804}$ and $R^{805}$, which may be the same or different, represent a hydrogen atom; hydroxyl; nitro; cyano; a halogen atom; —$NR^{806}R^{807}$ wherein $R^{806}$ and $R^{807}$, which may be the same or different, represent a hydrogen atom or $C_{1-4}$ alkyl in which the alkyl group is optionally substituted by hydroxyl, —$OR^{808}$ wherein $R^{808}$ represents $C_{1-4}$ alkyl, or $NR^{809}R^{810}$ wherein $R^{809}$ and $R^{810}$, which may be the same or different, represent a hydrogen atom or alkyl; CONR $R^{811}R^{810}$ wherein $R^{811}$ and $R^{812}$, which may be the same or different, represent a hydrogen atom or $C_{1-4}$ alkyl in which the alkyl group is optionally substituted by hydroxyl, —$OR^{813}$ wherein $R^{813}$ represents $C_{1-4}$ alkyl, or —$NR^{814}R^{815}$ wherein $R^{814}$ and $R^{815}$, which may be the same or different, represent a hydrogen atom or $C_{1-4}$ alkyl; —OOR $^6$ wherein $R^{816}$ represents a hydrogen atom or $C_{1-4}$ alkyl in which the alkyl group is optionally substituted by hydroxyl, —$OR^{817}$ wherein $R^{817}$ represents $C_{1-4}$ alkyl, or —$NR^{818}R^{819}$ wherein $R^{818}$ and $R^{819}$, which may be the same or different, represent a hydrogen atom or $C_{1-4}$ alkyl; $C_{1-6}$ alkyl; $C_{2-6}$ alkenyl; $C_{2-6}$ alkynyl; or $C_{1-6}$ alkoxy, in which the alkyl, alkenyl, alkynyl, and alkoxy groups are optionally substituted by hydroxyl, a halogen atom, —$OR^{820}$ in which $R^{820}$ represents $C_{1-4}$ alkyl, —$NR^{821}R^{822}$ wherein $R^{821}$ and $R^{822}$, which may be the same or different, represent a hydrogen atom or $C_{1-4}$ alkyl in which the alkyl group is optionally substituted by hydroxyl or —$OR^{823}$ wherein $R^{823}$ represents $C_{1-4}$ alkyl, or a saturated or unsaturated three- to seven-membered carbocyclic or heterocyclic group in which the carbocyclic and heterocyclic groups are optionally substituted by one or two halogen atoms or $C_{1-4}$ alkyl, and
$R^{831}$, $R^{832}$, $R^{833}$, $R^{834}$, and $R^{835}$, which may be the same or different, represent a hydrogen atom; hydroxyl; $C_{1-6}$ alkyl; $R^{836}$ wherein $R^{836}$ represents $C_{1-4}$ alkyl; a halogen atom; nitro; or —$NR^{837}$ $R^{838}$ wherein $R^{837}$ and $R^{838}$, which may be the same or different, represent a hydrogen atom or $C_{1-4}$ alkyl in which the alkyl group is optionally substituted by hydroxyl, —$OR^{839}$ wherein $R^{839}$ represents $C_{1-4}$ alkyl, or —$NR^{840}R^{841}$ wherein $R^{831}$, and $R^{832}$, which may be the same or different, represent a hydrogen atom or $C_{1-4}$ alkyl.

47. The compound according to claim 46, wherein X represents CH and all of $R^{831}$, $R^{832}$, $R^{833}$, $R^{834}$, and $R^{835}$ represent a hydrogen atom, or any one of $R^{831}$, $R^{832}$, $R^{833}$ $R^{834}$ and $R^{835}$ represents a group other than a hydrogen atom and the remaining groups represent a hydrogen atom.

48. The compound according to claim 47, wherein all of $R^{831}$, $R^{832}$, $R^{833}$ $R^{834}$ and $R^{835}$ represent a hydrogen atom, or any one of $R^{831}$, $R^{832}$, $R^{833}$, $R^{834}$, and $R^{835}$ represents $C_{1-6}$ alkyl, —$OR^{836}$, a halogen atom, or nitro and the remaining groups represent a hydrogen atom.

49. The compound according to claim 47, wherein $R^{831}$ represents methoxy and $R^{832}$, $R^{833}$, $R^{834}$, and $R^{835}$ represent a hydrogen atom, or $R^{832}$ represents a bromine atom or methoxy and $R^{831}$, $R^{833}$, $R^{834}$, and $R^{835}$ represent a hydrogen atom, or $R^{833}$ represents a bromine atom, a chlorine atom, a fluorine atom, methyl, methoxy, or nitro and $R^{831}$, $R^{832}$, $R^{834}$, and $R^{835}$ represent a hydrogen atom.

50. The compound according to claim 47, wherein $R^{804}$ and $R^{805}$ represent methoxy.

51. The compound according to claim 47, wherein $R^{804}$ represents methoxy and $R^{805}$ represents $C_{1-4}$ alkoxy substituted by a saturated or unsaturated five- or six-membered carbocyclic or heterocyclic group.

52. The compound according to claim 46, wherein X represents CH, $R^{802}$ represents methyl, and all of $R^{831}$, $R^{832}$, $R^{833}$, $R^{834}$, and $R^{835}$ represent a hydrogen atom, or any one of $R^{831}$, $R^{832}$, $R^{833}$, $R^{834}$ and $R^{835}$ represents a group other than a hydrogen atom and the remaining groups represent a hydrogen atom.

53. The compound according to claim 52, wherein all of $R^{831}$, $R^{832}$ $R^{833}$, $R^{834}$, and $R^{835}$ represent a hydrogen atom, or any one of $R^{831}$, $R^{832}$, $R^{833}$, $R^{834}$, and $R^{835}$ represents $C_{1-6}$ alkyl, —$OR^{836}$, a halogen atom, or nitro and the remaining groups represent a hydrogen atom.

54. The compound according to claim 52, wherein $R^{831}$ represents methoxy and $R^{832}$, $R^{833}$, $R^{834}$, and $R^{835}$ represent a hydrogen atom, or $R^{832}$ represents a bromine atom or methoxy and $R^{831}$, $R^{833}$, $R^{834}$ and $R^{835}$ represent a hydrogen atom, or $R^{833}$ represents a bromine atom, a chlorine atom, a fluorine atom, methyl, methoxy, or nitro and $R^{831}$, $R^{832}$, $R^{834}$, and $R^{835}$ represent a hydrogen atom.

55. The compound according to claim 52, wherein $R^{804}$ and $R^{805}$ represent methoxy.

56. The compound according to claim 52, wherein $R^{804}$ represents methoxy and $R^{805}$ represents $C_{1-4}$ alkoxy substituted by a saturated or unsaturated five- or six-membered carbocyclic or heterocyclic group.

57. The compound according to claim 46, wherein X represents N and all of $R^{831}$, $R^{832}$, $R^{833}$, $R^{834}$ and $R^{835}$ represent a hydrogen atom, or any one of $R^{831}$, $R^{832}$, $R^{833}$, $R^{834}$, and $R^{835}$ represents a group other than a hydrogen atom and the remaining groups represent a hydrogen atom.

58. The compound according to claim 57, wherein all of $R^{831}$, $R^{832}$, $R^{833}$, $R^{834}$, and $R^{835}$ represent a hydrogen atom, or any one of $R^{831}$, $R^{832}$, $R^{833}$, $R^{834}$, and $R^{835}$ represents $C_{1-6}$ alkyl, —$OR^{836}$, a halogen atom, or nitro and the remaining groups represent a hydrogen atom.

59. The compound according to claim 57, wherein $R^{831}$ represents methoxy and $R^{832}$, $R^{833}$, $R^{834}$, and $R^{835}$ represent a hydrogen atom, or $R^{832}$ represents a bromine atom or methoxy and $R^{831}$, $R^{833}$, $R^{834}$, and $R^{835}$ represent a hydrogen atom, or $R^{833}$ represents a bromine atom, a chlorine atom, a fluorine atom, methyl, methoxy, or nitro and $R^{831}$, $R^{832}$, $R^{834}$, and $R^{835}$ represent a hydrogen atom.

60. The compound according to claim 57, wherein $R^{804}$ and $R^{805}$ represent methoxy.

61. The compound according to claim 57, wherein $R^{804}$ represents methoxy and $R^{805}$ represents $C_{1-4}$ alkoxy substituted by a saturated or unsaturated five- or six-membered carbocyclic or heterocyclic group.

62. The compound according to claim 46, wherein X represents N, $R^{802}$ represents methyl, and all of $R^{831}$, $R^{832}$, $R^{833}$, $R^{834}$, and $R^{835}$ represent a hydrogen atom, or any one of $R^{831}$, $R^{832}$, $R^{833}$, $R^{834}$, and $R^{835}$ represents a group other than a hydrogen atom and the remaining groups represent a hydrogen atom.

63. The compound according to claim 62, wherein all of $R^{831}$, $R^{832}$, $R^{833}$, $R^{834}$, and $R^{835}$ represent a hydrogen atom, or any one of $R^{831}$, $R^{832}$, $R^{833}$, $R^{834}$, and $R^{835}$ represents $C_{1-6}$ alkyl, —$OR^{836}$, a halogen atom, or nitro and the remaining groups represent a hydrogen atom.

64. The compound according to claim 62, wherein $R^{831}$ represents methoxy and $R^{832}$, $R^{833}$, $R^{834}$, and $R^{835}$ represent a hydrogen atom, or $R^{832}$ represents a bromine atom or methoxy and $R^{831}$, $R^{833}$, $R^{834}$, and $R^{835}$ represent a hydrogen atom, or $R^{833}$ represents a bromine atom, a chlorine atom, a fluorine atom, methyl, methoxy, or nitro and $R^{831}$, $R^{832}$, $R^{834}$, and $R^{835}$ represent a hydrogen atom.

65. The compound according to claim 62, wherein $R^{804}$ and $R^{805}$ represent methoxy.

66. The compound according to claim 62, wherein $R^{804}$ represents methoxy and $R^{805}$ represents $C_{1-4}$ alkoxy substituted by a saturated or unsaturated five- or six-membered carbocyclic or heterocyclic group.

67. A pharmaceutical composition comprising a compound according to any one of claims 1,4,5,18,29 or 46, or a pharmaceutically acceptable salt thereof as an active ingredient.

68. A method for treating osteoporosis or bone metastasis of a malignant tumor-comprising:
administering a therapeutically effective amount of a compound of formula I or a pharmaceutically acceptable salt thereof to a mammal in need thereof,
wherein formula I is:

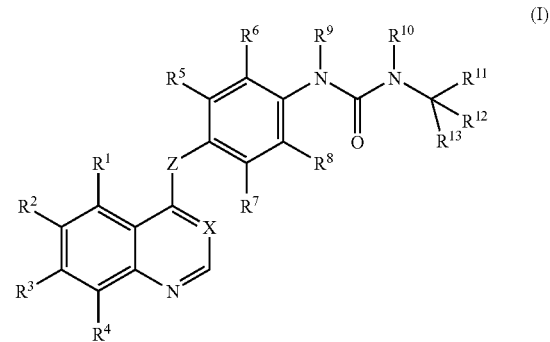

wherein
X represents CH or N;
Z represents O or S;
$R^1$, $R^2$, and $R^3$, which may be the same or different, represent a hydrogen atom; a halogen atom; hydroxyl; cyano; $C_{1-6}$ alkyl; $C_{1-6}$ alkoxy; $C_{2-6}$ alkenyl; $C_{2-6}$ alkynyl; nitro; —$NR^{106}R^{107}$ wherein $R^{106}$ and $R^{107}$, which may be the same or different, represent a hydrogen atom or $C_{1-4}$ alkyl in which the alkyl group is optionally substituted by hydroxyl, —OR$^{108}$ wherein R$^{108}$ represents $C_{1-4}$ alkyl, or —NR$^{109}$R$^{110}$ wherein R$^{109}$ and R$^{110}$, which may be the same or different, represent a hydrogen atom or $C_{1-4}$ alkyl; —CONR$^{111}$R$^{112}$ wherein R$^{111}$ and R$^{112}$, which may be the same or different, represent a hydrogen atom or $C_{1-4}$ alkyl in which the alkyl group is optionally substituted by hydroxyl, —OR$^{113}$ wherein R$^{113}$ represents $C_{1-4}$ alkyl, or —NR$^{114}$R$^{115}$ wherein R$^{114}$ and R$^{115}$, which maybe the same or different, represent a hydrogen atom or $C_{1-4}$ alkyl; or —COOR$^{116}$ wherein R$^{116}$ represents a hydrogen atom or alkyl in which the alkyl group is optionally substituted by hydroxyl, —OR$^{117}$ wherein R$^{117}$ represents $C_{1-4}$ alkyl, or —NR$^{118}$R$^{119}$ wherein R$^{118}$ and R$^{119}$, which maybe the same or different, represent a hydrogen atom or $C_{1-4}$ alkyl in which the $C_{1-6}$ alkyl, $C_{1-6}$ alkoxy, $C_{2-6}$ alkenyl, and $C_{2-6}$ alkynyl groups are optionally substituted by a halogen atom; hydroxyl; $C^{1-4}$ alkyl; $C_{1-4}$ alkoxy; $C_{1-4}$ alkoxycarbonyl; amino in which one or two hydrogen atoms on the amino group each are optionally substituted by $C_{1-4}$ alkyl optionally substituted by hydroxyl or $C_{1-4}$ alkoxy; group R$^{15}$R$^{16}$N—C(=O)—O— wherein R$^{15}$ and R$^{16}$, which may be the same or different, represent a hydrogen atom or $C_{1-4}$ alkyl in which the alkyl group is optionally substituted by hydroxyl or $C_{1-4}$ alkoxy; or group R$^{17}$—(S)m— wherein R$^{17}$ represents a saturated or unsaturated three- to seven-membered carbocyclic or heterocyclic group optionally substituted by a halogen atom or $C_{1-4}$ alkyl and m is 0 (zero) or 1, R$^4$ represents a hydrogen atom, R$^5$, R$^6$, R$^7$, and R$^8$, which may be the same or different, represent a hydrogen atom, a halogen atom, $C_{1-4}$ alkyl, $C_{1-4}$ alkoxy, $C_{1-4}$ alkylthio, trifluoromethyl, nitro, or amino, R$^{19}$ and R$^0$, which may be the same or different, represent a hydrogen atom, $C_{1-6}$ alkyl, or $C_{1-4}$ alkylcarbonyl, and any one of R$^{11}$ and R$^{12}$ represents a hydrogen atom while the other represents $C_{1-4}$ alkyl, and R$^{13}$ represents a saturated or unsaturated three- to seven-membered carbocyclic or heterocyclic group or a saturated or unsaturated nine- to twelve-membered bicylic carbocyclic group in which the carbocyclic and heterocyclic groups are optionally substituted by a halogen atom; hydroxyl; $C_{1-4}$ alkyl; $C_{1-4}$ alkoxy; $C_{1-4}$ alkylthio; trifluoromethyl; nitro; or —NR$^{137}$R$^{138}$ wherein R$^{137}$ and R$^{138}$, which may be the same or different, represent a hydrogen atom or $C_{1-4}$ alkyl in which the alkyl group is optionally substituted by hydroxyl, —OR$^{139}$ wherein R$^{139}$ represents $C_{1-4}$ alkyl, or —NR$^{140}$R$^{141}$ wherein R$^{140}$ and R$^{141}$, which may be the same or different, represent a hydrogen atom or $C_{1-4}$ alkyl, or R$^{11}$ represents a hydrogen atom, and R$^{12}$ and R$^{13}$ may combine with a carbon atom attached thereto to form a saturated or unsaturated nine- to twelve-membered bicyclic carbocyclic group.

69. The method according to claim 68, wherein the disease is osteoporosis.

70. The method of claim 69, wherein the disease is a bone metastasis of a malignant tumor where the malignant tumor is selected from the group consisting of breast cancer, prostatic cancer, lung cancer, and multiple myeloma.

71. The compound according to claim 1, which is selected from the group consisting of:
(70)N- {4-[(6,7-dimethoxy-4-quinolyl)oxy]-2-fluorophenyll-N'-[1-(1,3-thiazol-2-yl)ethyl]urea;
(71)N-{4-[(6,7-dimethoxy-4-quinolyl)oxy]-2-fluorophenyl}-N'--[(1S)-1-(1,3-thiazol-2-yl)ethyl]urea;
(72)N-{4[(6,7-dimethoxy-4-quinolyl)oxy]-2-fluorophenyl)-N'-[(1R)-1-(1,3-thiazol-2-yl)ethyl]urea;
(73)N-{4-[(6,7-dimethoxy-4-quinolyl)oxy]-3-fluorophenyl}-N'-[1-(1,3-thiazol-2-yl)ethyl]urea;
(74)N-{4[(6,7-dimethoxy-4-quinolyl)oxy]-2-methoxyphenyl}-N'-[1-(1,3-thiazol-2-yl)ethyl]urea;
(75)N-{4-[(6,7-dimethoxy-4-quinolyl)oxy]-2-methoxyphenyl}-N'-[(1S)-1-(1,3-thiazol-2-yl)ethyl]urea;
(76)N-{4-[(6,7-dimethoxy-4-quinolyl)oxy]-2-methoxyphenyl) -N'-[(1R)-1-(1,3-thiazol-2-yl)ethyl]urea;
(77)N-{4-[(6,7-dimethoxy-4-quinolyl)oxy]phenyl }-N'-[1-(1,3-thiazol-2-yl)ethyl]urea;
(78)N-{4-[(6,7-dimethoxy-4-quinolyl)oxy]phenyl }-N'-[(1S)-1-(1,3-thiazol-2-yl)ethyl]urea;
(79)N-{4-[(6,7-dimethoxy-4-quinolyl)oxy]phenyl }-N'-[(1R)-1--(1,3-thiazol-2-yl)ethyl]urea;
(80)N-{4-[(6,7-dimethoxy-4-quinolyl)oxy]-3-methoxyphenyl }-N'-[1-(1,3-thiazol-2-yl)ethyl]urea; (81) N-{4-[(6,7-dimethoxy-4-quinolyl)oxy]-3-methoxyphenyl }-N'-[(1S)-1-(1,3-thiazol-2-yl)ethyl]urea;
(82)N-{4-[(6,7-dimethoxy-4-quinolyl)oxy]-3-methoxyphenyl }-N'-[(1R)-1-(1,3-thiazol-2-yl)ethyl]urea;
(86)N-{4-[(6,7-dimethoxy-4-quinolyl)oxy]-2,5-dimethylphenyl }-N'-[(1S)-1-(1,3-thiazol-2-yl)ethyl]urea;
(87)N-{4[(6,7-dimethoxy-4-quinolyl)oxy]-2,5-dimethylphenyl )-N'-[(1R)-1-(1,3-thiazol-2-yl)ethyl]urea;
(88)N-{4-[(6,7-dimethoxy-4-quinolyl)oxy]-2-fluorophenyl}-N'-11-(4-methyl-1,3-thiazol-2-yl)ethyl]urea;
(89)N-{4-[(6,7-dimethoxy-4-quinolyl)oxy]-3-fluorophenyl}-N'-[1-(4-methyl-1,3-thiazol-2-yl)ethyl]urea;
(90)N-{4-[(6,7-dimethoxy-4-quinolyl)oxy]-2-methoxyphenl}-N'-[1-(4-methyl-1,3-thiazol-2-yl)ethyl]urea;
(91)N-{4-[(6,7-dimethoxy-4-quinolyl)oxy]phenyl)-N'-[1-(4-methyl-1,3-thiazol-2-yDethyl]urea;
(93)N-{4-[(6,7-dimethoxy-4-quinolyl)oxy]-2,5-dimethylphenyl}-N'-[1-(4-methyl-1,3-thiazol-2-yl)ethyl]urea;
(94)N-{4-[(6,7-dimethoxy-4-quinolyl)oxy]phenyl}-N'-[1-(4,5-dimethyl-1,3-thiazol-2-yl)ethyl]urea;
(95)N-{4-[(6,7-dimethoxy-4-quinolyl)oxy]-2-fluorophenyll-N'-[1-(4,5-dimethyl-1,3-thiazol-2-yl)ethyl]urea;
(98)N-{4-[(6,7-dimethoxy-4-quinolyl)oxy]-2,5-dimethylphenyl)-N'-[1-(4,5-dimethyl-1,3-thiazol-2-yl)ethyl]urea;
(99)N-{4-[(6,7-dimethoxy-4-quinolyl)oxy]-2-methoxyphenyl }-N'-[1-(4,5-dimethyl-1,3-thiazol-2-yl)ethyl]urea;
(100)N-{4-[(6,7-dimethoxy-4-quinolyl)oxy]phenyl}-N'-[1-(5- methyl-1,3-thiazol-2-yl)ethyl]urea;
(101)N-{4-[(6,7-dimethoxy-4-quinolyl)oxy]-2-fluorophenyl)-N'-[1-(5-methyl-1,3-thiazol-2-yl)ethyl]urea; and
(105)N-{4-[(6,7-dimethoxy-4-quinolyl)oxy]-2-methoxyphenyl }-N'-[1-(5-methyl-1,3-thiazol-2-yl)ethyl]urea.

72. The compound according to claim 4, which is selected from the group consisting of:
(2)N-{4-[(6,7-dimethoxy-4-quinolyl)oxy]phenyl )-N'-[(1S)-1-(4-fluorophenyl)ethyl]urea;
(5)N-{2-Chloro-4-[(6,7-dimethoxy-4-quinolyl)oxy]phenyl }-N'-[(1S)-1-(4-fluorophenyl)ethyl]urea;
(8)N-{4-[(6,7-dimethoxy-4-quinolyl)oxy]-2,5-dimethylphenyl }-N'-[(1S)-1-(4-fluorophenyl)ethyl]urea;
(11)N-{3-Chloro-4-[(617-dimethoxy-4-quinolyl)oxy]phenyl)-N'-[(1S)-1-(4-fluorophenyl)ethyl]urea;
(14)N-{4-[(6,7-dimethoxy-4-quinolyl)oxy]-2-methylphenyl }-N'[(1S)-1-(4-fluorophenyl)ethyl]urea;

(17) N-{4-[(6,7-dimethoxy-4-quinolyl)oxy]-2-methoxyphenyl}-N'-[(1S)-1-(4-fluorophenyl)ethyl]urea;

(20) N-[4-(6,7-dimethoxy-4-quinolyl)oxy]-2-(trifluoromethyl) phenyl]-N'-(1S)-1-(4-fluorophenyl)ethyl]urea;

(23) N-{4-[(6,7-dimethoxy-4-quinolyl)oxy]-3-methoxyphenyl]-N'[(1S)-1-(4-fluorophenyl)ethyl]urea;

(26) N-{4-[(6,7-dimethoxy-4-quinolyl)oxy]-2,3-dimethylphenyl}-N'-[(1S)-1-(4-fluorophenyl)ethyl]urea;

(29) N-{4-[(6,7-dLmethoxy-4-quinolyl)oxy]-2-fluorophenyl)-N'-[(1S)-1-(4-fluorophenyl)ethyl]urea;

(32) N-{4-[(6,7-dimethoxy-4-quinolyl)oxy]-3-fluorophenyl}-N'-[(1S)-1-(4-fluorophenyl)ethyl]urea;

(34) N-[(1S)-1-(4-bromophenyl)ethyl]-N'-{4-[(6,7-dimethoxy-4-quinolyl)oxy]phenyl}urea;

(35) N-{4-[(6,7-dimethoxy-4-quinolyl)oxy]pheflyl}-N'-(1S)-1-(4-nitrophenyl)ethyl]urea;

(41) N-{4-[(6,7-dimethoxy-4-quinolyl)oxy]phenyl}-W-[(1S)-1-(4-methylphenyl)ethyl]urea;

(46) N-[(1S)-1-(3-bromophenyl)ethyl]-N'-{4-[(6,7-dimethoxy-4-quinolyl)oxy]phenyl}urea;

(47) N-[(1S)-1-(4-chlorophenyl)ethyl]-N'-{4-[(6,7-dimethoxy-4-quinolyl)oxy]phenyl}urea;

(49) N-{4-[(6,7-dimethoxy-4-quinolyl)oxy]phenyl}-N'-[(1S)-1-(3-methoxyphenyl)ethyl]urea;

(51) N-{4-[(6,7-dimethoxy-4-quinolyl)oxy]phenyl}-N'-[(1S)-1-(2-methoxyphenyl)ethyl]urea; and

(53) N-{4-[(6,7-dimethoxy-4-quinolyl)oxy]phenyl}-N'-[(1S)-1-(4-methoxyphenyl)ethyl]urea.

* * * * *

UNITED STATES PATENT AND TRADEMARK OFFICE
CERTIFICATE OF CORRECTION

PATENT NO.       : 7,598,258 B2
APPLICATION NO.  : 10/510961
DATED            : October 6, 2009
INVENTOR(S)      : Kubo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1002 days.

Signed and Sealed this

Twenty-eighth Day of September, 2010

David J. Kappos
*Director of the United States Patent and Trademark Office*